US008679836B2

(12) United States Patent
Zudaire et al.

(10) Patent No.: US 8,679,836 B2
(45) Date of Patent: Mar. 25, 2014

(54) METHODS OF MONITORING ANGIOGENESIS AND METASTASIS IN THREE DIMENSIONAL CO-CULTURES

(75) Inventors: Enrique Zudaire, Germantown, MD (US); Frank Cuttitta, Adamstown, MD (US); Changge Fang, Alexandria, VA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 568 days.

(21) Appl. No.: 12/802,666

(22) Filed: Jun. 10, 2010

(65) Prior Publication Data
US 2010/0255528 A1 Oct. 7, 2010

Related U.S. Application Data

(63) Continuation-in-part of application No. 12/060,752, filed on Apr. 1, 2008, now abandoned.

(60) Provisional application No. 60/976,732, filed on Oct. 1, 2007.

(51) Int. Cl.
*C12N 5/07* (2010.01)
*C12N 5/00* (2006.01)
*C12N 5/02* (2006.01)
*C12N 1/00* (2006.01)

(52) U.S. Cl.
USPC ................ 435/347; 435/397; 435/404; 435/4

(58) Field of Classification Search
None
See application file for complete search history.

(56) References Cited

U.S. PATENT DOCUMENTS

| | | | |
|---|---|---|---|
| 5,972,639 A | 10/1999 | Parandoosh | |
| 6,232,523 B1 | 5/2001 | Tan et al. | |
| 6,248,904 B1 | 6/2001 | Zhang et al. | |
| 6,509,174 B2 | 1/2003 | Jordan et al. | |
| 6,828,111 B2 | 12/2004 | Shekhar et al. | |
| 6,893,812 B2 | 5/2005 | Woltering et al. | |
| 6,905,831 B2 | 6/2005 | Jiang et al. | |
| 7,085,765 B2 | 8/2006 | Zock et al. | |
| 7,235,373 B2 | 6/2007 | Dunlay et al. | |
| 2001/0031480 A1* | 10/2001 | Deisboeck et al. | 435/40.5 |
| 2002/0119441 A1* | 8/2002 | Elias | 435/4 |
| 2003/0108877 A1 | 6/2003 | Blais et al. | |
| 2004/0175765 A1 | 9/2004 | Singh et al. | |
| 2004/0231013 A1 | 11/2004 | Yang et al. | |
| 2005/0175980 A1 | 8/2005 | Libutti et al. | |
| 2005/0250177 A1 | 11/2005 | Yeboah et al. | |
| 2006/0198827 A1 | 9/2006 | Levenberg et al. | |
| 2010/0056390 A1 | 3/2010 | Fischbach | |

FOREIGN PATENT DOCUMENTS

WO  WO 99/17116   4/1999
WO  WO 2009/126725  10/2009

OTHER PUBLICATIONS

Khodarev et al. Tumour-endothelium interactions in co-culture: coordinated changes of gene expression profiles and phenotypic properties of endothelial cells. 2003. Journal of Cell Science. vol. 116, pp. 1013-1022.*
"An Image-Based Assay of Endothelial Cell Tube Formation as a Model of Angiogenesis," *BD Biosciences*, available online at www.bdbiosciences.com, pp. 1-4, accessed Apr. 1, 2008.
"Living Colors® Fluorescent Proteins. Illuminating Research & Drug Discovery," *Clontech Laboratories, Inc.*, pp. 1-5—available online at www.clontech.com, accessed Apr. 1, 2008.
Abbott, "Biology's new dimension," *Nature*, 424: 870-872 (2003).
Ades et al., "HMEC-1: Establishment of an Immortalized Human Microvascular Endothelial Cell Line," *The Journal of Investigative Dermatology*, 99(6): 683-699 (1992).
Alajati et al., "Spheroid-based engineering of a human vasculature in mice," *Nature Methods*, 5: 439-445 (2008).
Arnold et al., "Endometrial stromal cells regulate epithelial cell growth in vitro: a new co-culture model," *Human Reproduction*, 16(5): 836-845 (2001).
Baldridge et al., "Analysis of Fluorescent Protein Expression in Transformants of *Rickettsia monacensis*, an Obligate Intracellular Tick Symbiont," *Applied and Environmental Microbiology*, 71(4): 2095-2105 (2005).
Bannerman et al., "The Fas-associated death domain protein suppresses activation of NF-κB by LPS and IL-1β," *The Journal of Clinical Investigation*, 109(3): 419-425 (2002).
Beilmann et al., "Human primary co-culture angiogenesis assay reveals additive stimulation and different angiogenic properties of VEGF and HGF," *Cytokine*, 26: 178-185 (2004).
Belot et al., "Progesterone reduces the migration of mast cells toward the chemokine stromal cell-derived factor-1/CXCL12 with an accompanying decrease in CXCR4 receptors," *Am Journal of Physiol Endocrinol Metab*, 292: E1410-E1417 (2007).
Bissell et al., "Putting tumors in context," *Nature Reviews Cancer*, 1: 46-54 (2001).
Burch et al., "Development of a coculture system and use of confocal laser fluorescent microscopy to study human microvascular endothelial cell and mural cell interaction," *Microvascular Research*, 70: 43-52 (2005).
Butterfield et al., "Establishment of an Immature Mast Cell Line from a Patient with Mast Cell Leukemia," *Leukemia Research*, 12(4): 345-355 (1998).
Carter et al., "Endocytosis of Functional Epidermal Growth Factor Receptor-Green Fluorescent Protein Chimera," *The Journal of Biological Chemistry*, 273(52): 35000-35007 (1998).
Davis et al., "Mechanisms controlling human endothelial lumen formation and tube assembly in three-dimensional extracellular matrices," *Birth Defects Research (Part C)*, 81: 270-285 (2007).
Debnath J and Brugge, "Modeling glandular epithelial cancers in three-dimensional cultures," *Nature Review Cancer*, 5: 675-688 (2005).

(Continued)

Primary Examiner — Anne Gussow
Assistant Examiner — Channing S Mahatan
(74) Attorney, Agent, or Firm — Klarquist Sparkman, LLP

(57) ABSTRACT

This disclosure relates to fluorescent cell lines and to the use of such cell lines in monitoring cellular activity, such as angiogenesis. This disclosure further relates to the use of such cell lines in a three-dimensional cell culture to monitor angiogenic and metastatic potential of tumor cells and selecting personalized therapeutics for treatment of cancer.

20 Claims, 32 Drawing Sheets
(23 of 32 Drawing Sheet(s) Filed in Color)

(56) References Cited

OTHER PUBLICATIONS

Díaz-Flores et al., "Morphofunction, interactions and pathology in a quiescent and activated mesenchymal cell niche," *Histology and Histopathology*, 24: 909-969 (2009).

Elkin et al., "Regulation of Heparanase Gene Expression by Estrogen in Breast Cancer," *Cancer Research*, 63: 8821-8826 (2003).

Evensen et al., "Mural cell associated VEGF is required for organotypic vessel formation," *PLoS One*, 4: 1-11 (2009).

Feoktistov et al., "Mast Cell-Mediated Stimulation of Angiogenesis Cooperative Interaction Between $A_{2B}$ and $A_3$ Adenosine Receptors," *Circulation Research*, 92(5): 485-492 (2003).

Fischbach et al., "Engineering tumors with 3D scaffolds," *Nature Methods*, 4: 855-860 (2007).

Frevert et al., "Rapid fluorescence-based measurement of neutrophil migration in vitro," *Journal of Immunological Methods*, 213: 41-52 (1998).

Friedrich et al., "Spheroid-based drug screen: considerations and practical approach," *Nature Protocols*, 4: 309-324 (2009).

Hamburger et al., "Direct Cloning of Human Ovarian Carcinoma Cells in Agar," *Cancer Research*, 38: 3438-3444 (1978).

Hamburger et al., "Primary Bioassay of Human Tumor Stem Cells," *Science*, 197: 461-463 (1977).

Hanahan et al., "The Hallmarks of Cancer," *Cell*, 100: 57-70 (2000).

Herman and Leung, "Creation of human skin equivalents for the in vitro study of angiogenesis in would healing," *Methods in Molecular Biology*, 467: 241-248 (2009).

Katsoulotos, Gregory P. "The function of the signaling protein Ras guanine releasing protein 4 (RasGRP4) in human mast cells," *A thesis submitted in fulfillment of the requirements for the degree of Doctor of Philosophy*, The University of New South Wales (2006).

Koh et al., "In Vitro three dimensional collagen matrix models of endothelial lumen formation during vasculogenesis and angiogenesis," *Methods in Enzymology*, 443: 83-101 (2008).

Lee et al., "Three-dimensional culture models of normal and malignant breast epithelial cells," *Nature Methods*, 4: 359-365 (2007).

Lester et al., "Erythropoietin Promotes MCF-7 Breast Cancer Cell Migration by an ERK/Mitogen-activated Protein Kinase-dependent Pathway and Is Primarily Responsible for the Increase in Migration Observed in Hypoxia," *The Journal of Biological Chemistry*, 280(47): 39273-39277 (2005).

Liu et al., "Caveolin-1 Expression Enhances Endothelial Capillary Tubule Formation," *The Journal of Biological Chemistry*, 277(12): 10661-10668 (2002).

Lugassy and Barnhil, "Angiotropic melanoma and extravascular migratory metastasis," *Advances in Anatomic Pathology*, 14: 195-201 (2007).

Lugassy et al., "Pericyte-Like Location of GFP-Tagged Melanoma Cells," *American Journal of Pathology*, 164(4): 1191-1198 (2004).

Lugassy et al., "Pericytic-like angiotropism of glioma and melanoma cells," *The American Journal of Dermatopathology*, 24: 473-478 (2002).

Lukiw et al., "Coordinate Activation of HIF-1 and NF-κb DNA Binding and COX-2 and VEGF Expression in Retinal Cells by Hypoxia," *Investigative Ophthalmology & Visual Science*, 44(10): 4163-4170 (2003).

Lybarger et al., "Rapid Generation and Flow Cytometric Analysis of Stable GFP-Expressing Cells," *Cytometry*, 25: 211-220 (1996).

Magalhães et al., "Applications of a new in vivo tumor spheroid base shell-less chorioallantoic membrane 3-D model in bioengineering research," *Journal of Biomedical Science and Engineering*, 3: 20-26 (2010).

Mao et al., "The Cytoplasmic Domain Is Critical to the Tumor Suppressor Activity of TSLC1 in Non-Small Cell Lung Cancer," *Cancer Research*, 63: 7979-7985 (2003).

Mataraza et al., "IQGAP1 Promotes Cell Motility and Invasion," *The Journal of Biological Chemistry*, 278(42): 41237-41245 (2003).

Nisato et al., "Generation and Characterization of Telomerase-Transfected Human Lymphatic Endothelial Cells with an Extended Life Span," *American Journal of Pathology*, 165(1): 11-24 (2004).

Ojalvo et al., "Gene Expression Analysis of Macrophages That Facilitate Tumor Invasion Supports a Role for Wnt-Signaling in Mediating Their Activity in Primary Mammary Tumors," *The Journal of Immunology*, 184(2): 702-712 (2010).

Peen et al., "What you should know about PR3-ANCA Structural aspects of antibodies to proteinase 3 (PR3)," *Arthritis Research*, 2(4): 255-259 (2000).

Petersen et al., "Interaction with basement membrane serves to rapidly distinguish growth and differentiation patterns of normal and malignant human breast epithelial cells," *PNAS*, 89: 9064-9068 (1992).

Rauch et al., "Engineering angiogenesis following spinal cord injury: a coculture of neural progenitor and endothelial cells in a degradable polymer implant leads to an increase in vessel density and formation of the blood-spinal cord barrier," *European Journal of Neuroscience*, 29: 132-145 (2009).

Ritzhaupt et al., "Porcine Endogenous Retrovirus Infects but Does Not Replicate in Nonhuman Primate Primary Cells and Cell Lines," *Journal of Virology*, 76(22): 11312-11320 (2002).

Russo et al., "Structural requirements for intracellular targeting of SP-C proprotein," *Am. J. of Physiol*, 277: L1034-L1044 (1999).

Schmidt et al., "Use of Nucleofector® Technology to Establish Stably Expressing Cell Lines," pp. 1-6, 2004—available online at www.amaxa/com.

Somasiri et al., "Overexpression of the Anti-Adhesin Podocalyxin Is an Independent Predictor of Breast Cancer Progression," *Cancer Research*, 64: 5068-5073 (2004).

Stratman et al., "Pericyte recruitment during vasculogenic tube assembly stimulates endothelial basement membrane matrix formation," *Blood*, 114: 5091-5101 (2009).

Vajkoczy et al., "Glioma cell migration is associated with glioma-induced angiogenesis in vivo," *International Journal of Developmental Neuroscience*, 17: 557-563 (1999).

Wartenberg et al., "Tumor-induced angiogenesis studies in confrontation cultures of multicellular tumor spheroids and embryoid bodies grown from pluripotent embryonic stem cells," *FASEB Journal*, 15: 995-1005 (2001).

Wenger et al., "Modulation of in vitro angiogenesis in a three-dimensional spheroidal coculture model for bone tissue engineering," *Tissue Engineering*, 10: 1536-1547 (2004).

Yamamoto et al., "Cellular Dynamics Visualized in Live Cells In Vitro and In Vivo by Differential Dual-Color Nuclear-Cytoplasmic Fluorescent-Protein Expression," *Cancer Research*, 64: 4251-4256 (2004).

Yamamoto et al., "Determination of Clonality of Metastasis by Cell-Specific ColorCoded Fluorescent-Protein Imaging," *Cancer Research*, 63: 7785-7790 (2003).

Yang et al., "Dual-color fluorescence imaging distinguishes tumor cells from induced host angiogenic vessels and stromal cells," *PNAS*, 100(24): 14259-14262 (2003).

Zhang et al., "p21-activated kinase 4 interacts with integrin αvβ5-mediated cell migration," *The Journal of Cell Biology*, 158(7): 1287-1297 (2002).

Zhou et al., "Tumor endothelial cell tube formation model for determining antiangiogenic activity of a tRNA synthetase cytokine," *Methods*, 44: 190-195 (2008).

Zijlstra et al., "The inhibition of tumor cell intravasation and subsequent metastasis via regulation of in vivo tumor cell motility by the tetraspanin CD151," *Cancer Cell*, 13: 221-234 (2008).

Zhang, "A new co-culture model of breast cancer-cell lines labeled by green fluorescent proteins," *A thesis submitted in fulfillment of the requirements for the degree of Master of Science*, Texas Tech University (2001).

\* cited by examiner

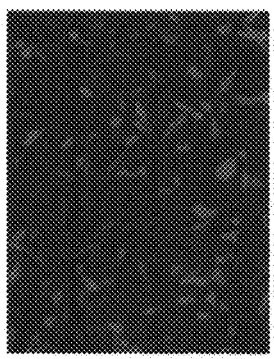
Fig.1A PAE GFP
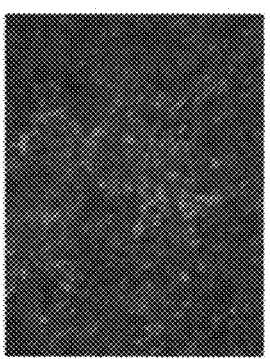
Fig.1B PAE YFP
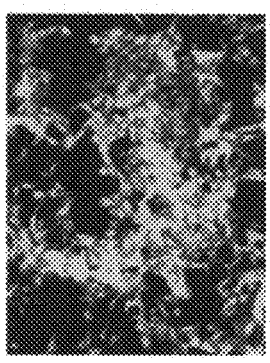
Fig.1C PAE RFP
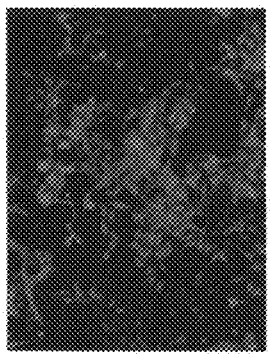
Fig.1D PAE CFP

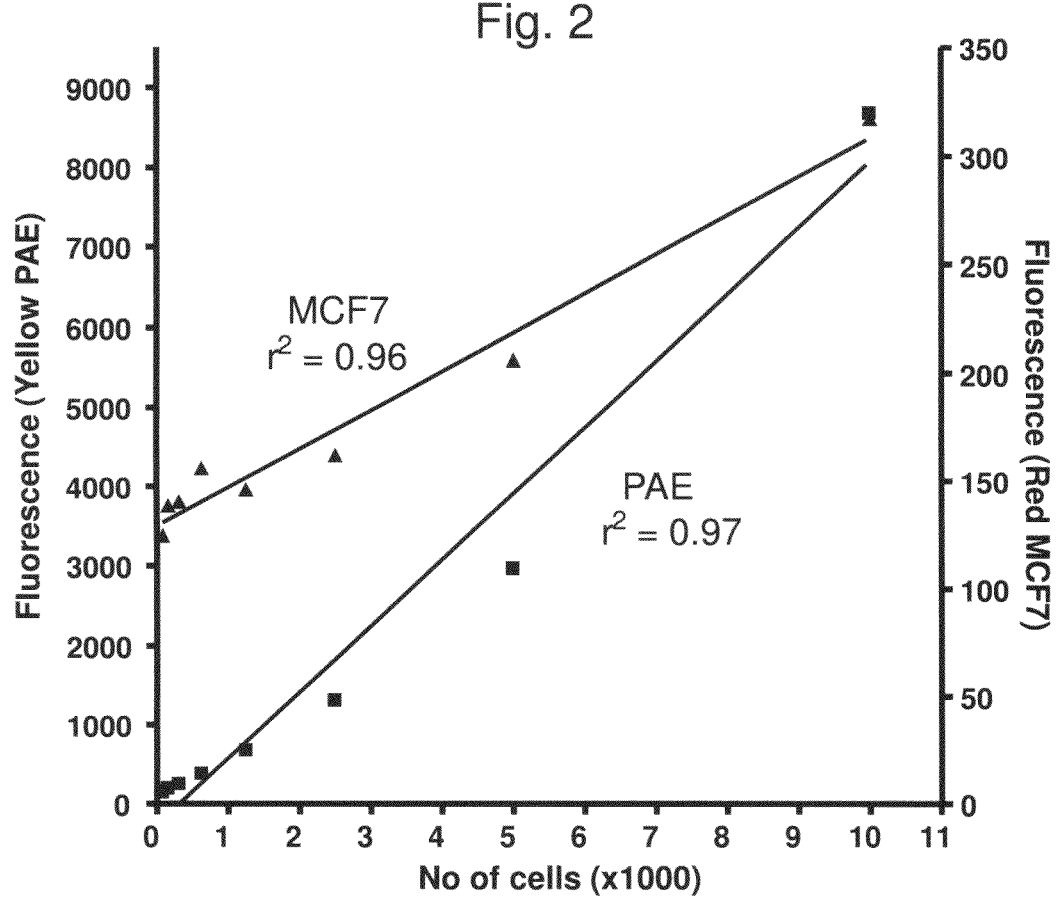

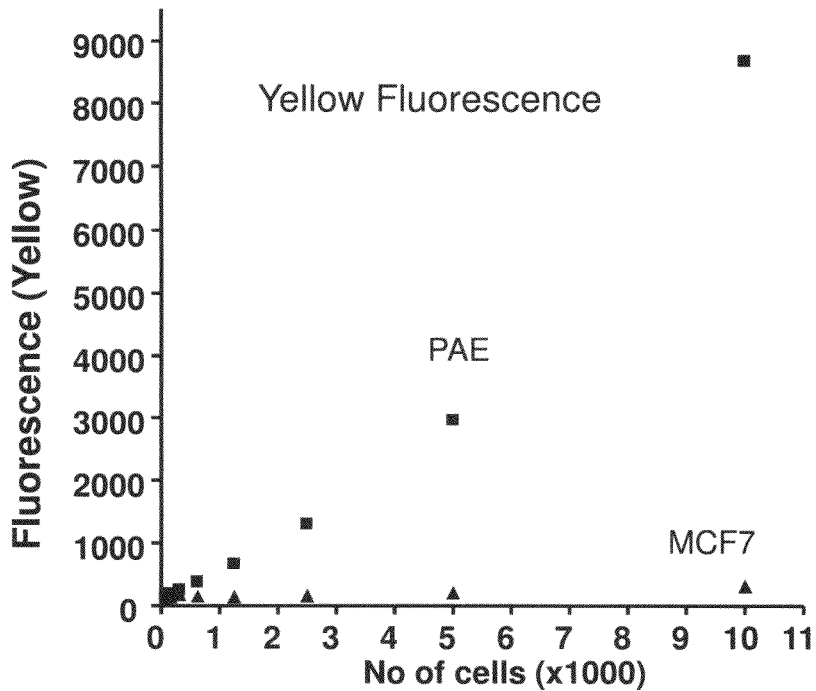
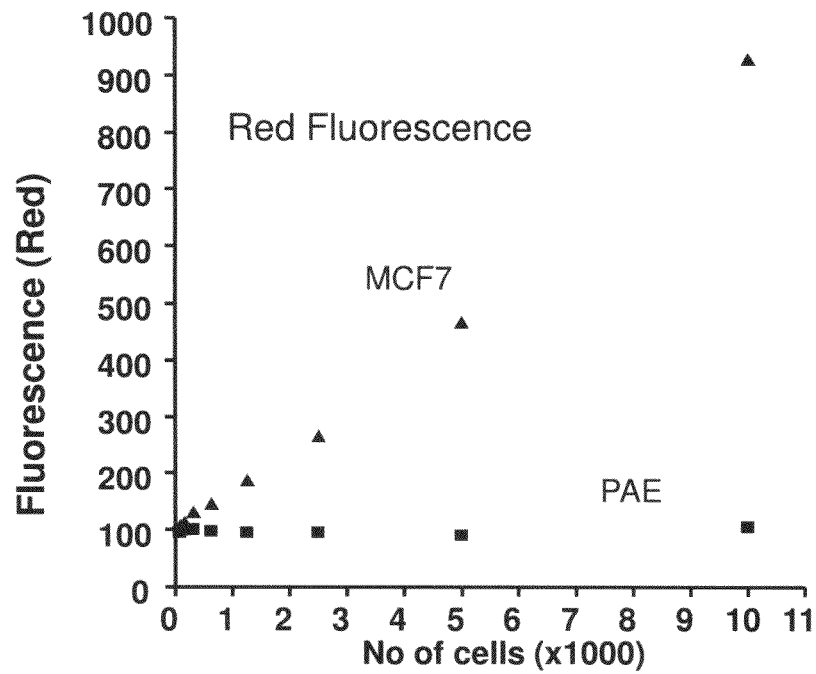

Fig. 7A
0 µg Suramine
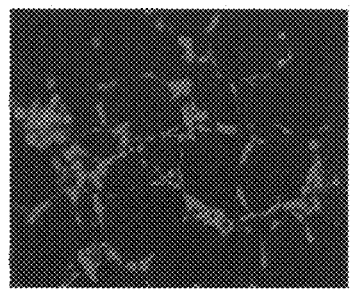
18 µg Suramine
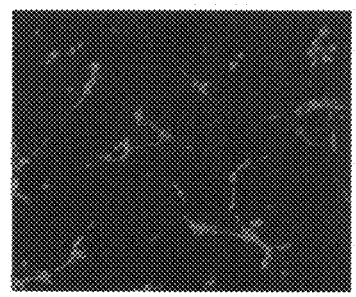
30 µg Suramine
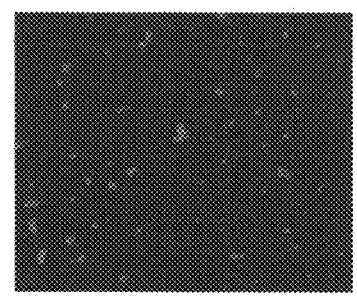

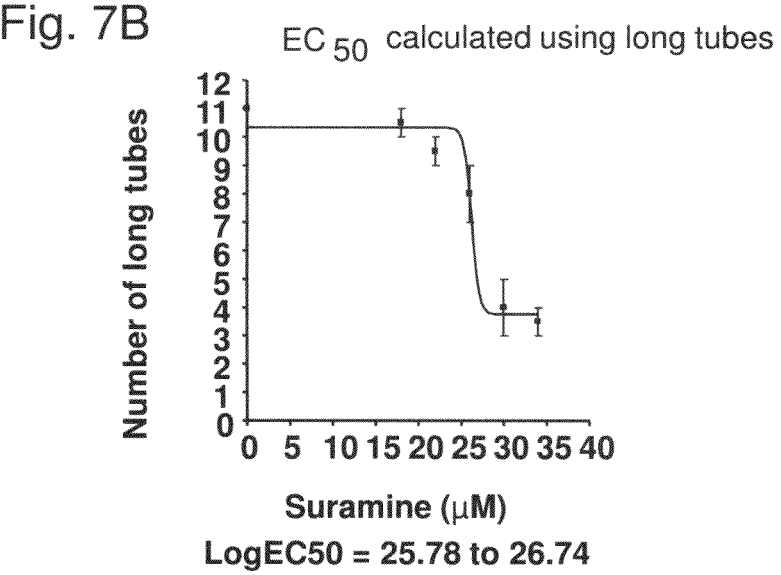
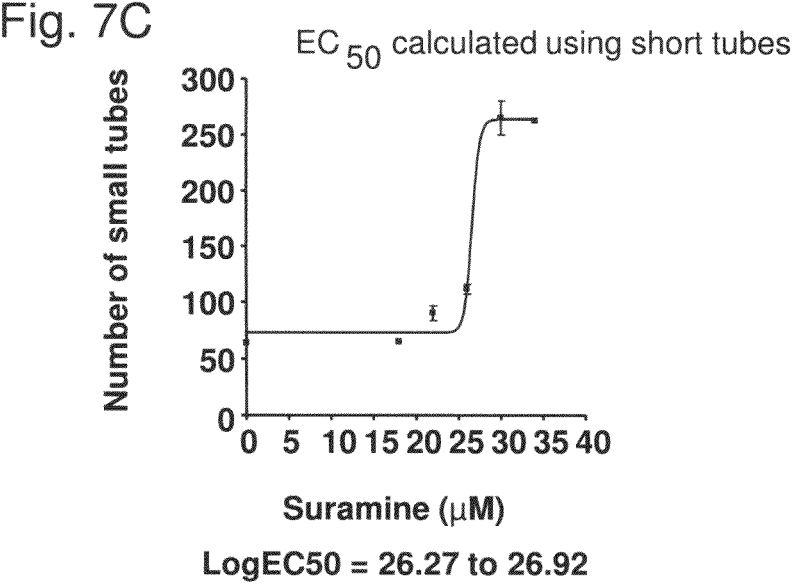

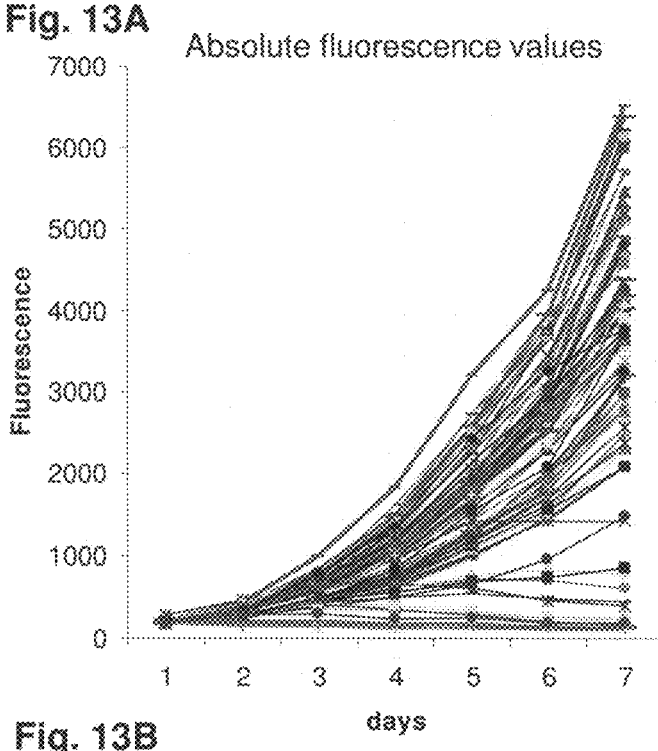
Fig. 13A Absolute fluorescence values
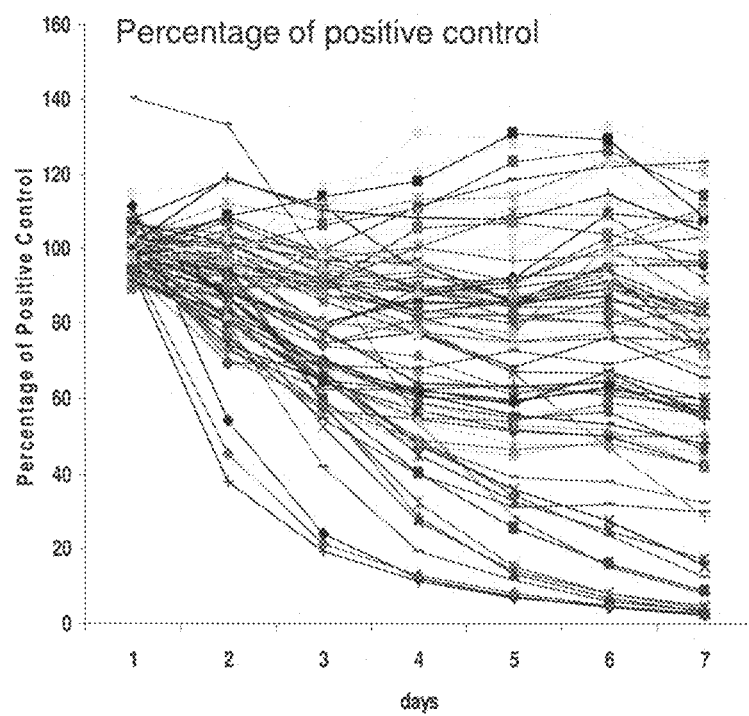
Fig. 13B Percentage of positive control The In Concert Cell Players of Angiogenesis Involved in the Tumor Microenvironment Diagram of Endothelial Cell Growth Assays

Fig. 22

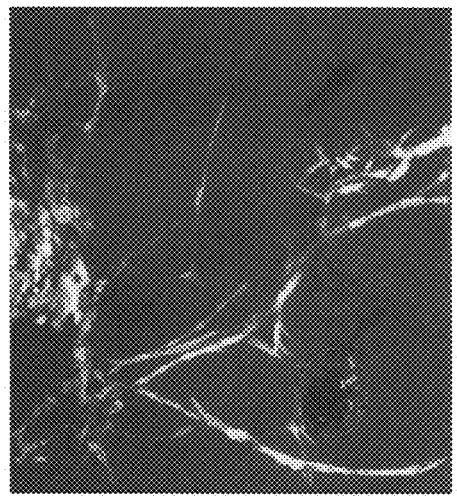
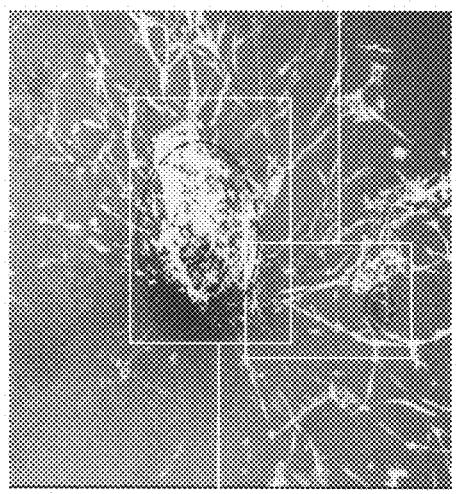
Fig. 25

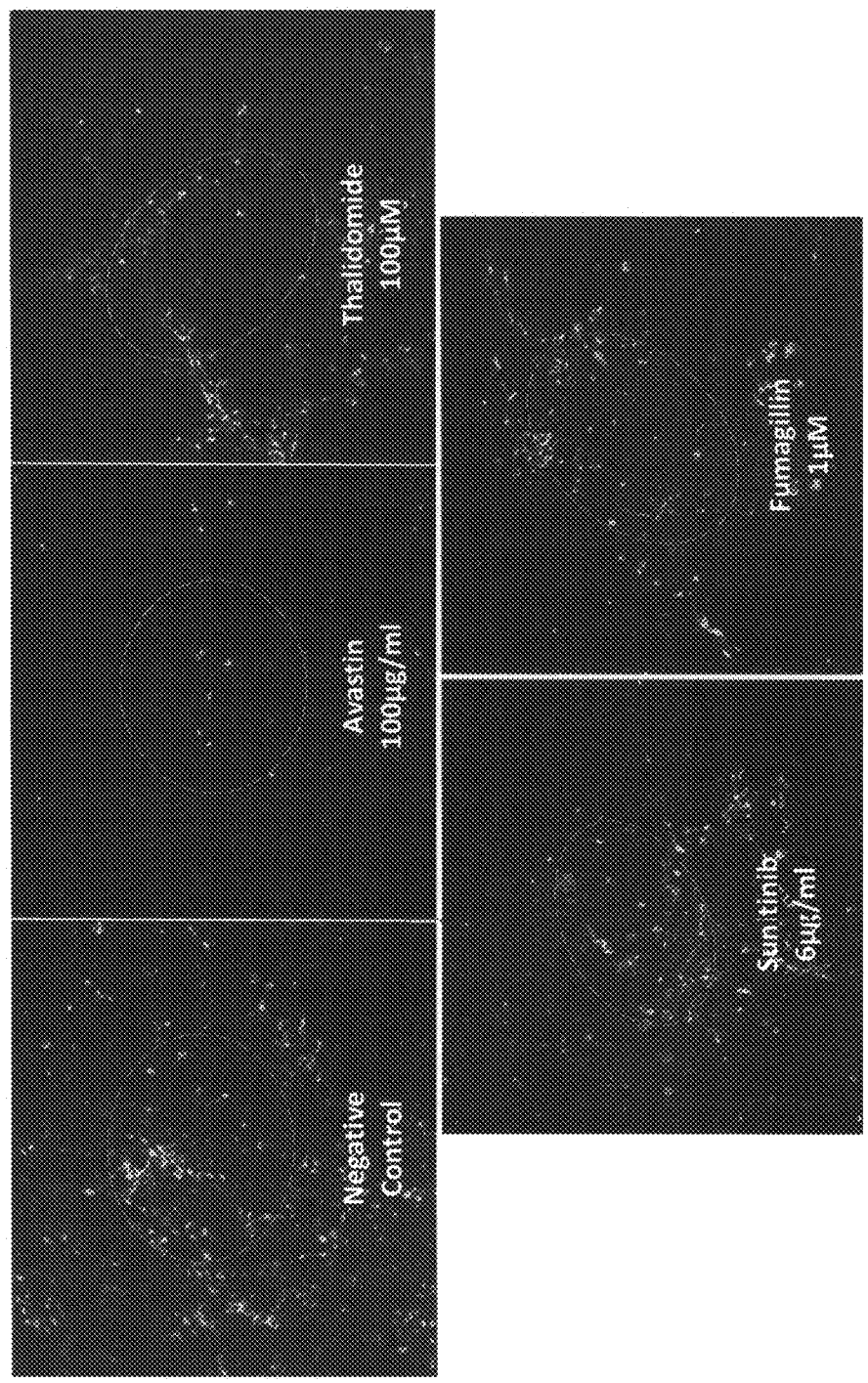

METHODS OF MONITORING ANGIOGENESIS AND METASTASIS IN THREE DIMENSIONAL CO-CULTURES

CROSS REFERENCE TO RELATED APPLICATION

This is a continuation-in-part of U.S. application Ser. No. 12/060,752, filed Apr. 1, 2008 now abandoned, which claims the benefit of U.S. Provisional Application No. 60/976,732, filed Oct. 1, 2007. The prior applications are incorporated herein by reference in their entirety.

FIELD OF THE DISCLOSURE

This disclosure relates to fluorescent cell lines and to the use of such cell lines in monitoring cellular activity, such as angiogenesis, as well as their use in three-dimensional cell cultures, for instance to monitor angiogenic and metastatic potential of tumor cells. Also described are methods of using such cells in selecting personalized therapeutics.

BACKGROUND

Biological processes occurring in any organism involve the interaction of multiple cell types, biologically relevant factors, and the organism's environment. Some of the fundamental questions remaining in biology are related to understanding how the different cells within organisms communicate and organize to form an individual. One frequently studied system in which multiple cell types function together and influence each other is angiogenesis.

Angiogenesis is a biological process of generating new blood vessels from pre-existing blood vessels into a tissue or organ. Angiogenesis has been intensively studied over the past several decades because of its fundamental importance in tissue development, vascular diseases, and cancer. Under normal physiological conditions, humans or animals undergo angiogenesis only in very specific restricted situations. For example, angiogenesis is normally observed in fetal and embryonal development and formation of the corpus luteum. Post-natal angiogenesis is an important physiological function in the ovary, endometrium, placenta, and in wound healing.

New vessel growth is tightly controlled by many angiogenic regulators (see for example Folkman, J., Nature Med., 1: 27-31, 1995a), and the switch of the angiogenesis phenotype depends on the net balance between up-regulation of angiogenic stimulators and down-regulation of angiogenic suppressors. Pathological deregulation of angiogenesis is a prominent feature of a number of human diseases, including atherogenesis, arthritis, psoriasis, corneal neovascularization, diabetic retinopathy, rheumatoid arthritis, and cancer, for example during malignant transformation that facilitates tumor growth and metastasis.

In cancer, tumors induce angiogenesis by secreting various growth factors, such as vascular endothelial growth factor (VEGF), and basic fibroblast growth factor (bFGF) among others. Growth factors, such as bFGF and VEGF, can induce capillary growth into the tumor, which is thought to drive tumor expansion by supplying the tumor with nutrients and/or removing the cellular waste.

Angiogenesis is also an element of metastasis of a tumor. Single cancer cells can break away from an established solid tumor, enter the blood vessel, and be carried to a distant site, where they can implant and begin the growth of a secondary tumor. It has even been suggested that the blood vessels in a solid tumor may in fact be mosaic vessels, comprised of both endothelial cells and tumor cells. Such mosaicity allows for substantial shedding of tumor cells into the vasculature.

Angiogenesis-based anti-tumor therapies typically use natural and synthetic angiogenesis inhibitors such as angiostatin, endostatin and tumstatin. Recently the Food and Drug Administration (FDA) approved an antibody therapy targeting angiogenesis in colorectal cancer. This therapy is based on a monoclonal antibody directed against an isoform of VEGF and is marketed under the trade name Avastin®. While established anti-angiogenesis therapies are promising, the need still exists for the development of additional modulators of angiogenesis.

SUMMARY OF THE DISCLOSURE

This disclosure relates to an in vitro assay for use in assessing the cellular activity of cell lines. The assay disclosed herein uses detectable cell lines from an array of different cell lines, such as cell lines of different cell types and/or anatomical origins, such that the effects and interdependency of the different cell lines can be monitored simultaneously, for example in real-time multiplex assays. In some examples, the assay uses multiple different cell lines that contribute to angiogenesis in vivo, such that the angiogenesis process can be recapitulated in vitro.

In some embodiments, the disclosed assay uses mammalian cell lines that have been stably transfected with mammalian expression vectors which include nucleic acid sequences encoding proteins that can be detected by light emitted by the proteins expressed from the expression vectors, for example a fluorescent protein expressed from the expression vectors.

In some of the disclosed embodiments, the in vitro assay is a multiplex assay method for evaluating cellular activity, in which a culture is provided that contains one or more different isolated mammalian cell lines (such as histologically different cell lines) that stably and constitutively express fluorescent proteins having different emission spectra, for example the different fluorescent proteins have different wavelengths of emission maxima, such that the emission spectra from the different fluorescent proteins is distinguishable. The culture is assessed for cellular activity by quantifying fluorescence or detecting a pattern of fluorescence from fluorescent proteins present in the culture. In some examples, a culture of two different isolated mammalian cell lines (such as histologically different cell lines) that stably and constitutively express fluorescent proteins having different emission spectra is provided and the cellular activity of one or both of the fluorescent cell lines present in the culture is assessed by quantifying fluorescence or detecting a pattern of fluorescence from fluorescent proteins present in the culture. By extension, the cellular activity of cell lines present in culture of three, four, five or even more isolated cell lines expressing fluorescent proteins with different emission spectra can be assessed by quantifying fluorescence or detecting a pattern of fluorescence from the fluorescent proteins present in the culture.

In some embodiments, the cellular activity of the cell line(s) present in the culture is assessed by determining one or more of the growth rate, migration potential, cell death or tubule formation potential of the cell lines using the quantified fluorescence or pattern of fluorescence from the fluorescent proteins present in the culture. Such assays can be used to measure cellular activity and interaction within complex biological systems. Such measurements of cellular activity can even be obtained and/or measured in a temporal sequence or in real-time as they occur.

In some embodiments, the disclosed in vitro assay is used to determine the effects of an exogenous agent, such as a test agent (for example a potential modulator of angiogenesis, such as a potential inhibitor of angiogenesis or a potential stimulator of angiogenesis), growth factor, biological sample (such as a patient sample), another cell line (such as one or more fluorescent cell lines) etc. on the cellular activity of a fluorescent cell line. Such an assay can be used to screen for modulators of angiogenesis, for example to identify angiogenesis inhibitors useful in the treatment of cancer.

Also disclosed are cell lines have been stably transfected with mammalian expression plasmids that constitutively express different fluorescent proteins, for example green fluorescent protein and related florescent proteins, such as yellow fluorescent protein, red fluorescent protein, cyan fluorescent protein and the like. These cell lines are particularly suited for use in the disclosed methods. Kits for performing the disclosed assays, which include the disclosed fluorescent cell lines, are also disclosed.

This disclosure also relates to methods for monitoring angiogenic or metastatic potential of tumor cells comprising preparing a three-dimensional co-culture that is comprised of three layers. The first layer comprises a neutral polysaccharide polymer gel in contact with the bottom of the culture dish. The second layer is on top of the first layer and comprises a solidified gel matrix, endothelial cells that are dispersed in the solidified gel matrix; and tumor cells comprising either a tumor spheroid colony or a sample of a tumor biopsy, and which are also suspended in the solidified gel matrix, and a third layer comprising culture medium. Angiogenic or metastatic potential of tumor cells is monitored by incubating the three-dimensional co-culture; and detecting at least one of endothelial cell proliferation, endothelial cell tubule formation or tumor cell angiotropism of the cells in the second layer. In particular examples of these methods, the first, second, or third layer further comprises at least one test agent, which in some embodiments is a known or potential inhibitor of angiogenesis or metastasis or augmenter of these processes.

Also disclosed herein are methods of selecting a personalized anti-angiogenic or anti-metastatic treatment for cancer in a subject comprising preparing multiple three-dimensional co-cultures, each co-culture comprising a first layer comprising a neutral polysaccharide polymer gel in contact with the bottom of a culture dish; a second layer on top of the first layer, comprising: a solidified gel matrix; endothelial cells dispersed in the solidified gel matrix; and tumor cells comprising either a tumor spheroid colony or a sample of a tumor biopsy, suspended in the solidified gel matrix; and a third layer comprising culture medium, wherein all but one of the co-cultures further comprises at least one test agent comprising an anti-angiogenic or anti-metastatic compound in the first, second, or third layers. A personalized anti-angiogenic or anti-metastatic treatment for cancer in a subject is selected by incubating the three-dimensional co-cultures; detecting at least one of endothelial cell proliferation, endothelial cell tubule formation or tumor cell angiotropism of the cells in the second layer; and selecting the at least one test agent having the greatest effect on at least one of endothelial cell proliferation, endothelial cell tubule formation or tumor cell angiotropism in comparison to endothelial cell proliferation, endothelial cell tubule formation or tumor cell angiotropism in the cells of the co-culture without the test agent.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 1A is a digital image of porcine aortic endothelial (PAE) cells that stably express green fluorescent protein (GFP). FIG. 1B is a digital image of PAE cells that stably express yellow fluorescent protein (YFP). FIG. 1C is a digital image of PAE cells that stably express red fluorescent protein (RFP). FIG. 1D is a digital image of PAE cells that stably express cyan fluorescent protein (CFP).

FIG. 2 as a graph of fluorescence versus cell number showing linearity of fluorescence versus cell number in mono-cultures of PAE endothelial cells that stably express YFP and mono-cultures of human breast adenocarcinoma cell line MCF7 that stably express RFP.

FIG. 3A is a graph of fluorescence versus cell number showing that precise gated fluorescence emission and excitation on YFP allows discrimination of YFP expressing cells (PAE) from RFP expressing cells (MCF7) in co-cultures. FIG. 3B is a graph of fluorescence versus cell number showing that precise gated fluorescence emission and excitation on RFP allows discrimination of RFP expressing cells (MCF7) from YFP expressing cells (PAE) in co-cultures.

FIG. 7A is a set of digital images showing the tubules formed in cultures of PAE endothelial cells at various suramin concentrations. FIG. 7B is a graph of the number of long tubules formed by GFP expressing PAE cells as a function of suramin concentration. FIG. 7C is a graph of the number of short tubules formed by GFP expressing PAE cells as a function of suramin concentration.

FIG. 13A is a graph of cell growth (measured as absolute fluorescence) as a function of time for the wells shown in FIG. 12. FIG. 13B is a graph of cell growth (normalized for the growth rate of the positive control) as a function of time for the wells shown in FIG. 12.

FIG. 22 is a series of photomicrographs of 2D co-cultures of endothelial cells (PAE) and indicated tumor cell lines. PAE cells were grown on top of matrigel layered on top of a layer of the indicated tumor cell line. PAE seeding density was approximately 18,000 cells/well. Cultures were incubated for six hours.

FIG. 25 is a series of confocal photomicrographs of 3D co-cultures of HMEC-1 endothelial cells (yellow) and MCF-7 tumor xenografts (dashed blue ellipse). Left and right panels are magnified 10×. Middle panel is magnified 5×. Endothelial cells (about 21,000/well) were mixed with single ringlet of xenograft core biopsy in molten matrigel that was allowed to solidify on top of agarose-coated 96 well plates.

FIG. 31 shows a series of confocal photomicrographs of five-day 3D co-cultures of HMEC-1 (yellow) and human leiomyosarcoma HTB-88 core biopsy xenograft (blue dashed ellipses). Peripheral ringlet xenograft tissue/HMEC-1 co-cultures were incubated with Avastin®, Thalidomide, Sunitinib or Fumagilin.

DETAILED DESCRIPTION OF SEVERAL EMBODIMENTS

I. Abbreviations

Figure 4A:
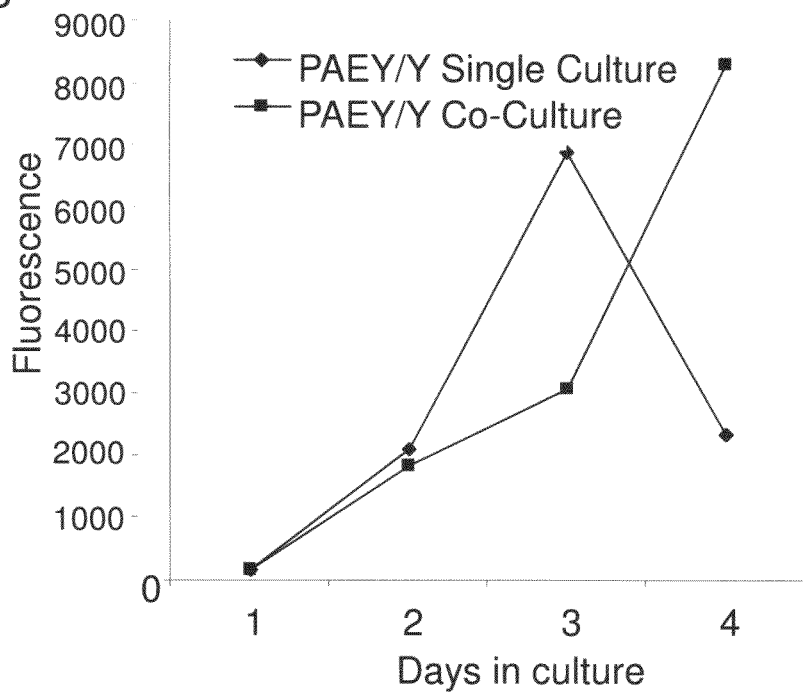
FIG. 4A is a graph of growth curves for PAE endothelial cells expressing YFP in mono-culture or in co-culture with MCF7 breast cancer cells.

2D: two-dimensional
3D: three-dimensional
ATCC: American Type Culture Collection
bFGF: basic fibroblast growth factor
BEC: brain endothelial cells
BME: Basement Membrane Extract
DMSO: dimethyl sulfoxide
EC50: The term half maximal effective concentration
EBM-2: endothelial basal medium-2
FBS: fetal bovine serum
FDA: Food and Drug Administration
GFP: green fluorescent protein.
HMEC-1: human microvascular endothelial cell
IPF: Idiopathic Pulmonary Fibrosis
LEC: lymphatic endothelial cells
PAE: porcine aortic endothelial cells
PBS: phosphate buffered saline
RFP: red fluorescent protein
VEGF: endothelial growth factor
YFP: yellow fluorescent protein II. Terms Unless otherwise noted, technical terms are used according to conventional usage. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

To facilitate review of the various embodiments of the disclosure, the following explanations of specific terms are provided:

Animal: A living multi-cellular vertebrate organism, a category that includes, for example, mammals and birds. The term mammal includes both human and non-human mammals. Similarly, the term "subject" includes both human and veterinary subjects, for example, humans, non-human primates, dogs, cats, horses, pigs, rats, mice, and cows.

Angiogenesis: A biological process leading to the generation of new blood vessels through sprouting and/or growth from pre-existing blood vessels. The process can involve the migration and proliferation of endothelial cells from preexisting vessels. Angiogenesis occurs during pre-natal development, post-natal development, and in the adult. In the adult, angiogenesis occurs during the normal cycle of the female reproductive system, wound healing, and during pathological processes such as cancer (for a review see Battegay, *J. Molec. Med.* 73(7): 333-346, 1995).

Angiogenic activity: The ability of an agent to promote or inhibit angiogenesis. Angiogenic activity can be measured in an angiogenesis assay, for example using the fluorescent cell lines and assays disclosed herein.

Angiogenic factor: A molecule that affects angiogenesis, for example by stimulating or inhibiting angiogenesis. Numerous experiments have suggested that tissues secrete factors that promote angiogenesis under conditions of poor blood supply during normal and pathological angiogenesis processes. The formation of blood vessels is initiated and maintained by a variety of factors secreted either by a cell (such as a tumor cell) or by accessory cells. Many different growth factors and cytokines have been shown to exert chemotactic, mitogenic, modulatory or inhibitory activities on endothelial cells, smooth muscle cell and fibroblasts and can, therefore, be expected to participate in an angiogenic process. For example, factors modulating growth, chemotactic behavior and/or functional activities of vascular endothelial cells include aFGF, bFGF, angiogenin, angiotropin, epithelial growth factor, IL-8, and vascular endothelial growth factor (VEGF) among others.

Because many angiogenic factors are mitogenic and chemotactic for endothelial cells, their biological activities (such as angiogenic activities) can be determined in vitro by measuring the induced migration of endothelial cells or the effect of these factors on endothelial cell proliferation using the cell lines assays and methods disclosed herein. For example, migration assays and other assays, such as tubule formation assays and growth assays can also be used to determine angiogenic activity, for example the angiogenic activity in the presence of a test agent, such as a potential angiogenesis inhibitor.

Angiogenic potential: The ability of a factor, such as a compound or cell type, such as a tumor cell, to stimulate angiogenesis in an endothelial cell line.

Angiotropism: The movement of a tumor cell along a vascular highway. Such movement is a hallmark of metastasis of a tumor. In particular examples, angiotropism is observable as the migration of tumor cells in vitro along endothelial tubules.

Biological sample: A sample obtained from a plant or animal subject about which information is desired, for example, information about the samples ability to promote cellular growth, tubule formation, and/or cellular migration. As used herein, biological samples include all clinical samples, including, but not limited to, cells, tissues, and bodily fluids, such as: blood; derivatives and fractions of blood, such as serum, and lymphocytes (such as B cells, T cell, and subfractions thereof); extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; middle ear fluids, bronchoalveolar levage, tracheal aspirates, sputum, nasopharyngeal aspirates, oropharyngeal aspirates, or saliva. In particular embodiments, the biological sample is obtained from an animal subject, such as in the form of middle ear fluids, bronchoalveolar levage, tracheal aspirates, sputum, nasopharyngeal aspirates, oropharyngeal aspirates, or saliva. In particular embodiments, the biological sample is obtained from a subject, such as blood or serum. In other embodiments, the biological sample is a sample of tissue removed from a tumor (e.g., a tumor biopsy). A patient sample is a sample obtained from a subject, such as a mammalian subject, for example a human subject under medical care.

Cellular activity: The activity of a particular cell line, such as the ability of the cell to divide, migrate in response to stimulus, or to form three dimensional structures, such as tubules. The cellular activity of a particular cell line can be assessed using in vitro assays, for example the assays disclosed herein.

Cancer: A malignant disease characterized by the abnormal growth and differentiation of cells. "Metastatic disease" refers to cancer cells that have left the original tumor site and migrate to other parts of the body for example via the bloodstream or lymph system.

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia, and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (such as adenocarcinoma), lung cancers, gynecological cancers (such as, cancers of the uterus (e.g., endometrial carcinoma), cervix (e.g., cervical carcinoma, pre-tumor cervical dysplasia), ovaries (e.g., ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (e.g., squamous cell carcinoma, intraepithelial carcinoma, adenocarcinoma, fibrosarcoma, melanoma), vagina (e.g., clear cell carcinoma, squamous cell carcinoma, botryoid sarcoma), embryonal rhabdomyosarcoma, and fallopian tubules (e.g., carcinoma)), prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma), and skin cancer (such as melanoma and nonmelanoma).

Cell culture: The process by which either prokaryotic or eukaryotic cells are grown under controlled conditions. In practice the term "cell culture" has come to refer to the culturing of cells derived from multicellular eukaryotes, especially animal cells, such as mammalian cells, for example the fluorescent cells disclosed herein. Mammalian cells are grown and maintained at an appropriate temperature and gas mixture (typically, 37° C., 5% $CO_2$) in a cell incubator. Culture conditions vary widely for each cell type, and variation of conditions for a particular cell type can result in different phenotypes being expressed. Aside from temperature and gas mixture, the most commonly varied factor in culture systems is the growth medium. Recipes for growth media can vary in pH, glucose concentration, growth factors, and the presence of other nutrient components. The growth factors used to supplement media are often derived from animal blood, such as calf serum.

Some cells naturally live without attaching to a surface, such as cells that exist in the bloodstream. Others require a surface, such as most cells derived from solid tissues. Cells grown unattached to a surface are referred to as suspension cultures. Other adherent cultures cells can be grown on tissue culture plastic, which may be coated with extracellular matrix components (for example collagen or fibronectin) to increase its adhesion properties and provide other signals needed for growth. Co-culture refers to the culture of more than one cell line (such as more than one of the disclosed cell lines), more than one cell type, or a cell line and a tissue sample, such a sample of a tumor biopsy, in a single vessel. A 2-Dimensional (2D) co-culture is a co-culture wherein the different cell lines or cell types are not cultured within the same dimension or layer of the culture, and are separated for example, by a gelled layer of gel matrix. A 3-Dimensional (3D) co-culture is a co-culture wherein the different cell lines or cell types are cultured together within a three-dimensional gel matrix.

Chemical stimulus: A chemical signal that stimulates an activity of a cell, or cell line, for example the cell lines disclosed herein. Examples of chemical stimuli include growth factors, such as bFGF and VEGF.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an angiogenesis inhibitor. Chemotherapeutic agents are described for example in Slapak and Kufe, *Principles of Cancer Therapy*, Chapter 86 in Harrison's Principles of Internal Medicine, 14th edition; Perry et al., Chemotherapy, Ch. 17 in Abeloff, *Clinical Oncology* 2nd ed., 2000 Churchill Livingstone, Inc; Baltzer and Berkery. (eds): *Oncology Pocket Guide to Chemotherapy,* 2nd ed. St. Louis, Mosby-Year Book, 1995; Fischer Knobf, and Durivage (eds): *The Cancer Chemotherapy Handbook,* 4th ed. St. Louis, Mosby-Year Book, 1993. Combination chemotherapy is the administration of more than one agent to treat cancer, for example an alkylating agent and an angiogenesis inhibitor.

Contacting: The placement in direct physical association, including both in solid and in liquid form. Contacting can occur in vivo, for example by administering an agent to a subject, or in vitro for example with isolated cells or cell-cultures, for example cell-cultures of the disclosed fluorescent cell lines. "Administrating" to a subject includes topical, parenteral, oral, intravenous, intra-muscular, sub-cutaneous, inhalational, nasal, or intra-articular administration, among others.

Control: A reference standard. A control can be a known value indicative of basal cellular activity, such as basal migratory potential, doubling time, tubule formation potential and the like, or a control cell-culture, such as a culture including at least one of the disclosed fluorescent cell lines, not treated with an exogenous agent, such as a test agent, one or more cell lines (such as the fluorescent cell lines disclosed herein), angiogenic factor, angiogenic inhibitor, or the like. A difference between a test sample and a control can be an increase or conversely a decrease. The difference can be a qualitative difference or a quantitative difference, for example a statistically significant difference. In some examples, a difference is an increase or decrease, relative to a control, of at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater then 500%.

Disperse: Distribute throughout a medium, such as a gel matrix of the disclosed 3D co-cultures. In particular examples, cells that are dispersed in a medium are distributed evenly throughout the medium. However, dispersal of cells in a medium does not require absolute even distribution of cells.

EC50: The term half maximal effective concentration (EC50) refers to the concentration of a drug which induces a response halfway between the baseline and maximum. EC50 is commonly used as a measure of drug potency.

Encoding: Unless evident from its context, includes nucleic acid sequences, such as RNA and DNA sequences, that encode a polypeptide, as well as RNA and DNA sequences that are transcribed into proteins, such as fluorescent proteins, for example nucleic acid sequences that encode green fluorescent protein, red fluorescent protein, yellow fluorescent protein, cyan fluorescent protein and the like.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity. Lasers are capable of emitting light at a particular wavelength (or across a relatively narrow range of wavelengths), for example such that energy from the laser can excite one fluorophore with a specific excitation wavelength but not excite a second fluorophore with a specific excitation wavelength difference and distinct from the excitation wavelength on the first fluorophore.

Emission or emission signal: The light of a particular wavelength generated from a source. In particular examples, an emission signal is emitted from a fluorophore, such as a fluorescent protein, after the fluorophore absorbs light at its excitation wavelength(s).

Excitation or excitation signal: The light of a particular wavelength necessary and/or sufficient to excite an electron transition to a higher energy level. In particular examples, an excitation is the light of a particular wavelength necessary and/or sufficient to excite a fluorophore, such as a fluorescent protein, to a state such that the fluorophore will emit a different (such as a longer) wavelength of light then the wavelength of light from the excitation signal.

Exogenous agent: An exogenous agent is any agent external to a target cell line(s) that is to be studied, and it includes small molecules, proteins, biological samples (such as patient samples) and other cells or cell lines, such as fluorescent cell lines other than the target cell line, for example a different type of cell that can by identified as different by a distinguishable fluorescent signal. In particular examples, the exogenous agent is a test agent such as a small molecule, protein or nucleic acid, but which is not a cell or tissue sample.

Expression: With respect to a gene sequence, refers to transcription of the gene and, as appropriate, translation of the resulting mRNA transcript to a protein. Thus, expression of a protein coding sequence, such as the expression of a fluorescent protein, results from transcription and translation of the coding sequence for that protein. Constitutive expression refers to the expression of a gene product, such as a protein, for example a fluorescent protein, in a substantial continuous manner, such that the expression is not interrupted. An example of constitutive expression is continuous expression in the absence of an exogenous stimulating agent, such as an agent used to activate a promoter. Stable expression refers to expression that is not lost or reduced substantially over time, for example expression that does not diminish through multiple passages of a cell line, for example a cell line constitutively expressing a fluorescent protein.

Expression control sequences: Nucleic acid sequences that regulate the expression of a heterologous nucleic acid sequence to which it is operatively connected. Expression control sequences are operatively connected to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter; the SV40 viral promoter; the CMV promoter and the like) can be used. Promoters produced by recombinant DNA or synthetic techniques may also be used to provide for transcription of the nucleic acid sequences, for example when incorporated into a vector, such as a mammalian expression vector.

Fluorescent property: A characteristic of a fluorescent molecule, such as a fluorescent protein, for example green fluorescent protein, red fluorescent protein, yellow fluorescent protein, cyan fluorescent protein and the like. Examples of fluorescent properties include the molar extinction coefficient at an appropriate excitation wavelength, the fluorescence quantum efficiency, the shape of the excitation spectrum or emission spectrum (the "fluorescence spectrum," the excitation wavelength maximum and emission wavelength maximum, the ratio of excitation amplitudes at two different wavelengths, the ratio of emission amplitudes at two different wavelengths, the excited state lifetime, or the fluorescence anisotropy. Quantifying fluorescence refers to the determination of the amount of fluorescence generated by a fluorophore, for example a fluorescent protein, which can be the quantity of photons emitted by a fluorophore. In some examples, fluorescence is quantified by measuring the intensity of a fluorescence signal at a particular wavelength, for example the wavelength of the emission maxima of a particular fluorophore, such as a fluorescent protein. Fluorescence intensity can also be quantified at a wavelength that is not the emission maxima of a particular fluorophore, for example to avoid emission spectra that overlap and thereby interfere with the emission maxima of a particular fluorophore, such as a particular fluorescent protein. In some examples, a fluorescence signal is emitted by a population of fluorescent proteins, for example fluorescent proteins present in a population of cells containing such fluorescent proteins. Such a signal can be quantified, for example to determine the number, or relative number of cells that emit such a fluorescent signal. Detecting a pattern of fluorescence refers to the correlation of a fluorescent signal to a specific location to determine the location where a fluorescence signal, such as a fluorescent signal of a particular wavelength, originates. In some examples, a pattern of fluorescence determines the location and or shape of the cells that emit a fluorescence signal, such as cells containing a fluorescent protein, for example to determine the number of the total area of the tubules, the total number of tubules, number of nodes, number of branch points, the number of tubes per node, or node area formed by such cells using the methods disclosed herein.

Fluorescent protein: A protein capable of emission of a detectable fluorescent signal. Fluorescent proteins can be characterized by the wavelength of their emission spectrum. For example green fluorescent protein (GFP) has a fluorescent emission spectrum in the green part of the visible spectrum. In addition to green-fluorescent proteins, fluorescent proteins are known which fluoresce in other regions of the visible spectrum, for example blue-fluorescent proteins, cyan-fluorescent proteins, yellow-fluorescent proteins, orange-fluorescent proteins, red-fluorescent proteins, and far-red fluorescent proteins. Examples of fluorescent proteins can be found in the following patent documents: U.S. Pat. Nos. 5,804,387; 6,090,919; 6,096,865; 6,054,321; 5,625,048;

5,874,304; 5,777,079; 5,968,750; 6,020,192; 6,146,826; 6,969,597; 7,150,979; 7,157,565; and 7,166,444; and published international patent applications WO 07/085,923; WO 07/052,102, WO 04/058973, WO 04/044203, WO 03/062270; and WO 99/64592. Additional examples of fluorescent proteins are available from Clontech, Laboratories, Inc. (Mountain View, Calif.) under the trade name Living Colors®. Nucleic acids encoding such fluorescent proteins can be incorporated into mammalian expression vectors for use in producing the disclosed fluorescent cell lines.

Gel Matrix: A semi-solid cell culture media that is derived from extracellular matrix proteins or any suitable equivalent synthetic gel product. Gel matrices are fluid at 4° C. and gel at 37° C. In particular examples a gel matrix is a commercially available medium such as BD Matrigel™ Matrix (BD Bioscience), Cultrex® BME (Trevigen), or Geltrex® (Invitrogen®). Other basement membrane extracts that can function as a support matrix scaffolding include human placenta-derived BME (Vivo Biosciences, Inc) and synthetic BME (available from Glycosan Biosystems).

Gene: A nucleic acid sequence that encodes a polypeptide under the control of a regulatory sequence, such as a promoter or operator. A gene includes an open reading frame encoding a polypeptide of the present disclosure, as well as exon and (optionally) intron sequences. An intron is a DNA sequence present in a given gene that is not translated into protein and is generally found between exons. The coding sequence of the gene is the portion transcribed and translated into a polypeptide (in vivo, in vitro or in situ) when placed under the control of an appropriate regulatory sequence. The boundaries of the coding sequence can be determined by a start codon at the 5' (amino) terminus and a stop codon at the 3' (carboxyl) terminus. If the coding sequence is intended to be expressed in a eukaryotic cell, a polyadenylation signal and transcription termination sequence can be included 3' to the coding sequence.

Transcriptional and translational control sequences include, but are not limited to, DNA regulatory sequences such as promoters, enhancers, and terminators that provide for the expression of the coding sequence, such as expression in a host cell. A polyadenylation signal is an exemplary eukaryotic control sequence. A promoter is a regulatory region capable of binding RNA polymerase and initiating transcription of a downstream (3' direction) coding sequence.

Growth rate: The expansion of the number of cells of a specified cell line through cell division as a function of time. In one example the growth rate is the rate at which a cell line grown in culture doubles.

Preferred mammalian codon(s): The subset of codons from among the set of all possible codons encoding an amino acid that are most frequently used in proteins expressed in mammalian cells. Table 1 summarizes preferred mammalian codons for each amino acid:

TABLE 1

| Amino Acid | Preferred codons |
|---|---|
| Gly | GGC, GGG |
| Glu | GAG |
| Asp | GAC |
| Val | GUG, GUC |
| Ala | GCC, GCU |
| Ser | AGC, UCC |
| Lys | AAG |
| Asn | AAC |
| Met | AUG |
| Ile | AUC |

TABLE 1-continued

| Amino Acid | Preferred codons |
|---|---|
| Thr | ACC |
| Trp | UGG |
| Cys | UGC |
| Tyr | UAU, UAC |
| Leu | CUG |
| Phe | UUC |
| Arg | CGC, AGG, AGA |
| Gln | CAG |
| His | CAC |
| Pro | CCC |

In some embodiments, the nucleotide sequence encoding the amino acid sequence of a fluorescent protein has been codon optimized for expression in a mammalian cell. By codon optimized it is meant that at least some of the codons that encode the fluorescent protein have been exchanged for codons that are preferentially used by mammalian cells, for example the codons listed in Table 1. Typically the exchange of codons does not alter the amino acid sequence of the resulting fluorescent protein relative to the fluorescent protein encoded by the nucleic acid sequence with unexchanged codons.

High throughput technique: Through this process one can rapidly identify active compounds, antibodies or genes which affect a particular biomolecular pathway, for example pathways in angiogenesis. In certain examples, combining modern robotics, data processing and control software, liquid handling devices, and sensitive detectors, high throughput techniques allows the rapid screening of potential pharmaceutical agents in a short period of time.

Histology: The study of the microscopic anatomy and classification of tissue, including the histology of mammalian cells, such as cells and cell lines from mammalian tissues. Histological typing refers to the categorizing of tissue into histological types, for example by microanatomical origin (such as connective tissue, nerves, muscles, and circulatory cells, among others) or cell-types (such as epithelial cells, stromal cells among others). Cells can be classified as being of different histological types by virtue of the staining and/or reaction with antibodies, or by characteristic microanatomical features. Cells of different histological types interact differently with different stains and/or antibodies. Methods for histological typing are well known in the art. Histology can be use to determine if cells are of different types. Thus, in some examples different cell lines are histologically different cell lines.

Immortalized cell or cell line: A cell or cell line that has acquired the ability to proliferate indefinitely either through random mutation or deliberate modification, such as artificial expression of the telomerase gene. There are numerous well established immortalized cell lines representative of particular cell types.

Inhibitor (for example, of angiogenesis): A substance capable of inhibiting to some measurable extent, for example angiogenesis. In disclosed examples inhibition is measured in the assays disclosed herein.

Isolated: An "isolated" biological component (such as a cell (or cell line), nucleic acid, peptide or protein) has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a cell as well as chemically synthesized nucleic acids. The term "isolated" or "purified" does not require absolute purity; rather, it is intended as a relative term. Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation. In addition, the term "isolated" can also be applied to a cell or a cell line, for example an isolated cell or cell line is one that is removed from its original host. Isolated cells or cell lines can be placed back in a host, even the host from which they were originally isolated.

Metastatic potential: The ability of cancer cells to leave the original tumor site and migrate to other parts of the body, for example via the bloodstream or lymphatic system. In particular examples, the metastatic potential of a tumor cell is indicated by movement of a tumor cell along pre-vascular endothelial tubules in vitro (angiotropism).

Migration potential: The ability of cells, such as the cell line disclosed herein, to translocate in response to a chemical stimulus, such as a growth factor. Migration potential can be determined with the assays disclosed herein.

Mimetic: The ability for a composition or an environment to resemble another composition or environment. In particular examples, an in vitro cell culture provides a mimetic to an in vivo context when the cells of the culture behave in a manner that correlates to their in vivo behavior.

Mixed cell population: A population of cells, such as cells in culture, that contains two or more different types of cells, such as histologically different cell lines. Examples of different types of cells include cells of different embryonic origin (such as cells originating from the ectoderm, endoderm, or mesoderm), cells from different cellular locations (such as cells from epithelium, endothelium, or stroma), cells from different tissues or organs (such as cells from pulmonary myocardial, neural, vascular, skin, bone, or skeletal or smooth muscle tissue).

Neoplasm or tumor: Any new and abnormal growth; particularly a new growth of tissue in which the growth is uncontrolled and progressive. A neoplasm, or tumor, serves no useful function and grows at the expense of the healthy organism.

In general, tumors appear to be caused by abnormal regulation of cell growth. Typically, the growth of cells in the body is strictly controlled; new cells are created to replace older ones or to perform new functions. If the balance of cell growth and death is disturbed, a tumor may form. Abnormalities of the immune system, which usually detects and blocks aberrant growth, also can lead to tumors. Other causes include radiation, genetic abnormalities, certain viruses, sunlight, tobacco, benzene, certain poisonous mushrooms, and aflatoxins.

Tumors are classified as either benign (slow-growing and usually harmless depending on the location), malignant (fast-growing and likely to spread and damage other organs or systems) or intermediate (a mixture of benign and malignant cells). Some tumors are more common in men or women, some are more common amongst children or elderly people, and some vary with diet, environment and genetic risk factors.

Symptoms of neoplasms depend on the type and location of the tumor. For example, lung tumors can cause coughing, shortness of breath, or chest pain, while tumors of the colon can cause weight loss, diarrhea, constipation and blood in the stool. Some tumors produce no symptoms, but symptoms that often accompany tumors include fevers, chills, night sweats, weight loss, loss of appetite, fatigue, and malaise.

Blood vessels supply tumors with nutrients and oxygen. Tumor growth is dependent on the generation of new blood vessels that can maintain the needs of the growing tumor, and many tumors secrete substances (angiogenic factors) that are able to induce proliferation of new blood vessels (angiogenesis). Anti-tumor therapies include the use of angiogenesis inhibitors, which reduce the formation of blood vessels in the tumor, effectively starving the tumor and/or cause the tumor to drown in its own waste.

Neovascularization: The growth of new blood vessels. Neovascularization can be the proliferation of blood vessels in tissue not normally containing them, or the proliferation of blood vessels in an ischemic or otherwise damaged tissue. Neovascularization can be pathological when it is unwanted or mediates a pathological process, for example when it occurs in the retina or cornea.

Neutral: A molecule is neutral when its overall charge is neither positive nor negative. One example of a neutral polysaccharide is agarose.

Nucleic acid: A deoxyribonucleotide or ribonucleotide polymer in either single (ss) or double stranded (ds) form, and can include analogues of natural nucleotides that hybridize to nucleic acids in a manner similar to naturally occurring nucleotides. In some examples, a nucleic acid is a nucleotide analog.

Unless otherwise specified, any reference to a nucleic acid molecule includes the reverse complement of nucleic acid. Except where single-strandedness is required by the text herein (for example, a ssRNA molecule), any nucleic acid written to depict only a single strand encompasses both strands of a corresponding double-stranded nucleic acid. For example, depiction of a plus-strand of a dsDNA also encompasses the complementary minus-strand of that dsDNA. Additionally, reference to the nucleic acid molecule that encodes a specific protein, or a fragment thereof, encompasses both the sense strand and its reverse complement.

Operably connected or operably linked: A first nucleic acid sequence is operably connected to a second nucleic acid sequence when the first nucleic acid sequence is placed in a functional relationship with the second nucleic acid sequence. For instance, a promoter is operably connected to a coding sequence, such as the coding sequence of a fluorescent protein, for example GFP, if the promoter affects the transcription or expression of the coding sequence. Generally, operably connected DNA sequences are contiguous.

Passaging cells: Passaging or splitting cells involves transferring a small number of cells into a new vessel. Cells can be cultured for a longer time if they are split regularly, as it avoids the senescence associated with prolonged high cell density. Suspension cultures are easily passaged with a small amount of culture containing a few cells diluted in a larger volume of fresh media. For adherent cultures, cells first need to be detached; which is typically done with a mixture of trypsin-EDTA. A small number of detached cells can then be used to seed a new culture.

Pharmaceutical agent or drug: A chemical compound or composition capable of inducing a desired therapeutic or prophylactic effect when properly administered to a subject (such as the inhibition of angiogenesis), alone or in combination with another therapeutic agent(s) or pharmaceutically acceptable carriers. Pharmaceutical agents include, but are not limited to, angiogenic factors, for example bFGF, and VEGF, and anti-angiogenic factors, such as inhibitors of bFGF, or VEGF. For example, suitable anti-angiogenic factors include, but are not limited to, SU5416, which is a specific VEGF-R antagonist, SU6668 which blocks the receptors for VEGF, bFGF, and PDGF and Avastin®. See, for example, Liu et al., *Seminars in Oncology* 29 (Suppl 11): 96-103, 2002; Shepherd et al., *Lung Cancer* 34:S81-S89, 2001.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Primary cells: Cells that are cultured directly from a subject. With the exception of some derived from tumors, most primary cell cultures have limited lifespan. After a certain number of population doublings cells undergo the process of senescence and stop dividing, while generally retaining viability.

Protein coding sequence or a sequence that encodes a peptide: A nucleic acid sequence that is transcribed (in the case of DNA) and is translated (in the case of mRNA) into a peptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence is usually located 3' to the coding sequence.

Signal: A detectable change or impulse in a physical property that provides information. In the context of the disclosed methods, examples include electromagnetic signals, such as light, for example light of a particular quantity or wavelength, for example a wavelength of light emitted from a fluorescent protein.

Recombinant: A recombinant nucleic acid or protein is one that has a sequence that is not naturally occurring (for example a vector, such as a vector encoding a fluorescent protein, such as GFP and the like) or has a sequence that is made by an artificial combination of two otherwise separated segments of sequence. This artificial combination can be accomplished, for example, by chemical synthesis or by the artificial manipulation of isolated segments of nucleic acids or proteins, for example, by genetic engineering techniques.

Test agent: Any agent that that is tested for its effects, for example its effects on a cell. In some embodiments, a test agent is a chemical compound, such as a chemotherapeutic agent or even an agent with unknown biological properties.

Therapeutically effective amount: A dose sufficient to have a therapeutic effect, for example to inhibit to some degree advancement, or to cause regression of the disease, or which is capable of relieving symptoms caused by the disease. For example, a therapeutically effective amount of an angiogenesis inhibitor can vary from about 0.1 nM per kilogram (kg) body weight to about 1 nM per kg body weight, such as about 1 nM to about 500 nM per kg body weight, or about 5 nM to about 50 nM per kg body weight. The exact dose is readily determined by one of skill in the art based on the potency of the specific compound, the age, weight, sex and physiological condition of the subject.

Treating: Inhibiting the full development of a disease or condition, for example, in a subject who is at risk for a disease such as cancer. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology. A personalized treatment is a treatment that is tailored to a particular subject based on the characteristics of the subject and optionally also the particular disease.

Transduced Transformed, Transfected: A virus or vector "transduces" or "transfects" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Tumor spheroid colony: An in vitro clonal expansion of a single parental tumor cell and which has the three dimensional characteristics of an in vivo tumor. Tumor spheroids include not only morphogenic capacities and histotypic reorganization of an in vivo tumor, but also maintain its functional activities and gene expression patterns (Hauptmann et al., *Int. J. Cancer.* 61:819-825, 1995). Additionally, tumor spheroids provide a simple geometry for modeling the effects of anticancer treatments (Buffa et al., *Int J Radiat Oncol Biol Phys.* 49:1109-1118, 2001).

Tumor biopsy: A section of tumor tissue removed from a whole tumor, for example a tumor from a subject. Tumor biopsies contain a mixed population of cells including tumor and stromal cells. In particular examples, a tumor biopsy is a tumor tissue plug, which is a section of a punch biopsy (periphery, mid-section, and central core) from a tumor, such as a tumor from a subject or a xenograft tumor.

Tubule formation potential: The ability of a cell line to form a tube-like structure in vitro, for example a structure similar to a blood vessel, such as a capillary. Tubule formation potential can be determined by determining the pattern displayed by cells which have been induced to form tubules, for example by determining the pattern of fluorescence from cells expressing fluorescent proteins, such as the cell lines disclosed herein. In particular examples, tubule formation potential is a characteristic of endothelial cells. In other examples it is a characteristic of other cell types including certain tumor cells lines (e.g. MDA-MB-435) and pericytes.

Vector: A nucleic acid molecule that can be introduced into a cell, thereby producing a transformed cell. A vector can include nucleic acid sequences that permit it to replicate in a cell, such as an origin of replication, for example a SV40 origin for replication in mammalian cells and a pUC origin of replication for propagation in E. coli, and can also include one or more selectable marker genes, such as antibiotic resistance genes, such as the kanamycin resistance gene and the neomycin resistance gene. Other genetic elements and protein coding sequences can also be included in the vector, such as sequences encoding a fluorescent protein, for example GFP or the like, promoters for the expression of proteins, such as the SV40 early promoter and the immediate early promoter of cytomegalovirus (PCMV IE), Kozak translation initiation sequences, and polyadenylation signals, such as the SV40 polyadenylation signal.

III. Description of Several Embodiments

Understanding biological processes that underlie cellular organization, such as in organ development and the pathogenesis of diseases such as cancer, would be facilitated by methods for studying these complex interactions in vitro. In vitro assays are needed to investigate the relationship between multiple cellular components involved in the biological processes (such as angiogenesis), investigate new combinatorial approaches to boost the efficiency of existing therapeutics, and to facilitate the discovery of new potential single and/or combination drugs. Disclosed herein is an in vitro assay that meets these needs.

A basic component of this in vitro assay is the immortalized fluorescent cell lines disclosed herein. The disclosed fluorescent cell lines represent an array of different cell types, such as cell types that contribute to biological processes, such as angiogenesis, in vivo. The disclosed fluorescent cell lines are derived from different anatomical origins which are known to be relevant during the angiogenesis process. In particular examples, the cells are mammalian cell lines, such as human cell lines, and may be immortalized cell lines. The disclosed cell lines have been stably transfected with mammalian expression plasmids that constitutively express different fluorescent proteins, for example green fluorescent protein and related florescent proteins, such as yellow fluorescent protein, red fluorescent protein, cyan fluorescent protein and the like.

The fluorescence signals produced by the cell lines expressing green fluorescent protein and related fluorescent proteins can be used for real time direct estimation of cell numbers, because the fluorescent signal from a population of cells stably and constitutively expressing a fluorescent protein is proportional to the number of such cells. In addition, because these fluorescent cell lines emit a detectable signal that can be localized in space, the individual cells can be localized in space, for example to determine a pattern of fluorescence attributable to the cells. These features can be used in a number of different assays including growth assays, migration assays, tubule formation assays, cell viability assays, and the like. The use of fluorescent cells in such assays, for example the assays disclosed herein, not only eliminates the need for expensive commercially available kits (for example kits needed to generate and end point readable signal, for example a chemical agent that renders the cell, or cell morphology detectable) but also simplifies procedures by considerably shortening the protocol time, because no additional agents need to be added to generate a signal. Additionally, because no detection reagents have to be added to the cells in culture the fluorescent cell lines and assays disclosed herein avoided putatively harmful interactions between those chemicals and the cellular components under study.

Deregulation of angiogenesis plays a major role in a number of human diseases. A dramatic increase in the research effort in the field of angiogenesis has resulted in a substantial understanding of the angiogenic process and subsequently the development of new therapeutics to modulate angiogenesis. Although angiogenesis inhibitors are among the most promising drug candidates for cancer, the existing "single drug, non-personalized" approach has proven to be problematic regarding extending patient survival time and the development of drug resistant tumor clones.

Figure 14:
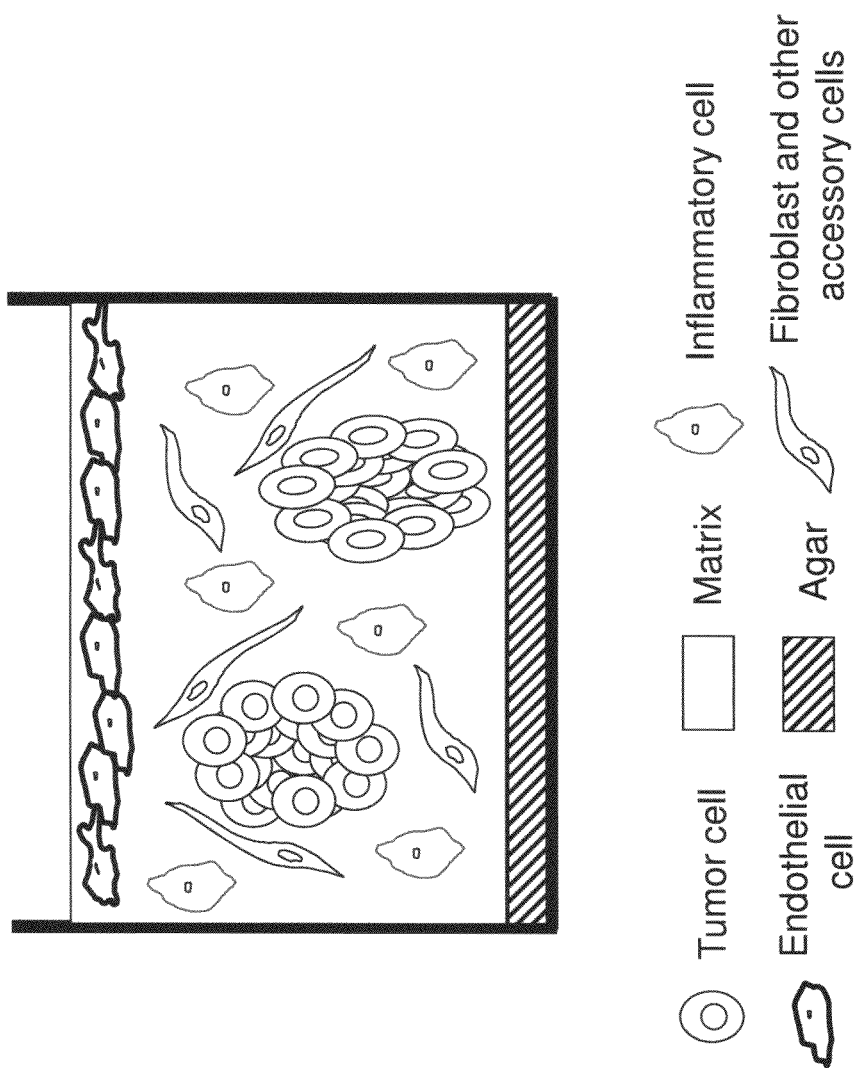
FIG. 14 is a schematic representation of the three-dimensional models for the study of the complex interactions between different cell types in a three-dimensional environment. Because the different cell types used are labeled with different fluorescent proteins it becomes easier to image in real time the evolution of the model. It becomes also possible to sort apart the cells and do gene expression analysis on them. Also, these models allow for screening of drugs (anti-angiogenic, antitumoral, etc) in a more complex in vitro system.

The inability to develop more successful therapies is hampered by insufficient knowledge about the interactions between the multiple cellular components involved in the angiogenesis process and the inability to evaluate angiogenic potential in individual patients. Hence, one of the major problems confronting clinicians today is the ability to assess angiogenic/antiangiogenic therapy effectiveness in a mixed cell environment, such as the mixed cell environment responsible for angiogenesis. The disclosed assays are particularly suited to the investigation of angiogenesis especially in a mixed cell environment, such as a mixed cell environment approximating in vivo conditions (for example a mixed cell population shown in FIG. 14).

The disclosed assays can be used to monitor the effects of a drug, such as an existing angiogenesis inhibitor or other chemotherapeutic agent, on a patient sample, for example, by determining the effect of a patient sample, patient serum, plasma, tumor cells, on the fluorescent cell lines disclosed herein. Using the disclosed assays, a patient sample from a patient with cancer could have elevated level of proangiogenic factors, such as growth factors. Using the disclosed assays, it is possible to monitor the patient, via monitoring a sample obtained from a patient, to determine if a particular treatment is having a desired effect, for example reducing the level of proangiogenic factors present in the sample. Thus, a particular therapy can be developed for an individual patient, for example a personalized combinatorial drug therapy which would be effective for that individual.

Also disclosed herein are methods for monitoring angiogenic or metastatic potential of tumor cells, the methods comprising preparing a three-dimensional co-culture that is comprised of three layers. The first layer comprises a neutral polysaccharide polymer gel in contact with the bottom of the culture dish. The second layer is on top of the first layer and comprises a solidified gel matrix, endothelial cells that are dispersed in the solidified gel matrix; and tumor cells comprising either a tumor spheroid colony or a sample of a tumor biopsy, and which are also suspended in the solidified gel matrix, and a third layer comprising culture medium. Angiogenic or metastatic potential of tumor cells is monitored by incubating the three-dimensional co-culture; and detecting at least one of endothelial cell proliferation, endothelial cell tubule formation or tumor cell angiotropism of the cells in the second layer. In particular examples, the neutral polysaccharide polymer gel comprises agarose. In other examples, the endothelial cells stably and constitutively express a fluorescent protein. In still other examples, the tumor cells stably and constitutively express a fluorescent protein with a different emission spectrum from the fluorescent protein expressed by the endothelial cells. In yet further examples, the second layer further comprises at least one additional mammalian cell type dispersed in the solidified gel matrix, such as a cell type selected from the group consisting of macrophage, mast cell, fibroblast, adipocyte, and pericyte. In still further examples, the additional mammalian cell type stably and constitutively expresses a fluorescent protein with a different emission spectrum from the fluorescent protein expressed by the endothelial cells.

In particular examples of the disclosed methods for monitoring angiogenic or metastatic potential of tumor cells, the first, second, or third layer further comprises at least one test agent, which in some examples is a known or potential inhibitor or promoter of angiogenesis or metastasis.

In other examples of the disclosed methods, the tumor cells are derived from a subject and the first, second, or third layer further comprises at least one test agent that has been administered to the subject as part of a cancer treatment.

Further disclosed herein are methods of testing the efficacy of an anti-angiogenic or anti-metastatic cancer treatment for a subject, comprising monitoring angiogenic or metastatic potential of tumor cells by the above described methods utilizing a three dimensional co-culture, wherein the tumor cells are derived from the subject and the first, second, or third layer comprises at least one test agent that is a candidate anti-cancer treatment.

Additionally disclosed herein are methods of selecting a personalized anti-angiogenic or anti-metastatic treatment for cancer in a subject comprising preparing multiple three-dimensional co-cultures, each co-culture comprising a first layer comprising a neutral polysaccharide polymer gel in contact with the bottom of a culture dish; a second layer on top of the first layer, comprising: a solidified gel matrix; endothelial cells dispersed in the solidified gel matrix; and tumor cells comprising either a tumor spheroid colony or a sample of a tumor biopsy, suspended in the solidified gel matrix; and a third layer on top of the second layer comprising culture medium, wherein all but one of the co-cultures further comprises at least one test agent comprising an anti-angiogenic or anti-metastatic compound in the first, second, or third layers. A personalized anti-angiogenic or anti-metastatic treatment for cancer in a subject is selected by incubating the three-dimensional co-cultures; detecting at least one of endothelial cell proliferation, endothelial cell tubule formation or tumor cell angiotropism of the cells in the second layer; and selecting the at least one test agent having the greatest effect on at least one of endothelial cell proliferation, endothelial cell tubule formation or tumor cell angiotropism in comparison to endothelial cell proliferation, endothelial cell tubule formation or tumor cell angiotropism in the cells of the co-culture without the test agent. In particular examples, the neutral polysaccharide polymer gel comprises agarose. In some examples, the endothelial cells stably and constitutively express a fluorescent protein. In other examples, the tumor cells stably and constitutively express a fluorescent protein with a different emission spectrum from the fluorescent protein expressed by the endothelial cells. In particular examples, the second layer further comprises at least one additional mammalian cell type dispersed in the solidified gel matrix, which in some examples, stably and constitutively expresses a fluorescent protein with a different emission spectrum from the fluorescent protein expressed by the endothelial cell, and in further examples is a cell type selected from the group consisting of macrophage, mast cell, fibroblast, adipocyte, and pericyte.

A. Assays

Aspects of this disclosure relate to an assay method, such as a multiplex assay method, for evaluating cellular activity, for example the cellular activity of the disclosed fluorescent cell lines. The disclosed method involves providing an in vitro culture of one or more cell lines, such as an in vitro mixture of one or more of the fluorescent cell lines disclosed herein, for example cell lines of different histological types, for example different types of mammalian cells, such as mammalian somatic cells. Examples include porcine aortic endothelial cell line PAE, human lymphatic endothelial cell line LEC-1, human microvascular endothelial cell line HMEC-1, or rhesus macaque choroidal endothelial cell line RF/6A (ATTC CRL-1780) (which has marker characteristics of a pericyte line (SMA, TIMP-3, NG2, PDGFR-$\beta$, etc); epithelial cell lines, such as human adenocarcinoma cell line A549; adenocarcinoma cell lines, such as human breast adenocarcinoma cell line MCF7; or mast cell lines, such as human mast cell line HMC-1, among others. These particular cell lines are examples of different cell lines believed to play a role in angiogenesis.

In some embodiments, an in vitro cell line mixture is provided which contains a first isolated mammalian cell line stably and constitutively expressing a first fluorescent protein and one or more additional isolated mammalian cell lines stably and constitutively expressing fluorescent proteins having an emission spectrum different from the emission spectrum of the first fluorescent protein and having different histological types. The in vitro cell line mixture is cultured and the cellular activity of the first isolated mammalian cell line or one or more addition isolated mammalian cell lines present in the culture is assessed by quantifying fluorescence or detecting a pattern of fluorescence from the first fluorescent protein or the fluorescent protein expressed by the one or more additional mammalian cell lines. By providing a mixture of isolated mammalian cell lines of different histological types each expressing a different fluorescent protein with different emission spectra, it is possible to assess the cellular activity of the multiple cell lines present in the mixture, for example simultaneously or serially. Thus, in some embodiments, the cellular activity of the first isolated mammalian cell line present in the mixture is assessed and the cellular activity of the additional isolated mammalian cell lines present in the cell line mixture is assessed by quantifying fluorescence or detecting a pattern of fluorescence from the first fluorescent protein and the fluorescent proteins present in the additional isolated cell lines present in the culture.

In some embodiments, an in vitro cell line mixture is provided which contains a first isolated mammalian cell line stably and constitutively expressing a first fluorescent protein and a second isolated mammalian cell line stably and constitutively expressing a second fluorescent protein, in which the first and second fluorescent proteins have different emission spectra and the first isolated mammalian cell line and the second isolated mammalian cell line are different cell lines, for example cell lines of different histological types. In some embodiments, the cellular activity of the first isolated mammalian cell line present in the mixture is assessed by quantifying fluorescence (for example by quantifying the fluorescence intensity at a particular wavelength, such as the emission maxima) or detecting a pattern of fluorescence from the first fluorescent protein (such as the pattern of fluorescence of the fluorescent proteins present in the fluorescent cell line, for example the location of the fluorescence in two or three dimensional space). In some embodiments, the cellular activity of the first isolated mammalian cell line present in the mixture is assessed and the cellular activity of the second isolated cell line present in the cell line mixture is assessed by quantifying fluorescence or detecting a pattern of fluorescence from the first fluorescent protein and the second fluorescent protein.

In some embodiments, an in vitro cell line mixture is provided which contains at least three, such as three, four, five, six or more, different isolated mammalian cell lines, such as different cell lines each having a different histological type, wherein each isolated mammalian cell line stably and constitutively expresses a different fluorescent protein having an emission spectrum distinguishable from the other fluorescent proteins. In such a mixture each cell line is uniquely associated with a particular fluorescent protein having a different emission spectrum from the other fluorescent proteins so that the individual cell lines present in the mixture can be distinguished, such that the fluorescence from the individual cell line can be quantified and/or the pattern of fluorescence detected. Thus, the quantified fluorescence or pattern of fluorescence attributable to a specific fluorescent cell line can be determined.

In some embodiments, assessing cellular activity includes determining the growth rate, migration potential, and/or tubule formation potential of the first isolated mammalian cell line and/or additional isolated cell lines present in the in vitro mixture using the quantified fluorescence or the pattern of fluorescence from the fluorescent proteins in the mixture, such as first fluorescent protein and/or the additional fluorescent proteins, such as a second, third forth, fifth, six, etc. fluorescent proteins present in the in vitro mixture. In some examples, the number of dead cells present in the mixture is determined by determining the quantified fluorescence present in the media of the cell-mixture. Exemplary methods for determining the growth rate, cell death, migration potential, or tubule formation potential of the isolated cell lines disclosed herein are given below.

i. Growth Assay

Using the disclosed fluorescent cell lines, a real time growth assay has been developed and applied to mono- or multiple-cell cultures (co-culture). As disclosed herein the fluorescence signal emitted by a culture of the disclosed fluorescent cell lines is proportional to the number of fluorescent cells present in the culture (see for example FIG. 2). In other words, the fluorescence signal, for example measured as the intensity of the emission maxima, from a population of fluorescent cells of one type in a culture will double as the number of fluorescent cells of that type in the culture doubles. Conversely, the fluorescence signal, for example measured as the intensity of the emission maxima, from a population of cells of one type in a culture will be reduced to half if the number of cells of that type in the culture is divided in half. These properties can be used to measure the effect of an exogenous agent, such as one or more additional cell lines, or a test agent, on the fluorescent cells in culture. It should be noted that at some point the total fluorescence of a culture may reach signal saturation, such that the signal reaches a plateau as a function of cell number.

Figure 4B:
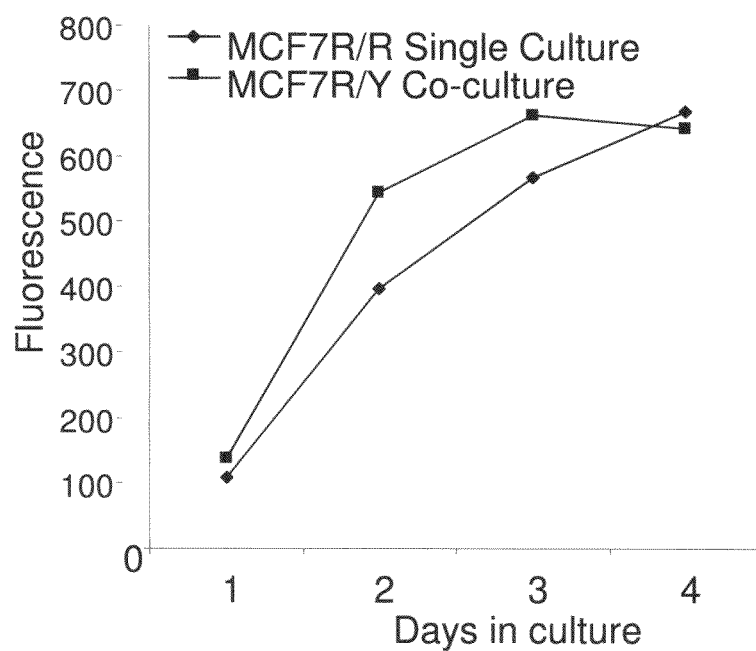
FIG. 4B is a graph of growth curves for MCF7 breast cancer cells expressing RFP in mono-culture or in co-culture with PAE endothelial cells.

In some embodiments, the effect of an additional cell line (for example a different cell line) on a first fluorescent cell line is determined (this can be extended to multiple cell lines and even one or more fluorescent cell lines, or combinations thereof, for example in a multiplex assay). For example, as shown in FIG. 4, the effect of the yellow fluorescent PAE cell line on the red fluorescent MCF7 cell line has been measured.

In some embodiments, the disclosed growth assay is used to assess if the presence of one or more additional cell lines, such as one or more of the fluorescent cell lines disclosed herein, affects the growth rate of a fluorescent cell line of interest. A fluorescent cell line of interest can be grown in co-culture with one or more additional cell lines and the growth of the fluorescent cell line of interest can be determined. For example, using the difference between the fluorescence signal of the fluorescent cell line of interest and a control indicates that the one or more additional cell lines can be used to determine if the one or more additional cell lines affects the growth rate of the fluorescent cell line of interest.

In some embodiments, the difference between the fluorescence signal (such as the intensity of the fluorescence signal at a particular wavelength, for example the emission maxima of the fluorescence signal) attributable to the fluorescent cell line of interest grown in co-culture with one or more additional cell lines relative to a control is at least about 10%, meaning that the growth rate of the cell line of interest is either reduced or increased by at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater then 500%. In some embodiments, the difference is a statistically significant difference. Thus, the presence of one or more additional cell lines can induce a statistically significant difference in the growth rate of a fluorescent cell line of interest, as compared to the control, such as value indicative of the basal rate of growth of the fluorescent cell line, or the fluorescent cell line of interest grown in the absence of the other cells or cell lines, for example grown in mono-culture. In some examples, the additional cell line (or additional cell lines) will have a negative impact on the first fluorescent cell line, such that the number of cells of the first fluorescent cell line is reduced as a function of time relative to a control. In some examples, the additional cell line (or additional cell lines) will have a positive impact on the first fluorescent cell line, such that the number of cells of the first fluorescent cell line present in a cell culture increases as a function of time relative to a control. It is also contemplated that the fluorescent cell line of interest can be co-cultured with primary cells, such as primary cells obtained from a subject, for example tumor cells, and the effect of the primary cells on the growth rate of the fluorescent cell line of interest determined.

In some embodiments, multiple fluorescent cell lines are grown in co-culture. Thus, the effect of each fluorescent cell line on the other fluorescent cell line(s) present can be determined, for example in a multiplex assay. For example, using appropriate filters or FACS analysis among other techniques, fluorescent cell lines expressing different fluorescent proteins, such as red, green, yellow, cyan and the like fluorescent proteins can be discriminated and the fluorescent signal attributable to the different cell lines determined. Thus, the growth rates of individual fluorescent cell lines can be determined from a mono-culture and/or a co-culture of two or more fluorescent cell lines. Such analysis greatly enhances the information that can be obtained about the individual fluorescent cell lines.

In addition to determining the effect of cell lines on a fluorescent cell line of interest, the growth assays can be used to determine if an exogenous agent, such as a test agent, for example a chemical agent, affects the growth of a fluorescent cell line of interest. This can also be extended to multiple cell lines (either fluorescent or not grown in co-culture, for example in a multiplex assay). In some embodiments, the disclosed growth assay is used to determine if an exogenous agent, such as a test agent (for example a potential modulator of angiogenesis, such as a potential inhibitor of angiogenesis or a potential stimulator of angiogenesis), growth factor, patient sample, etc. affects the growth rate of a fluorescent cell line of interest, such as one or more of the fluorescent cell lines disclosed herein. In addition, the differential effect of the exogenous agent on the different cell lines can be determined, as can the combinatorial effect of the exogenous agent and the cells on a cell line of interest.

A fluorescent cell line of interest can be contacted with an exogenous agent and the impact of the exogenous agent on the growth of the fluorescent cell line of interest can be determined. For example, a difference between the fluorescence signal of the fluorescent cell line of interest and a control indicates that the exogenous agent, such as a test agent (for example a potential modulator of angiogenesis, such as a potential inhibitor of angiogenesis or a potential stimulator of angiogenesis), growth factor, patient sample, different cell line, etc. is a modulator (such as an inducer or inhibitor) of angiogenesis. Thus, in several embodiments, one or more of the disclosed fluorescent cell lines growing in culture are contacted with a test agent (or test agents) to determine if the test agent is a modulator of angiogenesis. Exemplary test agents are given below. Following contact with the exogenous agent, the fluorescence of the culture can be measured versus time and/or concentration to determine the impact of the exogenous agent on the one or more fluorescent cell lines present in the culture. For example, the fluorescence signal generated by a fluorescent cell line of interest (such as the intensity of the fluorescence signal at a particular wavelength, for example the emission maxima of the fluorescence signal) can be measured to determine if the fluorescence signal attributable to the fluorescent cell line of interest (such as the intensity of the fluorescence signal at a particular wavelength, for example the emission maxima of the fluorescence signal) is increasing as a function of concentration of the exogenous agent, time, or both, for example by comparison with a control, such as a value indicative of the basal rate of growth of the fluorescent cell line of interest or the fluorescent cell line of interest not contacted with the exogenous agent. In several embodiments, the control is a known value indicative of normal growth of the fluorescent cell line of interest, for example the doubling time of cellular number. In some embodiments, the control is the fluorescence signal of a culture of cells (typically, but not necessarily, a culture of the fluorescent cell line of interest) not contacted with the exogenous agent.

In some embodiments, an exogenous agent, such as a test agent, decreases the growth rate of the fluorescent cell line of interest. A test agent exhibiting such an activity is identified as an inhibitor of angiogenesis and would be of use in treating a disease or condition in which normal angiogenesis is increased, for example cancer. In some embodiments, a decrease in the growth rate of the fluorescent cell line of interest relative to a control is at least about a 30%, at least about a 40%, at least about a 50%, at least about a 60%, at least about a 70%, at least about a 80%, at least about a 90%, at least about a 100%, at least about a 150%, at least about a 200%, at least about a 250%, at least about a 300%, at least about a 350%, at least about a 400%, at least about a 500% decrease. Because the fluorescence signal attributable to a fluorescent cell line of interest is proportional to the number of cells of the cell line of interest present, the percentage decrease can be measured as a percentage decrease in the fluorescent signal, for example the fluorescence intensity at a particular wavelength, such as the emission maxima, attributable to the cell line of interest. In additional embodiments, the decrease is a statistically significant decrease as compared to a control.

In other embodiments, the exogenous agent, such as a test agent, increases the growth of the fluorescent cell line as compared to a control. A test agent exhibiting such an activity is identified as a stimulator of angiogenesis and would be of use in treating a disease or condition in which normal angiogenesis is inhibited. In some embodiments, an increase in the growth of the fluorescent cell line is at least about a 30%, at least about a 40%, at least about a 50%, at least about a 60%, at least about a 70%, at least about a 80%, at least about a 90%, at least about a 100%, at least about a 150%, at least about a 200%, at least about a 250%, at least about a 300%, at least about a 350%, at least about a 400%, at least about a 500% increase as compared to control. Because the fluorescence signal attributable to a fluorescent cell line of interest is proportional to the number of cells of the cell line of interest present, the percentage increase can be measured as a percentage increase in the fluorescent signal, for example the fluorescence intensity at a particular wavelength, such as the emission maxima, attributable to the cell line of interest. In additional embodiments, the increase is a statistically significant increase as compared to a control.

ii. Tubule Formation Assay

Similarly to the growth assay, cultures of fluorescent cell lines expressing different fluorescent proteins, such as the fluorescent cell lines disclosed herein can be applied to tubule formation assays. Formation of new blood vessels is fundamental to angiogenesis and is the focus of many drug screening and cell signaling studies. Blood vessel development is a significant event in the development and growth of solid tumors, and is involved in wound healing, retinopathy and macular degeneration. The disclosed fluorescent cell lines, and in particular the disclosed endothelial fluorescent cell lines are ideal for use in assays for assessing the degree of blood vessel formation using in vitro cell culture assays (see for example Auerbach et al. 2003. *Clinical Chemistry* 49:1, 32-40. 2. Taraboletti and Giavazzi, 2004 *EJC.* 40, 881-889). Because no fluorescent/colorimetric staining is needed, the tubule formation assay can be followed over time and can be directly visualized used in existing instrumentation, such as the BD Pathway™ Bioimager (BD Bioscience, San Jose, Calif.). This allows for the study of the interaction between different cells types in this angiogenesis in vitro assay. In addition, the tubule formation potential can also be determined for a co-culture of a fluorescent cell line of interest with primary cells, such as primary cells obtained from a subject, for example tumor cells.

Tubule Formation assays are typically based on the ability of endothelial cells, such as the fluorescent endothelial cells disclosed herein, to form distinct blood-vessel-like tubules in an extracellular matrix (such as BD Matrigel™ Matrix available from BD Bioscience, BME available from Trevigen, or Geltrex™ available from Invitrogen®, and the like). In other examples, tubule formation assays involve observation of the tubule forming potential of certain tumor cell lines (e.g. MDA-MB-435) and pericytes. The cells are visualized under microscopy, such as fluorescence microscopy in the case of the fluorescent cell disclosed herein, and the ability of a fluorescent cell line of interest to form tubules (also called the tubule formation potential) is determined. The determination of tubule formation can be performed by manual tracing or by automated confocal imaging system, for example using a BD Pathway™ Bioimager in conjunction with AngioApplication™. Using the disclosed fluorescent cell lines, tubule formation assays can be performed on live cells, for example to avoid artifact that may arise from fixation artifacts, such as the disruption of tubules. Several parameters can be measured in tubule formation assays, such as the total area of the tubules, the total number of tubules, number of nodes, number of branch points, the number of tubes per node, and/or node area. In some embodiments, the tubule formation potential is determined by a computer implemented method, for example using the program AngioApplication™.

The fluorescent cell lines disclosed herein can be used to determine the effects of an exogenous agent, such as cell lines and test agents, on tubule formation. In some embodiments, multiple fluorescent cell lines are grown in co-culture. Thus, the effect of each fluorescent cell line on the other fluorescent cell line(s) present can be determined, or the differential effect of an exogenous agent, such as a test agent, or patient sample, on the different cell lines can be assessed in a multiplex assay. For example using appropriate filters, the fluorescent signal from fluorescent cell lines expressing different fluorescent proteins, such as red, green, yellow, cyan fluorescent proteins can be discriminated and the fluorescent signal attributable from the different fluorescent cell lines determined. Thus, the tubule formation potential of individual cell lines can be determined from a mono-culture or even a co-culture, for example a co-culture of more than one fluorescent cell line.

When grown in co-culture, a difference between the tubule formation potential of the fluorescent cell line of interest from a control, such a mono-culture of the fluorescent cell line of interest indicates that the other cell line(s) is a modulator of angiogenesis, as evidenced by the difference in tubule formation potential. In some embodiments, the difference between the tubule formation potential, for example as measured by the number of least one of the total area of the tubules, the total number of tubules, number of nodes, number of branch points, the number of tubes per node, or node area formed in the co-culture of the fluorescent cell line of interest relative to a control is at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater then 500%. In some embodiments, the difference is a statistically significant difference. Thus, a cell line can induce a statistically significant difference in the tubule formation potential of a fluorescent cell line of interest, such as one of the disclosed fluorescent cell lines. Taking a combinatorial approach the impact of multiple different cell lines either alone or in combination on the tubule formation potential of the fluorescent cell line of interest can be determined. In some examples, the presence of one or more additional cell lines increases the tubule formation potential of the fluorescent cell line of interest, for example as measured by the total area of the tubules, the total number of tubules, number of nodes, number of branch points, the number of tubes per node, or node area formed by the fluorescent cell line of interest. These cell lines would be identified as positive regulators of angiogenesis. In some examples, the presence of one or more additional cell lines decreases the tubule formation potential of the fluorescent cell line of interest, for example as measured by the total area of the tubules, the total number of tubules, number of nodes, number of branch points, the number of tubes per node, or node area formed by the fluorescent cell line of interest. These cell lines would be identified as negative regulators of angiogenesis.

Utilizing the disclosed fluorescent cell lines, tubule formation assays can also be used to screen for a biological effect of a test agent, such as the effect of potential modulators of angiogenesis. In some embodiments, a fluorescent cell line of interest (or multiple cell lines of interest in a multiplex assay) can be contacted with an exogenous agent, such as a cell line or test agent, and the impact of the exogenous agent on tubule formation potential can be determined. Exemplary test agents are given below. For example using the difference between the total area of the tubules, the total number of tubules, number of nodes, number of branch points, the number of tubes per node, and/or node area between a fluorescent cell line of interest and a control are used to determine if an exogenous agent, such as a test agent, impacts the ability of a fluorescent cell line of interest to form tubules. A difference between the tubule formation potential of a fluorescent cell line of interest contacted with an exogenous agent and a control (such as a control culture exposed to the exogenous agent) indicates that the exogenous agent is a modulator of angiogenesis. In some embodiments, the difference between the tubule formation potential of the fluorescent cell line contacted with an exogenous agent relative to a control is at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater then 500%. In some embodiments, the difference is a statistically significant difference. Thus, an exogenous agent can induce a statistically significant difference in the tubule formation potential of the fluorescent cell line of interest contacted with the test agent, as compared to the control, such as the fluorescent cell line of interest not contacted with the exogenous agent.

In one embodiment, the exogenous agent decreases ability of a fluorescent cell line of interest to form tubules. A test agent exhibiting such an activity is identified as an inhibitor of angiogenesis and would be of use in treating a disease or condition in which normal angiogenesis is increased, for example cancer. In some embodiments, a decrease in the tubule formation potential of the fluorescent cell line of interest is at least about a 30%, at least about a 40%, at least about a 50%, at least about a 60%, at least about a 70%, at least about a 80%, at least about a 90%, at least about a 100%, at least about a 150%, at least about a 200%, at least about a 250%, at least about a 300%, at least about a 350%, at least about a 400%, at least about a 500% decrease as compared to control. In additional embodiments, the decrease is a statistically significant decrease as compared to a control.

In another embodiment, the exogenous agent increases the potential of a fluorescent cell line of interest to form tubules as compared to a control, such as the fluorescent cell line of interest that has not been contacted with the exogenous agent. A test agent exhibiting such an activity is identified as a stimulator of angiogenesis and would be of use in treating a disease or condition in which normal angiogenesis is inhibited. In some embodiments, an increase in the growth of the fluorescent cell line is at least about a 30%, at least about a 40%, at least about a 50%, at least about a 60%, at least about a 70%, at least about a 80%, at least about a 90%, at least about a 100%, at least about a 150%, at least about a 200%, at least about a 250%, at least about a 300%, at least about a 350%, at least about a 400%, at least about a 500% increase as compared to control. In additional embodiments, the increase is a statistically significant increase as compared to a control.

iii. Migration Assay

Another assay that can be used with the disclosed fluorescent cell lines is a cellular migration assay. These assays assess cellular migration in a controlled environment, such as a differential migration of the cell line, (or multiple cell lines in a multiplex assay) as determined by fluorescent signals (such as the intensity of a fluorescent signal of a particular color, or at a particular wavelength, such as the emission maxima of a particular fluorescent protein) in a location that is associated with migration to a particular location.

In one example, a cellular migration assay determines the ability of cells to migrate up or down a chemical gradient. Migration "up" a chemical gradient refers to migration from a region of lower chemical concentration of a chemical to a region of higher chemical concentration (for example migration toward a higher concentration of a chemical attractant or away from a lower concentration of the chemical attractant), while migration "down" a chemical gradient refers to migration from a region of higher chemical concentration to a region of lower chemical concentration (for example migration away from a higher concentration of a chemical repellent toward a lower concentration of the chemical repellent). Such migration is typically referred to as chemotaxis. Cells, such as the fluorescent cell lines disclosed herein, respond to chemical signals in their environment by the stimulation of concerted movement either toward a chemical attractant or away from a chemical repellent. In mammalian cells, such as the fluorescent cell lines disclosed herein, typical chemo-attractants include factors excreted by cells, for example factors found in serum, such as growth factors and the like.

The disclosed fluorescent cells can be used in any cell migration assay format, such as the ChemoTx™ system (NeuroProbe, Rockville, Md.) transwell system or any other suitable device or system. In some examples, a cell migration assay is carried out as follows. A culture of a fluorescent cell line of interest (such as any of the disclosed fluorescent cell lines or a mixture of such as fluorescent cell lines) is placed into a first chamber of a cell migration apparatus, and an exogenous agent (such as a chemoattractant) is placed in a second chamber that is adjacent to and in communication with the first chamber of the cell migration apparatus, so that cellular migration from the first chamber to the second chamber can be detected. The chambers may be separated by a membrane or filter that permits passage of cells from one chamber to the other chamber. The membrane or filter is configured such that the passive diffusion of the cells across the membrane or filter is minimized. In one example, the first chamber is the upper chamber of the apparatus and the second chamber is the lower chamber of the apparatus. In some examples the upper chamber is omitted and the cells are placed directly on a membrane or filter in communication with the lower chamber. The ability of a fluorescent cell line such as the fluorescent cell lines disclosed herein to be stimulated to migrate can be determined. Typical migration assays have "unknown" sites (with cell suspension above the filter and a solution containing the chemotactic factor below it) and "negative control" sites (with cell suspension above the filter and suspension media, but no chemotactic factor, below). Random migration of unstimulated cells will account for some of the cells that pass through the filter. Migrated cells at the negative control sites show the extent of unstimulated random migration, which can then be differentiated from chemotactic migration, or chemotaxis. Cells that stably express a fluorescent protein, such as the disclosed fluorescent cells can be read in a microplate with a fluorescence microplate reader. Thus, the number of fluorescent cells present in either the upper chamber, lower chamber, or both chambers can be determined, for example as a function of time.

In some embodiments, the disclosed migration assay is used to determine if an exogenous agent affects or differentially affects the migration of one or more of the fluorescent cell line of interest, such as one or more of the fluorescent cell lines disclosed herein. A fluorescent cell line of interest can be contacted with exogenous agent and the impact of the exogenous agent on the migration of the fluorescent cell line of interest can be determined. For example, a difference between the number of cells that migrate between a fluorescent cell line of interest contacted with an exogenous agent and a control indicates that the exogenous agent, such as a test agent, cell line, growth factor, etc., is a modulator of cellular migration. In other embodiments, differences in migration among different cell lines in the migration assay provide an indication of differential migration of the different cell lines in response to the exogenous agent. In some embodiments, the difference between the number of cells that migrate of the fluorescent cell line contacted with an exogenous agent relative to a control, (for example as measured by the fluorescence intensity of a fluorescent protein stably and constitutively expressed by the cells) is at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater then 500%. In some embodiments, the difference is a statistically significant difference. Thus, an exogenous agent can induce a statistically significant difference in the migration of a fluorescent cell line of interest contacted with the exogenous agent, as compared to the control, such as the fluorescent cell line of interest not contacted with the exogenous agent or a different cell line that has been mixed with the cell line of interest.

In one embodiment, the exogenous agent decreases the ability of a fluorescent cell line of interest to migrate. A test agent with such an activity is identified as an inhibitor of angiogenesis and would be of use in treating a disease or condition in which normal angiogenesis is increased, for example cancer. In some embodiments, a decrease in migration of the fluorescent cell line of interest is at least about a 30%, at least about a 40%, at least about a 50%, at least about a 60%, at least about a 70%, at least about a 80%, at least about a 90%, at least about a 100%, at least about a 150%, at least about a 200%, at least about a 250%, at least about a 300%, at least about a 350%, at least about a 400%, at least about a 500% decrease as compared to control. In additional embodiments, the decrease is a statistically significant decrease as compared to a control.

In another embodiment, the exogenous agent increases the migration of the fluorescent cell line of interest as compared to a control. A test agent with such as activity is identified as a stimulator of angiogenesis and would be of use in treating a disease or condition in which normal angiogenesis is inhibited. In some embodiments, an increase in migration of the fluorescent cell line is at least about a 30%, at least about a 40%, at least about a 50%, at least about a 60%, at least about a 70%, at least about a 80%, at least about a 90%, at least about a 100%, at least about a 150%, at least about a 200%, at least about a 250%, at least about a 300%, at least about a 350%, at least about a 400%, at least about a 500% increase as compared to control. In additional embodiments, the increase is a statistically significant increase as compared to a control.

iv. Cell Viability Assay

Another example of an assay that can be used with the disclosed fluorescent cell lines is a cell viability assay. These assays are based on the release of fluorescent protein from the cytoplasm of fluorescent cell lines that constitutively express fluorescent protein that occurs when the integrity of the cell membrane of the cells is compromised, for example when the cell dies, such as when the cell is exposed to a cytotoxic agent, such as a test agent that is cytotoxic to the cell. Upon exposure to a cytotoxic agent the fluorescent protein is liberated to the culture media and it can be measured, for example using a fluorimeter. The greater the amount of fluorescent protein liberated from the cells present in the culture, the greater the intensity of the fluorescence present in the media. The measured fluorescence in the media corresponds to number of dead cells.

In some embodiments, the cell viability assay is used to determine if an exogenous agent is cytotoxic to one or more of the fluorescent cell lines of interest, such as one or more of the fluorescent cell lines disclosed herein. A fluorescent cell line of interest can be contacted with exogenous agent and the impact of the exogenous agent on the death of the fluorescent cell line of interest can be determined. For example, an increase in the relative florescence present in the media of between a fluorescent cell line of interest contacted with an exogenous agent and a control indicates that the exogenous agent, such as a test agent, cell line, growth factor, etc., is cytotoxic to the cell line of interest. In other embodiments, differential cytotoxicity of an exogenous agent to different cell lines in the cell viability assay provides an indication that a specific exogenous agent is preferentially cytotoxic to one cell line but not other cell lines present in the culture. Such information is useful for screening agents that are preferentially or differentially cytotoxic to a specific cell-type, for example to the exclusion of other cell types. For example, in a mixed cell population a test agent could be screened to determine if it was cytotoxic (for example differentially cytotoxic) to diseased cells (such as tumor cells) present in the mixed cell population, but not normal cells present in the mixed cell population.

In some embodiments, the difference between the fluorescence of the media of a fluorescent cell line contacted with an exogenous agent relative to a control, (for example as measured by the fluorescence intensity of a fluorescent protein liberated from the cell line into the media) is at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater then 500%. In some embodiments, the difference is a statistically significant difference. Thus, an exogenous agent can induce a statistically significant difference in the number of cells that die as a the migration of a fluorescent cell line of interest contacted with the exogenous agent, as compared to the control, such as the fluorescent cell line of interest not contacted with the exogenous agent or a different cell line that has been mixed with the cell line of interest.

The fluorescent cell lines of the present invention can be used in the above-discussed assays to monitor endothelial cell responses to various exogenous agents, including test agents. However, as described herein, endothelial cell responses to tumor cells in two-dimensional culture assays are not correlative with observations of tumor-stimulated angiogenesis in the in vivo whole animal context. In order to recreate the in vivo tumor microenvironment in an in vivo context, a three-dimensional co-culture assay was developed, as discussed in detail below.

B. Immortalized Fluorescent Cell Lines

Disclosed herein are immortalized mammalian cell lines that stably express a fluorescent protein. The disclosed fluorescent cell lines are produced in disclosed examples by transfecting mammalian expression vectors for fluorescent proteins, such as green, yellow, red and blue fluorescent proteins and the like into a variety of cell lines such as cell lines derived from both vascular and lymphatic endothelial cells as well as inflammatory cells (such as monocytes and mast cells) and tumor cells (such as tumor cells from lung, breast, and the like). The transfected cells are selected for stable (through antibiotic resistance) and high-homogeneous expression (through flow cytometry cell sorting) of the fluorescent proteins.

In some embodiments, the disclosed mammalian cell line is stably transfected with a mammalian expression vector that includes a nucleotide sequence encoding the amino acid sequence of a fluorescent protein, operably connected to a constitutively active promoter that drives the expression of the fluorescent protein and a nucleotide sequence encoding a selection marker. The disclosed fluorescent cell lines stably effect high level expression of the fluorescent protein in the absence of a selection agent and maintain high level expression of the fluorescent protein when the fluorescent cell lines proliferate through multiple passages, for example 10 passages, 20 passages, 30 passages, 40 passages, 50 passages, 100 passages, 150 passages, 200 passages, 250 passages, 300 passages, 400, or even greater than 500 passages of the cell line.

The disclosed cell lines can be derived from any mammalian species, for example humans, apes, monkeys, swine, bovine, and the like. In some embodiments, the fluorescent cell line is an endothelial cell line, for example the porcine aortic endothelial cell line PAE (see for example FIG. 1A-1D), the human lymphatic endothelial cell line HMEC-1, or the rhesus macaque choroidal endothelial cell line RF/6A (ATCC CRL-1780). In some embodiments, the fluorescent cell line is an epithelial cell line, for example the human adenocarcinoma cell line A549. In some embodiments, the fluorescent cell line is an adenocarcinoma cell line, for example the human breast adenocarcinoma cell line MCF7. In some embodiments, the fluorescent cell line is a mast cell line, such as the human mast cell line HMC-1.

The fluorescent cell lines can be transfected with vectors expressing different fluorescent proteins, such as green, yellow, red and cyan among others, such that a cell line can be constructed that stably and constitutively expresses each of the fluorescent proteins. In other words, a particular parental cell line can be divided into sub cell lines, in which each of the sub cell lines expresses a different fluorescent protein. The nucleic acids encoding fluorescent proteins can be expressed in mammalian cell lines. Transfection of mammalian cell lines with recombinant DNA may be carried out by conventional techniques as are well known to those skilled in the art, for example as calcium phosphate coprecipitates, the use of conventional mechanical procedures such as microinjection, electroporation (for example using a NUCLEOFECTOR™ II available from AMAXA®) and insertion of a plasmid encased in liposomes.

Polynucleotide sequences encoding the fluorescent proteins can be operatively connected to expression control sequences. An expression control sequence operatively connected to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the fluorescent proteins can be inserted into an expression vector including, but not limited to a plasmid, to allow insertion or incorporation of sequences into mammalian cell lines. Biologically functional plasmid DNA vectors capable of expression and replication in a mammalian cell line are known in the art.

Examples of vectors that can be used in constructing the disclosed fluorescent cell lines include those vectors available from AMAXA®, such as pmaxFP-Green-C, pmaxFP-Green-N, pmaxFP-Yellow-C, pmaxFP-Yellow-N, pmaxFP-Yellow-PRL, pmaxFP-Red-C, and pmaxFP-Red-N, and vectors available from Clontech, such as pAcGFP1-Hyg-N1, pAcGFP1-N1, pAcGFP1-N2, pAcGFP1-N3, pAmCyan1-N1, pAsRed2-N1, pDsRed2-N1, pDsRed-Express-N1, pDsRed-Monomer-Hyg-N1, pDsRed-Monomer-N1, pHcRed1-N1/1, pZsGreen1-N1, pZsYellow1-N1 and the like.

Those of skill in the art will also recognize that the selection marker component of the vector need not be restricted to an antibiotic resistance gene. By "selection marker" it is meant a gene encoding a protein wherein an activity of the expressed protein is suitable for exerting selection pressure on the cell in which it is expressed. Many selection markers are known to those of skill in the art, including but not limited to resistance markers for antibiotics such as ampicillin, streptomycin, kanamycin, neomycin and the like. Any suitable selection marker may be utilized to construct the vectors of the present disclosure for transfection of the mammalian cell lines, so long as the selection marker provides appropriate selection pressure on the cells within which it is contained.

The disclosed cell lines can be further sorted by fluoresce activated cell sorting (FACS) to select for cells from a particular cell line that have the greatest fluorescence intensity for a particular fluorescent protein, for example, by gating on the brightest population of cells and sorting these cells for further propagation. In certain embodiments, the disclosed fluorescent cell lines have been sorted by FACS to select for cells that stably and constitutively express fluorescent proteins. In some situations it is advantageous to FACS sort a florescent cell line multiple times, such as 2, 3, 4, 5, 6, 7, 8, 9, or even greater than 9 times to enrich for a population of cells that stably and constitutively expresses a fluorescent protein.

The ability to create multiple different cell lines expressing different fluorescent proteins enhances the ability to study cells in co-cultures where different cell lines are included in the same assay. Different combinations of fluorescent cells enable the study of the interaction between different cell types at the qualitative (morphological) and quantitative level. The use of these cells will also ease the development of new in vitro multicellular angiogenesis models, such as those disclosed herein.

In particular, the disclosed cell lines are useful in the estimation of the angiogenic potential of patient serum samples and assessment of physiologically active angiogenic/antiangiogenic drug levels in patient samples. The disclosed cell lines also are well suited for integration into existing angiogenesis assays, such as growth assays, migration/invasion assays, tubule formation assays, cell viability assay, cell to cell interaction assays, cell to matrix interaction assays, apoptosis assays, and are particularly amenable to study by fluorescent/confocal microscopy, for example to determine on a cell by cell basis the effects co-culture has on different cell lines, such as cell lines from different anatomical origins.

The disclosed cell lines can be integrated into existing kits to replace standard reagents. Tubule formation assays are an example of an assay that would substantially benefit from inclusion of one or more of the disclosed cell lines. Typical tubule formation assays require the staining of the cells with calcein AM prior to the assay. Multiple problems are associated with this approach, including interaction of the staining chemical with the cellular objects of study (calcein AM is a known inhibitor of certain cell types), interexperimental variability of the staining protocol, and the inability to use different cell types on the same assay. The use of the disclosed stably transfected fluorescent cell lines in tubule formation assays would eliminate the staining of cells with calcein, eliminate the variability in emitted fluorescence and greatly expand the capabilities of the assay introducing the possibility of the use of multiple cell types in the same assay.

Another advantage of the use of stable fluorescent cellular in vitro assays is that at any time during the assay the cells can be observed under a fluorescent microscope, which allows for morphological analysis and comparison of mono-cultures versus co-cultures. For example, tubule formation and morphological analysis is assessed as a function of time.

C. AngioApplicaton™

Angiogenesis in vitro assays (such as the tubule formation assay disclosed herein) and ex vivo assays (such as chicken chorioallantoic assay) are fundamental tools to the angiogenesis field. One of the hurdles in determining the effects of exogenous agents in such assays, for example, the tubule formation assays disclosed herein, is determining and quantifying the effects of such exogenous agents on the tubule formation potential of the cell line or cell lines under study, for example the fluorescent cell lines disclosed herein. Automated technologies assist with the precise morphological quantification of a vasculature formation assay, such as the tubule formation assay disclosed herein, for example to determine the total area of the tubules, the total number of tubules, number of nodes, number of branch points, the number of tubes per node, and/or node area in a tubule formation assay. In one example, AngioApplication™ is a computer implemented automated analysis used to analyze the morphology of the cell lines. AngioApplication™ is an image-analysis software that automatically quantifies morphological parameters in assays involving formation of vasculature. The program reports the total area of the tubules, the total number of tubules, number of nodes, number of branch points, the number of tubes per node, or node among other parameters. This software utilizes the freely available NIH ImageJ library (Rasband, W. S., ImageJ, U.S. National Institutes of Health, Bethesda, Md., USA, available on the world wide web at rsb.info.nih.gov/ij; Abramoff et al., *Image Processing with ImageJ*, Biophotonics International 11:7, 36-42, 2004). As the program is coded in Java it can potentially be used in any computer platform (for example Windows, Macintosh, Unix, Linux, etc.). This program allows for the rapid/automated quantification of angiogenesis assays thus enhancing the capabilities of existing technologies for robust drug screening, patient diagnosis, and assessment of biologically active angiogenic or antiangiogenic drugs in patient samples.

Figure 15:
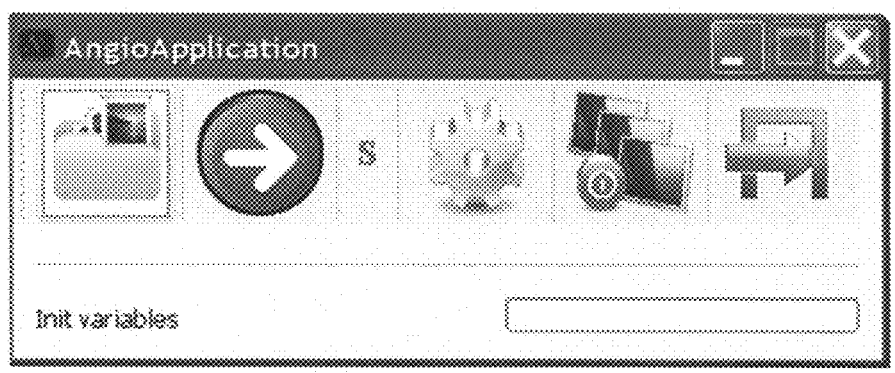
FIG. 15 is a digital image of a screen shot of the main GUI window of the AngioApplication™.
Figure 16:
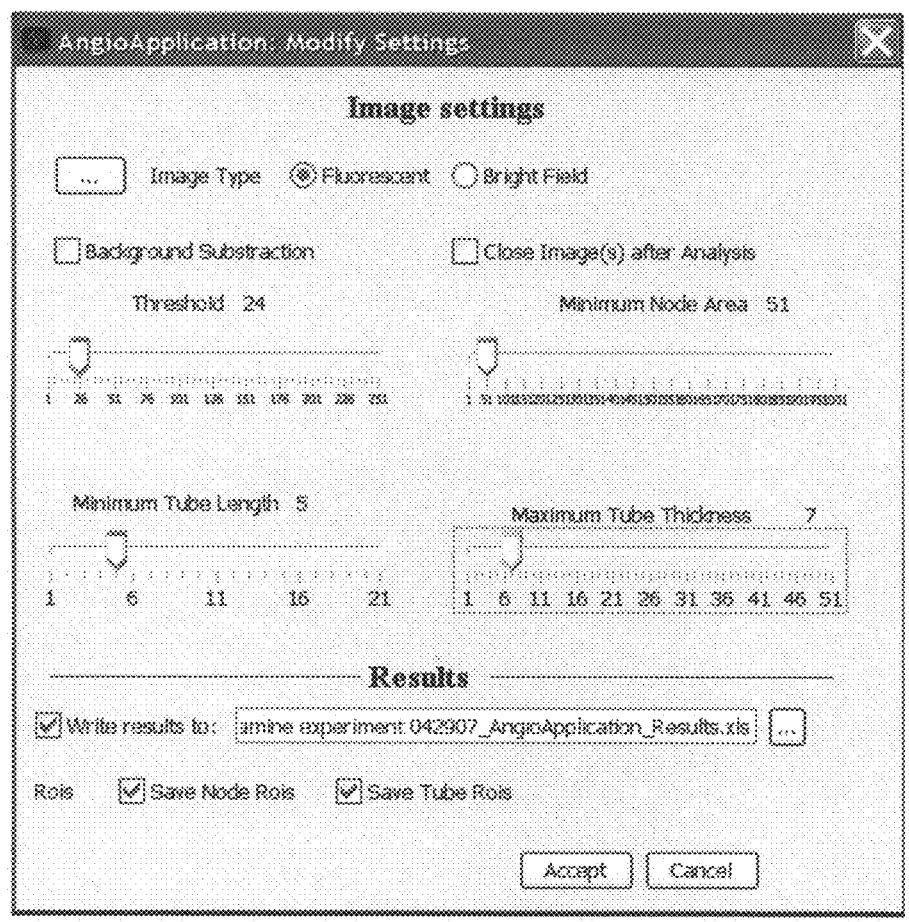
FIG. 16 is a digital image of a screen shot of the settings window of AngioApplication™.
Figure 17A:
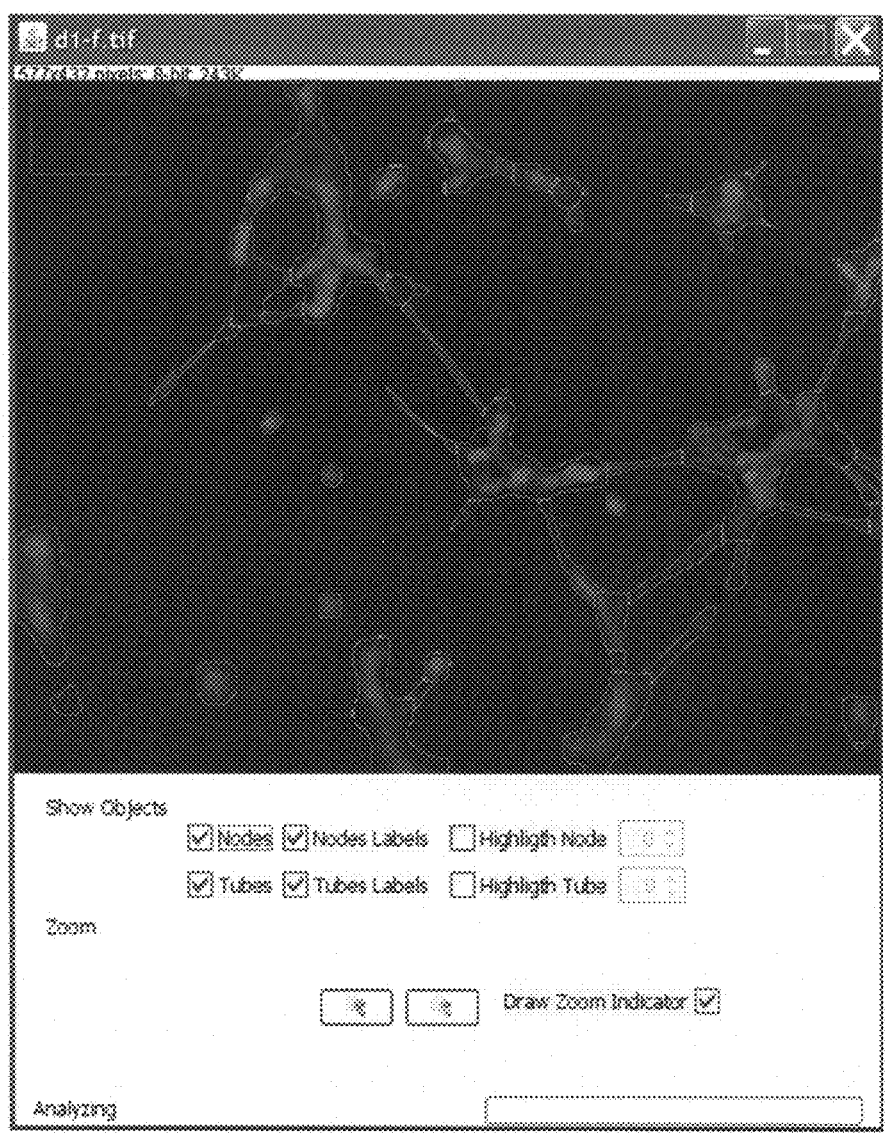
FIG. 17A is a digital image of a screen shot of the AngioApplication™ tubule analysis screen showing a sample under fluorescent illumination.
Figure 17B:
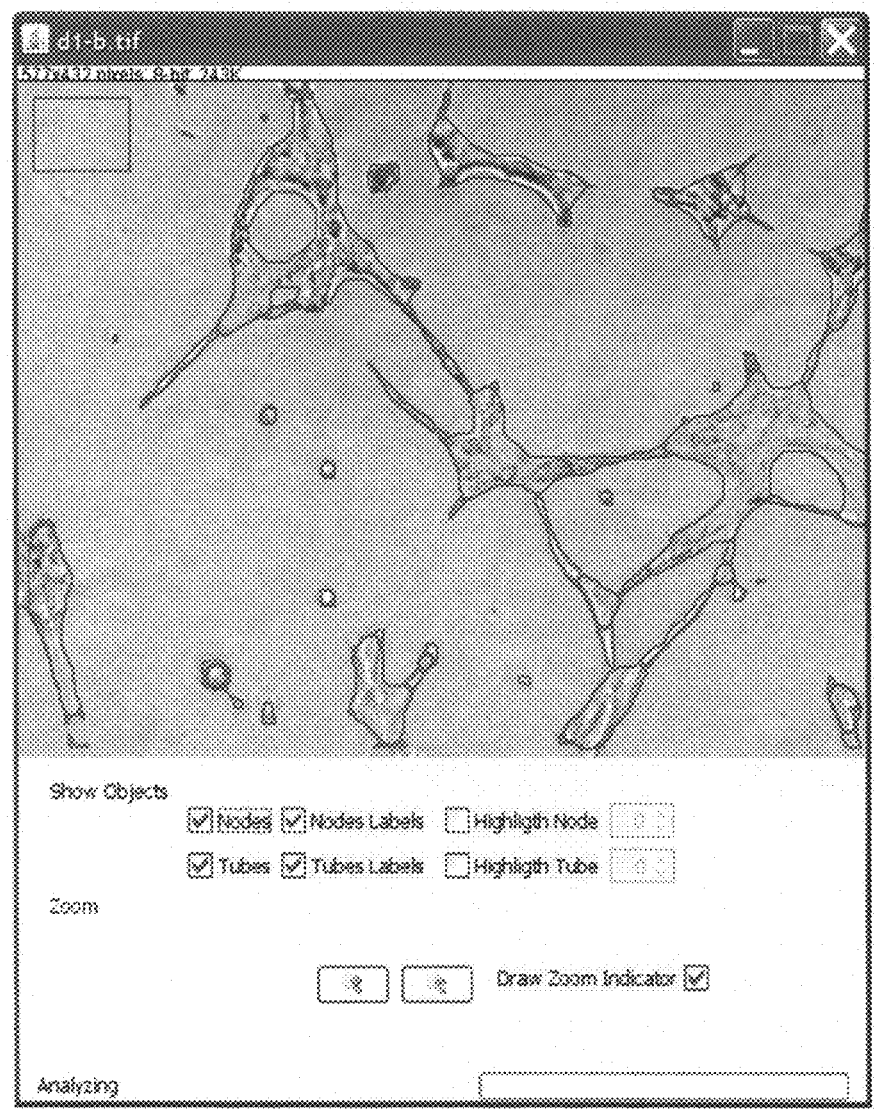
FIG. 17B is a digital image of a screen shot of the AngioApplication™ tubule analysis screen showing a sample under bright field illumination.
Figure 18:
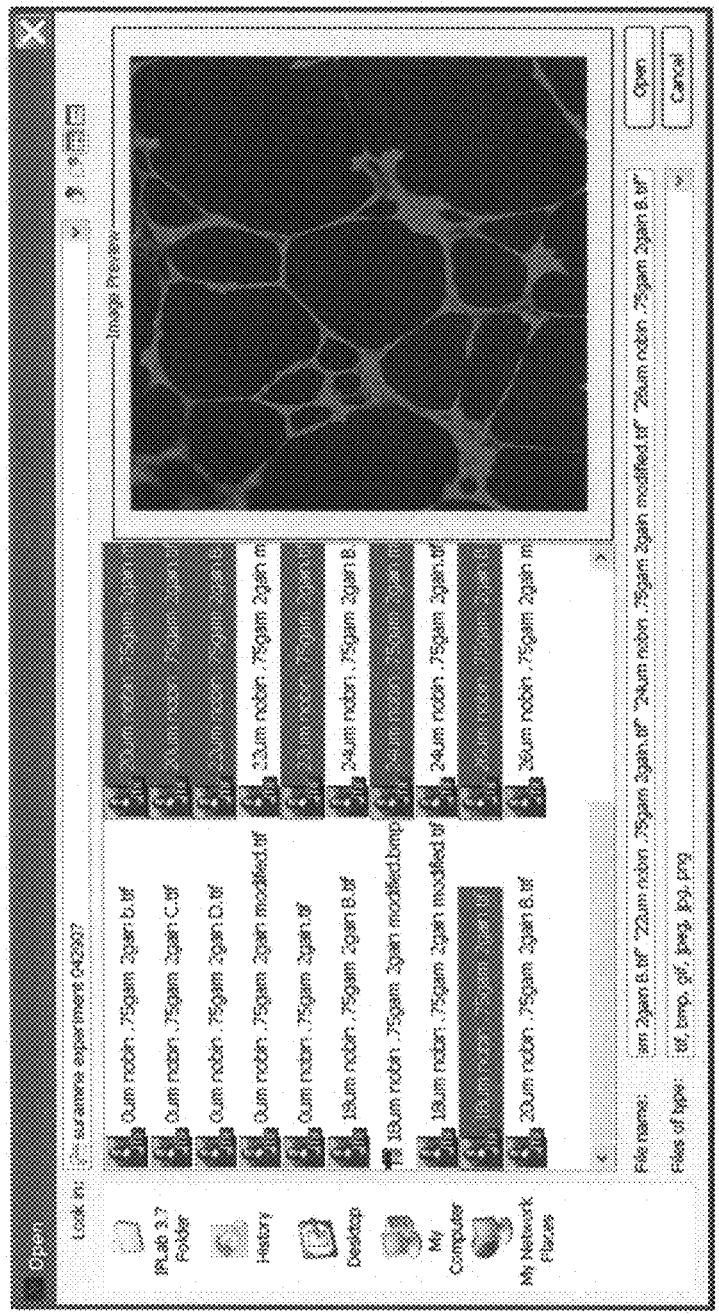
FIG. 18 is a digital image of a screen shot of the AngioApplication™ custom open dialog.
Figure 19:
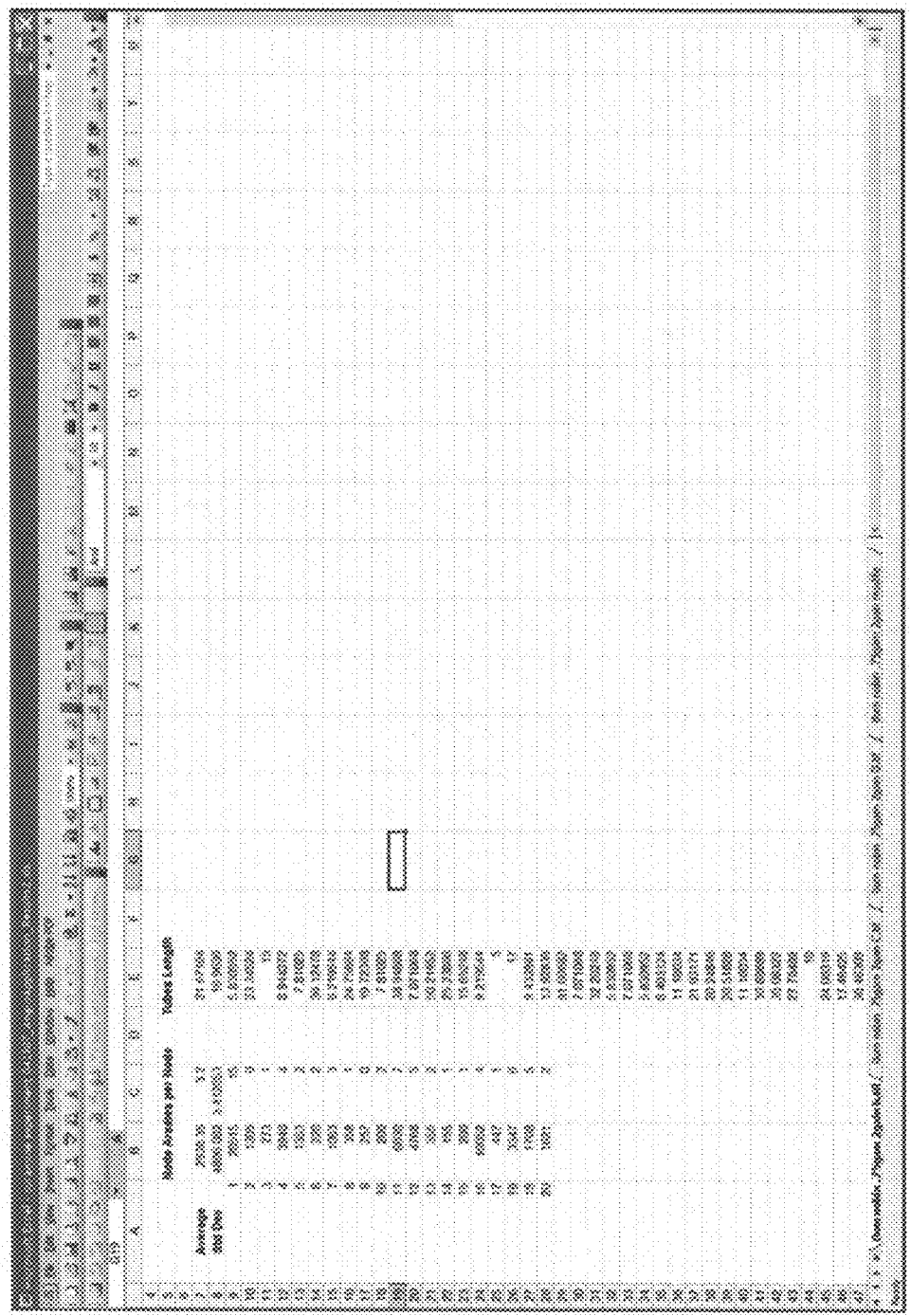
FIG. 19 is a digital image of a screen shot of the excel output of the AngioApplication™.

As shown in FIG. 15, the AngioApplication™ graphical user interface (GUI) which allows the user to choose the image (or batch of images) to be analyzed. The settings window of AngioApplication™ (see FIG. 16) allows the user to dynamically adjust several parameters to allow for a more precise analysis of the morphological features of the image, for example total length of the tubules, the total area of the tubules, the total number of tubules, number of nodes, number of branch points, the number of tubes per node, and/or node area. The program has been designed to find tubes and nodes in the original image and produce an "overlay" which shows both structures colored differently (see for example FIG. 17A and FIG. 17B). As shown in FIG. 17A and FIG. 17B both fluorescent images (FIG. 17A) and bright field images (FIG. 17B) can be analyzed. Images can be stored for later analysis (see FIG. 18) and the data generated by AngioApplication™ are stored directly into an Excel file (see FIG. 19).

D. Exemplary Test Agents

The methods disclosed herein are of use for identifying test agents that are modulators of angiogenesis. A "test agent" is any substance or any combination of substances that is useful for achieving an end or result. The test agents identified using the methods disclosed herein can be of use for affecting the normal angiogenic potential of a fluorescent cell line. Any test agent that has potential (whether or not ultimately realized) to affect the angiogenic potential of the fluorescent cell lines disclosed herein can be tested using the methods of this disclosure.

Exemplary test agents include, but are not limited to, peptides such as, soluble peptides, including but not limited to members of random peptide libraries (see for example, Lam et al., *Nature*, 354:82-84, 1991; Houghten et al., *Nature*, 354:84-86, 1991), and combinatorial chemistry-derived molecular library made of D- and/or L-configuration amino acids, phosphopeptides (including, but not limited to, members of random or partially degenerate, directed phosphopeptide libraries; for example, Songyang et al., *Cell*, 72:767-778, 1993), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof), small organic or inorganic molecules (such as, so-called natural products or members of chemical combinatorial libraries), molecular complexes (such as protein complexes), or nucleic acids.

Appropriate tests agents can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

Libraries (such as combinatorial chemical libraries) useful in the disclosed methods include, but are not limited to, peptide libraries (for example see U.S. Pat. No. 5,010,175; Furka, *Int. J. Pept. Prot. Res.*, 37:487-493, 1991; Houghton et al., *Nature*, 354:84-88, 1991; and PCT Publication No. WO 91/19735), encoded peptides (see for example PCT Publication WO 93/20242), random bio-oligomers (see for example PCT Publication No. WO 92/00091), benzodiazepines (see for example U.S. Pat. No. 5,288,514), diversomers such as hydantoins, benzodiazepines and dipeptides (see for example Hobbs et al., *Proc. Natl. Acad. Sci. USA*, 90:6909-6913, 1993), vinylogous polypeptides (see for example Hagihara et al., *J. Am. Chem. Soc.*, 114:6568, 1992), nonpeptidal peptidomimetics with glucose scaffolding (see for example Hirschmann et al., *J. Am. Chem. Soc.*, 114:9217-9218, 1992), analogous organic syntheses of small compound libraries (see for example Chen et al., *J. Am. Chem. Soc.*, 116:2661, 1994), oligocarbamates (see for example Cho et al., *Science*, 261:1303, 1003), and/or peptidyl phosphonates (see for example Campbell et al., *J. Org. Chem.*, 59:658, 1994), nucleic acid libraries (see Sambrook et al. *Molecular Cloning, A Laboratory Manual*, Cold Springs Harbor Press, N.Y., 1989; Ausubel et al., *Current Protocols in Molecular Biology*, Green Publishing Associates and Wiley Interscience, N.Y., 1989), peptide nucleic acid libraries (see for example U.S. Pat. No. 5,539,083), antibody libraries (see for example Vaughn et al., *Nat. Biotechnot*, 14:309-314, 1996; PCT App. No. PCT/US96/10287), carbohydrate libraries (see for example Liang et al., *Science*, 274:1520-1522, 1996; U.S. Pat. No. 5,593,853), small organic molecule libraries (see for example benzodiazepines, Baum, C&EN, January 18, page 33, 1993; isoprenoids, U.S. Pat. No. 5,569,588; thiazolidionones and methathiazones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514) and the like.

Libraries useful for the disclosed screening methods can be produced in a variety of manners including, but not limited to, spatially arrayed multipin peptide synthesis (see for example Geysen, et al., *Proc. Natl. Acad. Sci.*, 81(13):3998 4002, 1984), "tea bag" peptide synthesis (see for example Houghten, *Proc. Natl. Acad. Sci.*, 82(15):51315135, 1985), phage display (see for example Scott and Smith, *Science*, 249:386-390, 1990), spot or disc synthesis (see for example Dittrich et al., *Bioorg. Med. Chem. Lett*, 8(17):23512356, 1998), or split and mix solid phase synthesis on beads (see for example Furka et al., *Int. J. Pept. Protein Res.*, 37(6):487 493, 1991; Lam et al., Chem. Rev., 97(2):411-448, 1997). Libraries may include a varying number of compositions (members), such as up to about 100 members, such as up to about 1000 members, such as up to about 5000 members, such as up to about 10,000 members, such as up to about 100,000 members, such as up to about 500,000 members, or even more than 500,000 members.

In one convenient embodiment, high throughput screening methods involve providing a combinatorial chemical or peptide library containing a large number of potential therapeutic compounds. Such combinatorial libraries are then screened in one or more assays as described herein to identify those library members (particularly chemical species or subclasses) that display a desired characteristic activity (such as in an increase or decrease in tubule formation). In one example a test agent of use is identified that increases the number of tubules formed. In another example a test agent of use is identified that inhibits tubule formation, for example by decreasing the relative number of tubules formed.

The compounds identified using the methods disclosed herein can serve as conventional "lead compounds" or can themselves be used as potential or actual therapeutics. In some instances, pools of candidate agents may be identify and further screened to determine which individual or subpools of agents in the collective have a desired activity.

E. Therapeutic Compounds, Formulations and Treatments

This disclosure further relates to methods for modulating angiogenesis in a subject. The disclosed methods can identify compounds that modulate angiogenesis. The compounds and derivatives thereof are particularly useful for modulating angiogenesis in a subject, such as a subject suffering from a disease or condition accompanied by deregulated angiogenesis, for example cancer. The methods of modulating angiogenesis include administering to a subject a therapeutically effective amount of a test agent identified as one that modulates angiogenesis. Thus in some embodiments, the pharmaceutical compositions containing a test agent that decreases angiogenesis is administered to a subject, such as a subject with cancer. In some embodiments, the subject is a human subject. It is also contemplated that the compositions can be administered with conventional treatments for cancer, such as in conjunction with a therapeutically effective amount chemotherapeutic agent.

In some examples, a subject is selected for treatment with an angiogenesis modulator that increases angiogenesis. Such a subject can be treated with a test agent identified by the methods disclosed herein that increase angiogenesis. In some embodiments, the subject is a human subject.

Therapeutic compound(s) can be administered directly to a subject for example a human subject. Administration is by any of the routes normally used for introducing a compound into ultimate contact with the tissue to be treated. The compounds are administered in any suitable manner, optionally with pharmaceutically acceptable carrier(s). Suitable methods of administering therapeutic compounds are available and well known to those of skill in the art, and although more than one route can be used to administer a particular composition, a particular route can often provide a more immediate and more effective reaction than another route.

When the test agent is to be used as a pharmaceutical, the test agent is placed in a form suitable for therapeutic administration. The test agent may, for example, be included in a pharmaceutically acceptable carrier such as excipients and additives or auxiliaries, and administered to a subject. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, nontoxic excipients, including salts, preservatives, buffers and the like, as described, for instance, in *Remington's Pharmaceutical Sciences,* 15th ed., Easton: Mack Publishing Co., 1405-1412, 1461-1487, 1975, and *The National Formulary XIV.,* 14th ed., Washington: American Pharmaceutical Association, 1975). The pH and exact concentration of the various components of the pharmaceutical composition are adjusted according to routine skills in the art. See *Goodman and Gilman The Pharmacological Basis for Therapeutics,* 7th ed.

The pharmaceutical compositions are in general administered topically, intravenously, orally or parenterally or as implants. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampoule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science,* 249:1527-1533, 1990, which is incorporated herein by reference.

For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units, and also by multiple administrations of subdivided doses at specific intervals.

A therapeutically effective dose is the quantity of a compound according to the disclosure necessary to prevent, to cure or at least partially ameliorate the symptoms of a disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman and Gilman: the Pharmacological Bases of Therapeutics,* 8th ed., Pergamon Press, 1990; and *Remington's Pharmaceutical Sciences,* 17th ed., Mack Publishing Co., Easton, Pa., 1990. Effectiveness of the dosage can be monitored by any method.

F. Detection

The disclosed fluorescent cell lines can be detected by detecting the presence of the emission spectrum of the fluorescent proteins expressed by the fluorescent cell lines, for example using appropriate filters and/or monochrometers, (for excitation, emission, or both) the different fluorescent proteins can be detected using fluorescence microscopy and by FACS. However, it will be readily understood by those of skill in the art that other means for detecting the presence of fluorescent proteins and thus the cells expressing such protein may also be used.

Separate populations of fluorescent proteins with different emission spectra can be used to identify the cells containing such proteins, such as the disclosed fluorescent cell lines. For example, the characteristic emissions from the different fluorescent proteins can be observed as colors or can be decoded to provide information about the particular wavelength at which the emission is observed, for example to identify the number of cells of a particular kind or the location of such cell. Methods and devices for eliciting and detecting emissions from fluorescent proteins are well known in the art. In brief, a light source typically has a range that emits light at a wavelength shorter than the wavelength to be detected is used to elicit an emission by the fluorescent proteins. Numerous such light sources (and devices incorporating such light sources) are known in the art, including without limitation: deuterium lamps and xenon lamps equipped with filters, continuous or tunable gas lasers, such as argon ion, HeCd lasers, solid state diode lasers (for example, GaN, GaAs lasers), YAG and YLF lasers and pulsed lasers. The emissions of fluorescent proteins can similarly be detected using known devices and methods, including without limitation, spectral imaging systems. Optionally, the emissions are passed through one or more filters or prisms prior to detection. The simultaneous multicolor wavelength, such as multicolor, identification of fluorescent proteins permits rapid identification of cell without requiring fixation of the cells.

G. Kits and High Throughput Systems

This disclosure also provides kits including one or more of the fluorescent cell lines disclosed herein. Such kits can be used for the study of angiogenesis, for example to identify test agents that modulate angiogenesis, or the impact of mixed populations of cell types on angiogenic potential. The kits include at least one of the fluorescent cell lines disclosed herein. The kits may further include additional components such as instructional materials and additional reagents (for example serum, growth media and the like). The kits may also include additional components to facilitate the particular application for which the kit is designed (for example microtiter plates, optical filters and the like). Such kits and appropriate contents are well known to those of skill in the art. The instructional materials may be written, in an electronic form (such as a computer diskette or compact disk) or may be visual (such as video files). It is contemplated that the kits can contain reagents for carrying out the assays described herein, for example reagents for migration, proliferation, and/or tubule formation assays. In some examples, the kit also includes the AngioApplication™ program, for example supplied on a digital medium (such as a computer diskette or compact disk).

This disclosure also provides integrated systems for high-throughput screening of test agents for modulation of angiogenesis. The systems typically include a robotic armature that transfers fluid from a source to a destination, a controller that controls the robotic armature, a tag detector, a data storage unit that records tag detection, and an assay component such as a microtiter dish comprising a well having a cell culture, for example a cell culture containing one or more of the fluorescent cell lines disclosed herein.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous assays of fluorescent cell lines, for example the assay the effect of one or more test agents on angiogenesis.

Optical images can viewed (and, if desired, recorded for future analysis) by a camera or other recording device (for example, a photodiode and data storage device) and are optionally further processed such as by digitalizing, storing, and analyzing the image on a computer. A variety of commercially available peripheral equipment and software is available for digitizing, storing and analyzing a digitized video or digitized optical image, for example, using PC (Intelx86 or Pentium chip-compatible DOS™, OS2™ WINDOWS™, WINDOWS NT™ or WINDOWS95™ based computers), MACINTOSH™, or UNIX based (for example, a SUN™, a SGI™, or other work station) computers.

H. Three-Dimensional Co-Cultures

The stably-transfected fluorescent cells provided herein can be used to monitor the response of endothelial cells in a co-culture to one or more test agents, such as pharmaceutical agents. The detection of endothelial cell proliferation, motility and tubule formation in response to one or more test agents indicates the angiogenic effect of the test agent and can provide crucial information related to development of patient therapies. However, as described herein, endothelial cell responses to tumor cells co-cultured in two-dimensions (for example, separated by a layer of gel matrix such as a BME matrix) do not correlate with the in vivo angiogenic tumor activity.

To overcome deficiencies of 2D in vitro co-cultures, described herein are three-dimensional (3D) in vitro co-cultures that provide a mimetic of in vivo tumor activity. The co-cultures can be prepared in any suitable culture vessel or chamber, including multi-well or multi-chamber culture plates.

The 3D co-cultures described herein are prepared in three layers, which can be of any volume or thickness. The first layer, which is in contact with the bottom of the culture vessel, is any solidified polymer of neutral charge that is known to the art, and which does not alter the biological activity of the cells in culture. In particular examples, the polymer is a polysaccharide of neutral charge. In particular examples, the first layer comprises solidified agarose. In other examples, this layer comprises a neutral polysaccharide polymer of cellulose, curdlan, cellulose, starch, glycogen, chitin, and the like.

The second layer of the 3D co-cultures comprises a mixture of two or more types of cells embedded in an extracellular matrix gel extract or any suitable synthetic gel product. Exemplary extracellular matrix gels include BD MATRIGEL™ gel matrix (BD Bioscience), BME (Trevigen), GEL-TREX® gel matrix (Invitrogen), Collagen Type I/IV and the like. The gel matrix layer also comprises a mixture of endothelial cells that are dispersed (distributed) throughout the second layer and tumor cells. In particular examples, the endothelial cells can be any immortalized endothelial cell line, including the stably-transfected fluorescent endothelial cells described herein. In other examples, the endothelial cells are non-immortalized endothelial cell cultures that are transiently transfected with a fluorescent protein. The tumor cells can be derived from a cell line or from a tumor biopsy extracted from a subject. In particular embodiments, the tumor cells are in the form of a tumor spheroid colony. In other embodiments, the tumor cells are a piece of a tumor biopsy. The tumor cells can also be stably transfected to express a fluorescent protein.

In other examples, the second layer includes one or more additional mammalian cell types. Any cell type known to the art that is or might be part of the tumor microenvironment can be included in the gel matrix layer, for example, macrophages, mast cells, fibroblasts, adipocytes, and pericytes can all (independently or in combination) be included in the co-culture. In particular examples, multiple cell lines included in the second layer are transfected with constructs that express fluorescent proteins of distinguishable emission spectra.

The third layer of the 3D co-cultures is comprised of any suitable liquid culture medium, and is provided on top of the second layer. Any mammalian tissue culture media known to the art can be used; thus, a skilled artisan will understand the parameters that will influence selection and adaptation of media for cell growth.

In particular embodiments, one or more test agents, such as those described herein, is added to any layer of the co-culture, such as the first, second, or third layer of the co-culture. In particular examples, the test agent is added to the third layer of the co-culture. In particular examples, the test agent is one or more anti-angiogenic and/or anti-metastatic compound. In other examples, the test agent is a promoter of angiogenesis or metastasis. In some examples, the test agent directly affects angiogenesis, in the manner of drugs such as Avastin®. In other examples the test agent is one or more indirect anti-angiogenic compounds such as "non steroidal anti-inflammatory drugs" or NSAIDs.

In particular embodiments, the 3D co-cultures described herein are used to monitor the angiogenic or metastatic potential of tumor cells. Such methods involve preparing a 3D co-culture (in three layers, as described herein), incubating the co-culture for a period of time, and detecting endothelial cell proliferation or tubule formation, or angiotropism (for instance, using the assays described herein). In particular examples, the tumor cells are derived from a tumor removed from a subject and the 3D co-cultures can be used to assess the angiogenic or metastatic potential of the tumor. The co-culture can be incubated for any length of time necessary to observe the angiogenic or metastatic activity including incubation times from several hours (6, 7, 8, 9 or more hours) to several days (1, 2, 3, 4, 5, 6, 7, 8, 9, 10 or more days) to one, two or more weeks. The detection of endothelial cell proliferation, tubule formation, or angiotropism is achieved by fluorescence or standard microscopy alone or confocal laser scanning microscopy or in combination with the detection methods described herein. In particular embodiments, the methods of monitoring angiogenic or metastatic potential of tumor cells are used to determine the effects of at least one test agent on the angiogenic or metastatic potential of tumor cells derived from a subject. In such examples, the test agent may be a candidate therapeutic compound that may be used for treatment of the subject. In other examples, it may be a compound that has already been administered to a subject (either the same subject or a subject different from the subject from whom the tumor cells originated) as part of a cancer treatment regimen. In this way, the development of drug-resistance of a tumor and the efficacy of a treatment in a subject can be monitored by repeatedly using the 3D co-cultures over a period of time.

The development of 3D co-cultures that provide a mimetic of in vivo tumor activity also enables methods for selecting personalized anti-angiogenic and anti-metastatic therapies (that is, therapies that are selected in order to be specifically effective in a specific subject). These methods involve assaying the anti-angiogenic or anti-metastatic activity of a panel of compounds or other treatment variables (e.g., dosage, timing, etc.), alone or in combination, using a 3D co-culture that contains tumor cells from the specific subject. Such assays optionally can be done in a multi-well plate. 3D co-cultures are prepared as described using the target subject's tumor cells, and at least one test compound (test agent) is added to the third layer of each of some but not all of the 3D co-cultures. The co-cultures are incubated and angiogenic or metastatic activity is observed, for instance as described herein. The test agent (or dosage, or other variable regimen) that has the most beneficial (strongest) anti-angiogenic and/or anti-metastatic effect, for instance in comparison to the angiogenic or metastatic activity observed in the compound-free co-culture, is then selected for personalized treatment. The continued efficacy of such therapies can be monitored after any desired length of time, such as three months or longer if necessary.

In another embodiment, the 3D co-cultures can also be used in the development of computer programs to quantitate angiogenesis and vessel complexity in three-dimensional projections. Such programs would ultimately be applied to analyze the vascular network around tumors and determine a 3D vascular density profile for a given tumor via CAT or MRI scans. Such images could be retaken after initial anti-angiogenic drug therapy to quantitate treatment regimen efficacy before actually seeing alterations in tumor size.

EXAMPLES

Example 1

Generation of Stably Transfected Fluorescent Cells

This example describes the materials and methods used in the generation of stably transfected fluorescent cells.

Cell Lines.

Cell lines A549 (lung adenocarcinoma) and MCF-7 (breast cancer) were acquired though the DTP 60 cell line library at NCI/Frederick. RF/6A (ATCC CRL-1780) was obtained from the American Type Culture Collection as a *Macaca mulatta* (rhesus monkey) retina endothelial cell line but shown to be a monkey pericyte cell line via surface marker expression. The mast cell line HMC-1 was derived from primary mast cells exposed to 5-azacytindine, spontaneously immortalized and established by Dr. John Butterfield (Butterfield et al., *Leuk. Res.* 12:345-355, 1988) and was obtained from the Department of Internal Medicine, Division of Allergic Diseases, Mayo Clinic, Rochester Minn. 55905. Endothelial cell line HMEC-1 is a human dermal microvascular blood vessel endothelial cell line originally developed by Dr. Thomas Lawley (Emory University School of Medicine, Atlanta, Ga., USA) via SV40 large T transfection (Ades et al., *J. Invest. Dermatol.* 99:683-699, 1992), and was obtained from Dr. Hynda Kleinman (NIDCR). PAE is a porcine aortic endothelial cell line from Dr. Carl-Henrik Heldin (Ludwig Institute for Cancer Research, Uppsala, Sweden) that became spontaneously immortalized with continuous passaging (Rönnstrand et al. *EMBO J.* 11:3911-3919, 1992).

Plasmids.

Plasmids pmaxFP-GFP-C, pmaxFP-Yellow-C and pmax-Red-N were obtained from AMAXA® Inc. (Gaithersburg, Md.). Plasmids pDsRed2-C1 and pAmCyan1-C1 were obtained from BD Bioscience. pcDNA3.1-GFP was built in house inserting the GFP coding reading frame into the pcDNA3.1-TOPO-TA (INVITROGEN™) backbone. All plasmids contain a GENETICIN® selectable marker.

Transfections and Generation of Stable Transfectants.

Cell lines A549, MCF7, SK-LMS-1, 92-1, PC-12, HMEC-1, RF/6A (ATCC CRL-1780), PAE, and HMC-1 were stably transfected with the plasmids described above using a NUCLEOFECTOR™ II (AMAXA® Inc.). Different transfection solutions were used following manufacturer's suggestions if available (A549, MCF7, SK-LMS-1, 92-1, PC-12). For HMEC-1 and RF/6A (ATCC CRL-1780), AMAXA® HMVEC-L solution together with NUCLEOFECTOR™ II program T-023 were used. For HMC-1, AMAXA® solution V and NUCLEOFECTOR™ II program T-030 were used.

After transfection, cells were seeded in 6 well plates using the following media. A549, 92-1, and MCF7 cells were cultured in RPMI (INVITROGEN™, Carlsbad, Calif.) supplemented with 10% fetal bovine serum (FBS) (Hyclone, Logan, Utah), SK-LMS-1 cells were cultured in DMEM (INVITROGEN™, Carlsbad, Calif.), supplemented with 10% FBS (Hyclone, Logan, Utah), PC-12 cells were cultured in F-12K medium (INVITROGEN™, Carlsbad, Calif.), HMC-1 cells were cultured in Iscove's minimum medium (INVITROGEN™) supplemented with 10% FBS and 1.2 mmol/L of monothioglycerol (Sigma-Aldrich, St Louis, Mo.). HMEC-1 cells were cultured in EMB-2 (CLONETICS®, San Diego, Calif.) supplemented with EGM-2 MV SingleQuots® (CLONETICS®). PAE cells were cultured in DMEM/F12 1:1 medium (Invitrogen). RF/6A (ATCC CRL-1780) cells were cultured in RPMI (INVITROGEN™) supplemented with 10% FBS.

After 18 hours transfection efficiency was assessed under a fluorescent microscope and when considered appropriate (>40% transfection efficiency) cells were exposed to 800 µg/ml GENETICIN® (INVITROGEN™). For all cells types, antibiotic resistant clones showed a high range of fluorescence intensities including clones (high proportion in some cell types such as A549) which were negative. In order to enrich for positive clones and to obtain a more homogeneous population of fluorescent cells the cells were sorted by FACS gated on the fluorescent signal of the cells. In some cases, such as the A549 cells, several cycles of cell sorting were used to obtain a population stably transfected and with homogeneous fluorescence. Once cells were confirmed to be stable transfectants with homogeneous fluorescence levels map testing and mycoplasma testing were performed.

Example 2

Growth Assay

This example describes exemplary procedures for measuring the growth of the cell lines disclosed herein as either monocultures or co-cultures of two or more cell lines.

Co-cultures of different cell lines were performed, with each cell line expressing a different fluorophore than the other (for example MCF7-RFP expressing red fluorescent protein and PAE-YFP expressing yellow fluorescent protein). The co-cultures were grown in black, clear bottom Costar 96-well plates (Corning Costar Corp., Cambridge, Mass.). A direct relationship between fluorescence and number of cells in culture was established for all different fluorescent cell lines tested (see for example FIG. 2).

Different densities of cells were used in different trials. Fluorescence intensity was obtained using an INFINITET™ M200 (TECAN® Group Ltd. Switzerland) fluorometer. The spectra for the different fluorophores used overlap at maximum excitation/emission. In order to avoid spectral bleed through and discriminate fluorescence from different cells types, two systems were used. In the first system measurements were taken at suboptimal emission/excitation wavelengths ensuring no overlap. Precisely gated fluorescence emission and excitation wavelengths allowed the complete discrimination of fluorescence emitted by different cell types in a co-culture. As shown in FIG. 3A, when fluorescence emission is measured in the yellow range, only the cells emitting in the yellow range (i.e. PAE endothelial cells expressing YFP) show a linear relationship with the number of cells, while cell emitting in the red range (i.e. MCF7 cells expressing RFP) do not show such a relationship. As shown in FIG. 3B, when fluorescence emission measurements are done in the red range, only cells emitting in that range (i.e. MCF7 cells expressing RFP) show a linear relationship with cell number.

Figure 5:
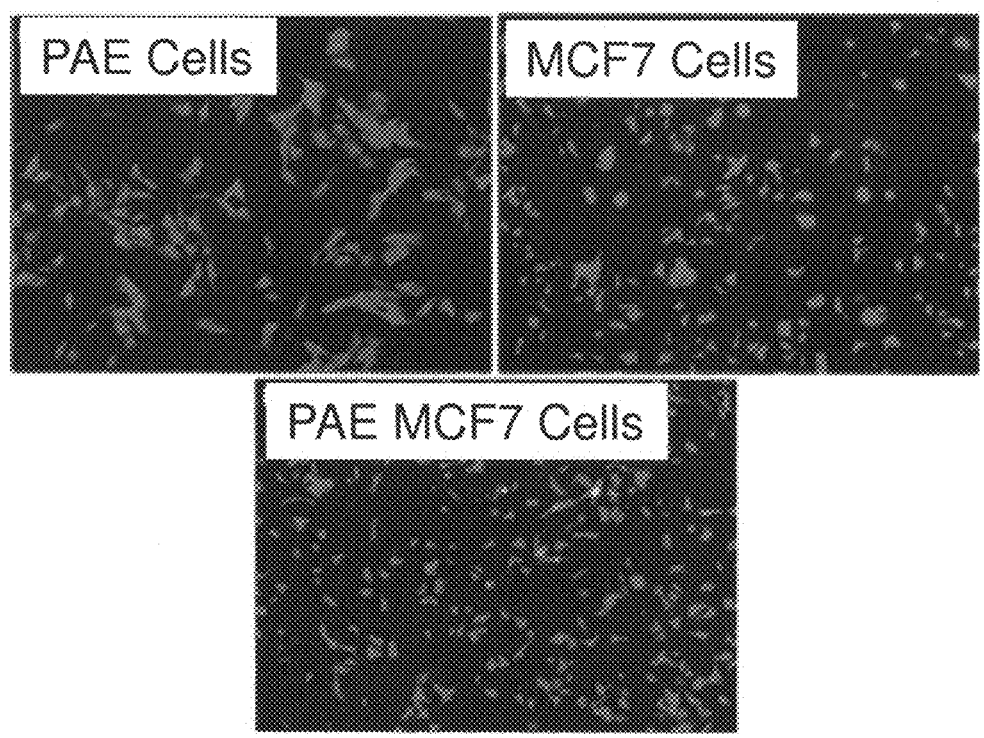
FIG. 5 is a set of digital images of YFP expressing PAE endothelial cells and RFP expressing MCF7 breast cancer cells in mono-culture and co-culture.
Figure 6:
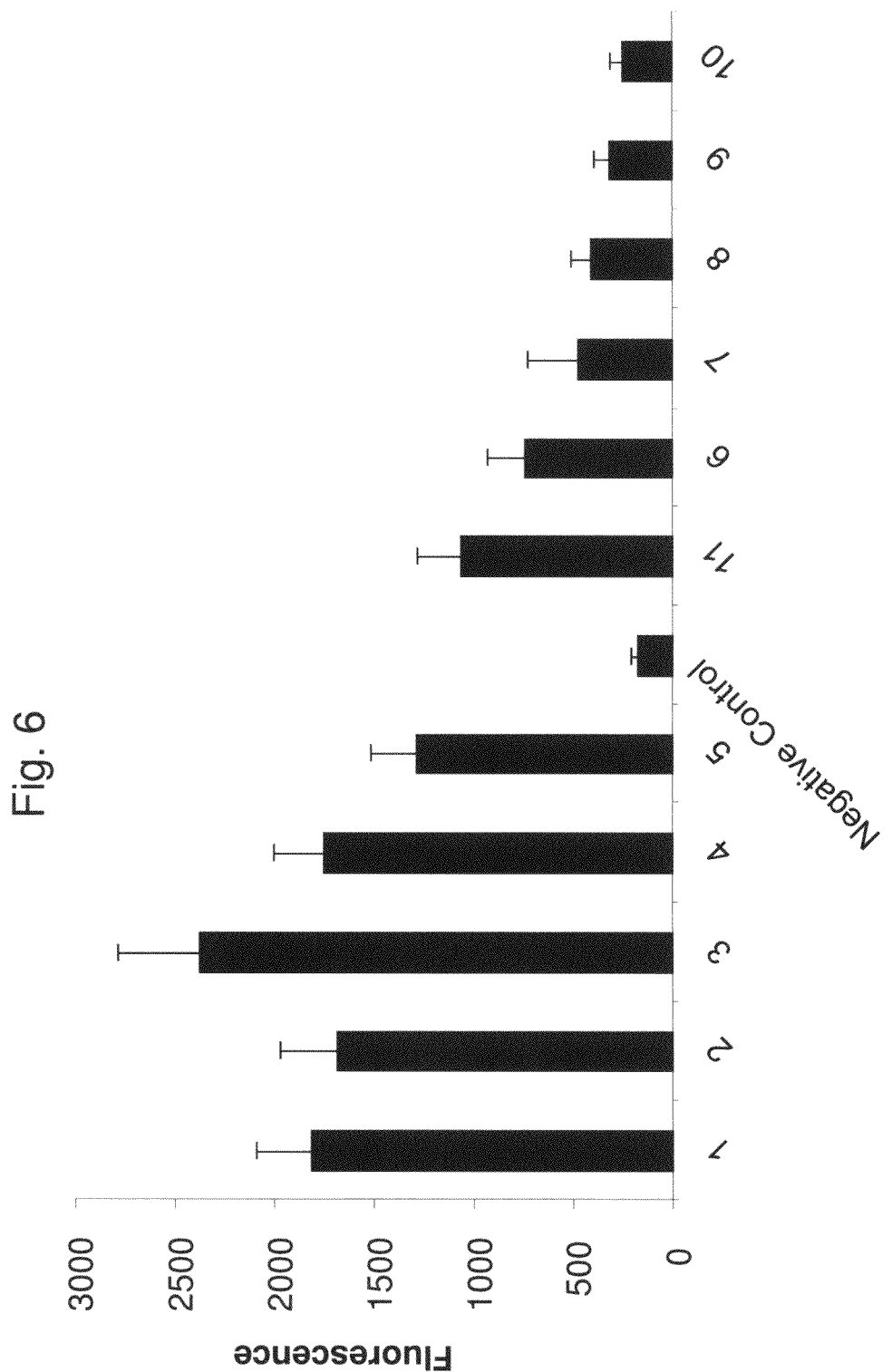
FIG. 6 is a bar graph of the migratory potential of serum obtained from 11 subjects and a negative control.

In the second system measurements obtained at maximum excitation/emission were corrected through spectral linear unmixing using a modification of the ImageJ algorithm first implemented by Dr. Joachim Walter (the program is available on the world wide web at rsb.info.nih.gov/ij/plugins/spectral-unmixing.html); based on the work by Timo Zimmermann (Zimmermann, "Spectral imaging and linear unmixing in light microscopy" *Adv Biochem Eng Biotechnol*, 95: 245-265, 2005). The fluorescent cells were also examined under a fluorescent microscope allowing for morphological analysis and comparison of mono-cultures versus co-cultures, as shown in FIG. 5. Continuous real time readings were carried out to assay the growth of mono- and co-cultures of PAE and MCF7 cells (see for example FIGS. 4A and 4B).

Example 3

Tubule Formation Assay

This example describes exemplary procedures for measuring the ability of the cell lines disclosed herein for tubule formation potential. 50 μl of low growth factor BME (Basement Membrane Extract, Trevigen, Inc. Gaithersburg, Md.) were laid down in each well and the plate was incubated for 1 hour at 37° C. The extract gels at 37° C. to form a reconstituted basement membrane and stimulates tubule formation by endothelial cells. The major components of the Basement Membrane Extract (BME) include laminin I, collagen IV, entactin, and heparin sulfate proteoglycan. 15,000 PAE-GFP cells were then added on top of the gelled BME and images were acquired with a fluorescent microscope after 3.5-24 hours. Cells were imaged on the BD Pathway™ Bioimager. FIG. 7A shows the impact of increasing concentrations of suramin (an established inhibitor of tubule formation) (from 0 to 26 μM) on tubule formation by PAE green cells (GFP transfected). FIGS. 7B and 7C shows the dose response of PAE green cells to suramin in a tubule formation assay. As expected the suramin inhibited tubule formation and the EC50 calculated (~26 μM) is in agreement with the value previously published. Tubule formation assays were quantified using the Java based software AngioApplication™. AngioApplication™ has been specifically designed for the quantification of tubule formation assays. Several morphological parameters were assessed in images including the total area of the tubules, the total number of tubules, number of nodes, number of branch points, the number of tubes per node, or node.

AngioApplication™ was validated by comparison of the published EC50 value of suramin (~26 μM) and the EC50 value of suramin as determined experimentally using the disclosed fluorescent cell lines in a tubule formation assay. As shown in FIG. 7A increasing concentrations of suramin causes disruption of tubule formation. AngioApplication™ was used to automatically assess tube length at several concentrations of suramin. Traditionally quantification of tube formation was based in the measurement of complete (long) tubes in the image. AngioApplication™ determined that as the concentration of suramin was increased the number of long tubules was diminished. As shown in FIG. 7B, using AngioApplication™ the EC50 of suramin was determined to by approximately 26 μM, in close agreement with the published EC50 of suramin. In addition, because AngioApplication™ calculates the length for all tubes in the image (including incomplete tubes) a more refined analysis was performed using the measurement of short (or incomplete) tubules. Interestingly, AngioApplication™ found that the number of small tubes increased as a function of suramin concentration. This is in agreement with the fact that Suramin interferes with the mechanism of tube formation. As shown in FIG. 7C, the EC50 calculated for suramin using this additional parameter was approximately 26 μM. This result demonstrates that both measurements (short and long tubes) can be used to evaluate potency of antiangiogenic drugs and potentially other proangiogenic factors found in patient serum samples.

Example 4

Migration Assay

This example describes exemplary procedures for measuring the ability of the cell lines disclosed herein to migrate in response to a chemical stimulation. In this example migration is up a chemical gradient, from a region of lower concentration to higher concentration of a chemical attractant.

Migration assays were performed using the ChemoTx® 96 well cell migration system (Neuro Probes Inc.) following the manufacturer's recommendations. Every plate contained an internal negative (absence of stimulus) and a positive (presence of a known chemotactic substance) control together with wells containing different cell densities which allow for the construction of standard curves which mathematically correlate number of cells and fluorescence intensity. Different putative chemotactic factors were assayed using this system including plasma obtained from patients. Fluorescence measurements were obtained using an INFINITE™ M200 fluorescence plate reader to measure the accumulation of fluorescent cells in the lower chamber of the ChemoTx® 96 plate that had migrated through the membrane to the lower chamber in response to chemoattractant in the lower chamber. Migration can be quantitated and the relative migration determined by determining the intensity of the fluorescent signal, for example at the emission maxima, of the fluorescent cells in the lower chamber, wherein greater fluoresce intensity in the lower chamber relative to the control indicates that migration has occurred. The migration potential of various samples can be correlated with characteristics of the sample or the subject from which the sample was taken. In several examples, the fluorescent cells disclosed herein were tested for migratory potential in the presence of enhancers/blockers of migration.

Figure 8A:
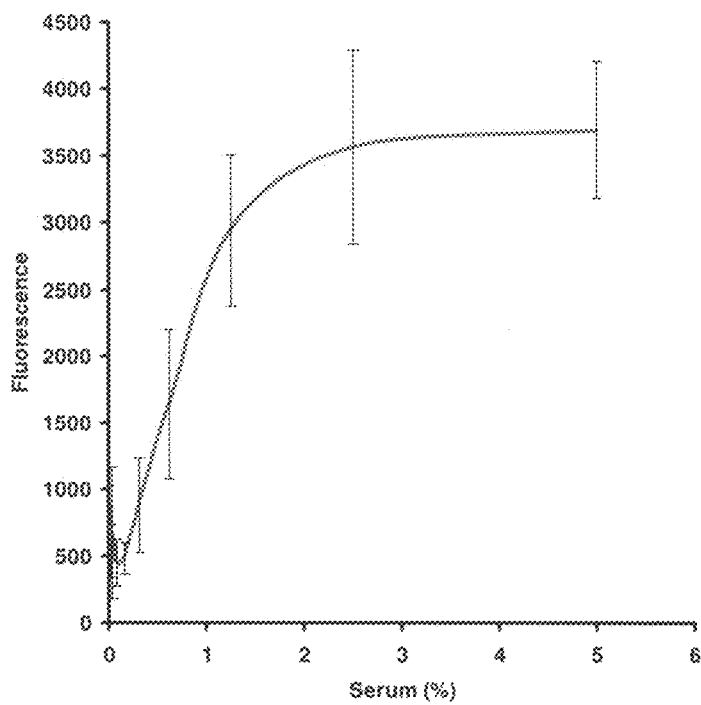
FIG. 8A is a graph showing the migratory potential of fluorescent endothelial cells in response to increasing concentrations of sputum obtained from an Idiopatic Pulmonary Fibrosis (IPF) patient.

Using this migration assay the presence of biologically active chemotactic factors in a sample can be tested. FIG. 8A shows the effect of decreasing human normal serum on the motility of YFP expressing PAE endothelial cells. PEA cells were placed on the upper membrane of the ChemoTx® 96 well cell migration plate. The migration of PAE cells to the lower chamber as a function of concentration of human normal serum was then determined using an INFINITE™ M200 fluorescence plate reader to measure the accumulation of fluorescent cells in the lower chamber. As expected, as the serum concentration increases (and therefore the presence of chemotactic factors increases in the serum) higher levels of fluorescence are detected, which are directly related to the migratory capacity of the cells. This assay was also directly applied to the assessment of the migratory potential of patients' serum samples. FIG. 8 shows a study wherein the serum of different patients with or without tumors and with or without treatments was screened for induced migratory potential. As expected all samples show higher induced migratory potential than the negative control (un-stimulated cells). For example, greater or less migratory potential can be correlated with the presence or absence of tumors or tumor types.

Figure 8B:
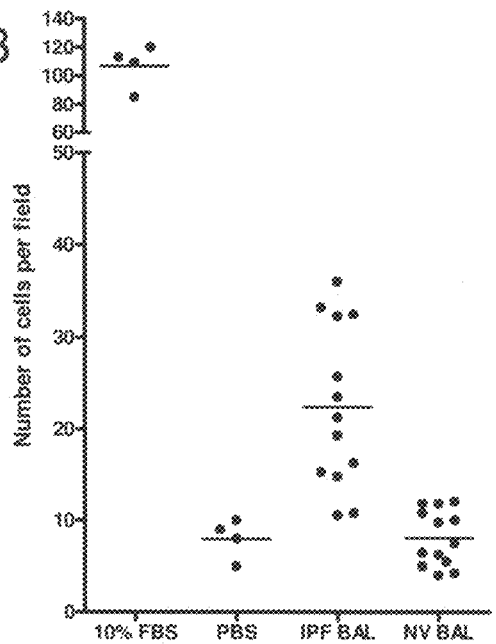
FIG. 8B is a graph showing the difference in migration potential of sputum from 13 normal subjects (NV-BAL) and 13 IPF patients (IPF-BAL) (10% fetal bovine serum (FBS) and phosphate buffered saline (PBS) are controls).
Figure 11:
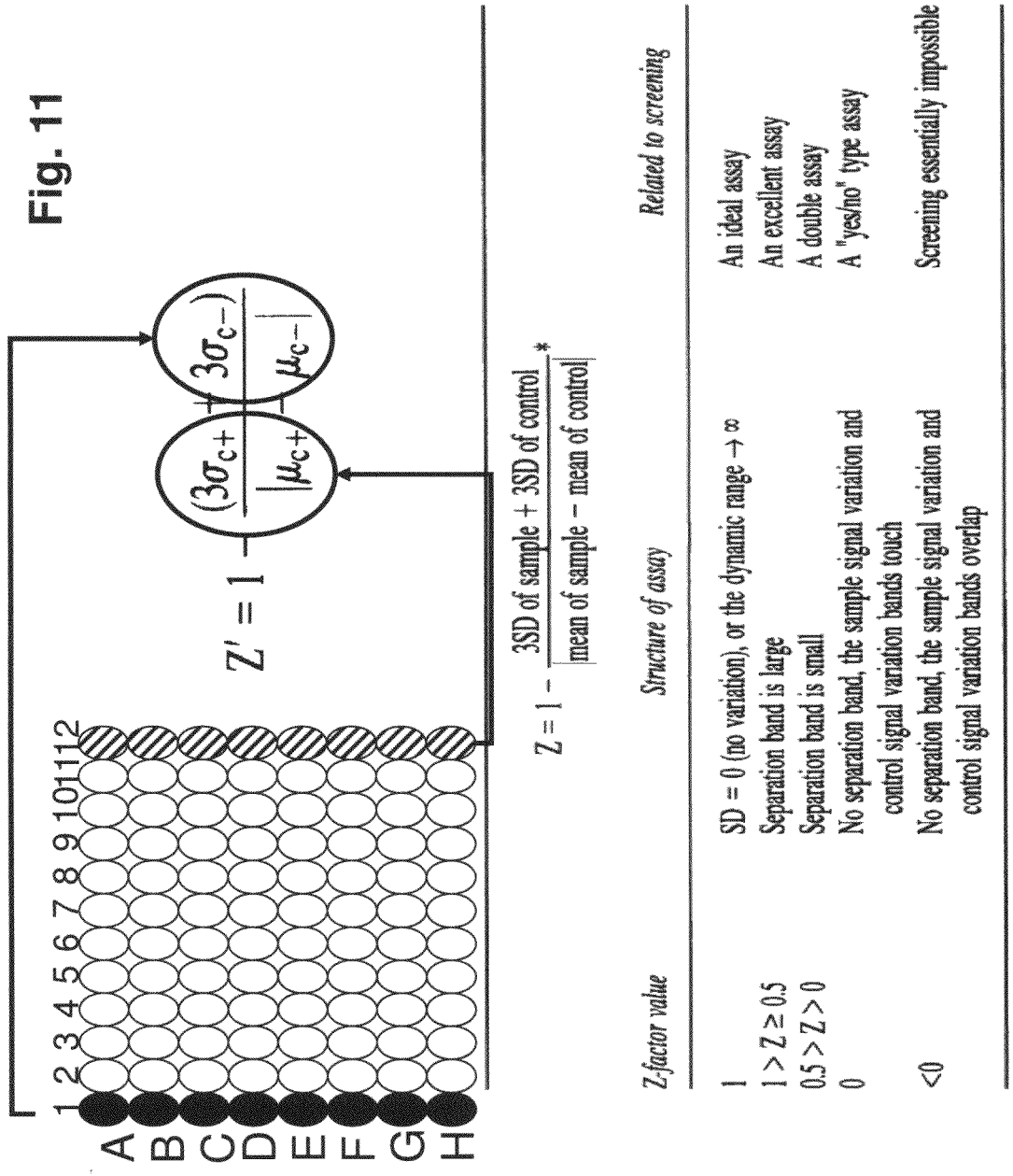
FIG. 11 shows an exemplary procedure for determining antiangiogenic activity of a test agent in a multiwell format. In this example, assays are performed in 96-well plates which contain negative controls (column 1) positive controls (column 12) and 80 remaining wells containing the small molecules to be tested. In some examples, a quality control (Z' score, Zhang et al. *J. Biomol. Screen.* 4:67-73, 1999) is applied to every plate. Only plates with Z values between 0.5 and 1 are considered.

FIGS. 11A and 11B shows the applicability of the endothelial fluorescent cells to assess the angiogenic status of clinical samples. In this case the migratory potential of the sputum from Idiopathic Pulmonary Fibrosis (IPF) patients was tested to determine the effect of the sputum on the migratory potential of PAE cells expressing fluorescent protein. This example assesses whether angiogenic factors are present in this type of sample and can be used in combination with the experimental procedures described in this patent application as a diagnostic/prognostic end point. Sputum obtained from the patients was placed in the lower chamber of the ChemoTx® 96 well cell migration system. The migration of PAE cells through the membrane to the lower chamber in response to the sputum was then determined using an INFINITE™ M200 fluorescence plate reader to measure the accumulation of fluorescent cells in the lower chamber. First, a standard curve was generated with one of the samples from an IPF patient demonstrating that it contains chemotactic factors for endothelial cells (see FIG. 8A). Subsequently, sputum obtained from 13 normal subjects was compared to sputum obtained from 13 IPF patients (see FIG. 8B). As shown in FIG. 8B, sputum from normal subjects does not induce migration above the phosphate buffered saline (PBS) control. However, samples from IPF patients showed a strong migratory potential.

This assay provides a fast and reliable system to detect the presence of biologically active enhancers (for example tumor-derived enhancers), or suppressors (for example test agents, such as drugs) of cellular migration in patients' samples.

Example 5

Cell Viability Assay

This example describes exemplary procedures for measuring the cytotoxicity of an agent on the cell lines disclosed herein.

Figure 9:
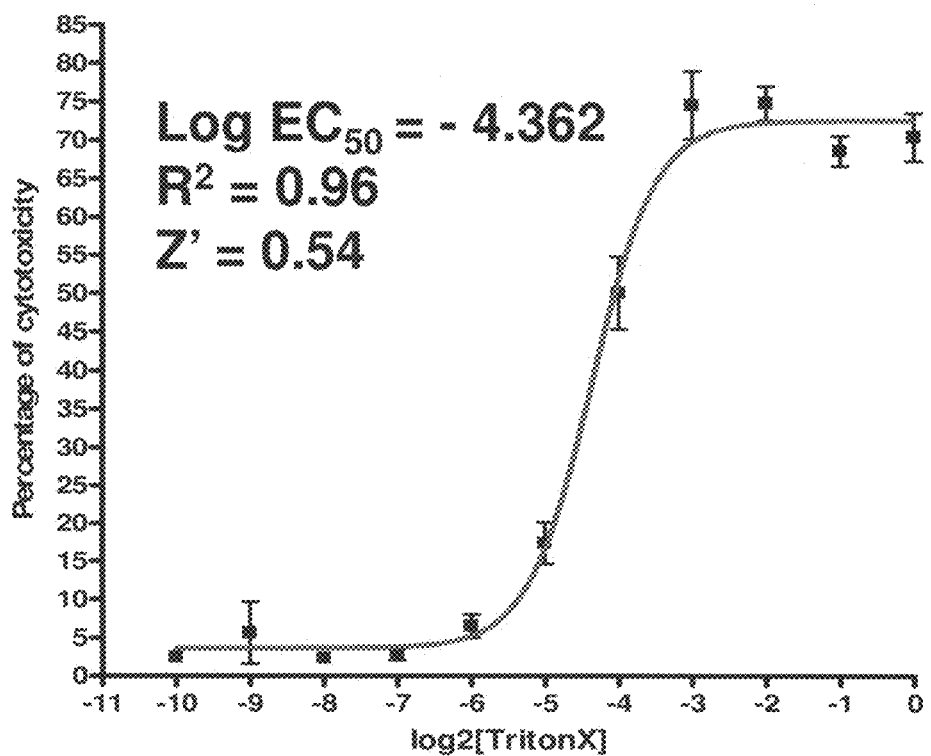
FIG. 9 is a graph of the measured fluorescence present in the cellular growth media as a function of increasing TritonX concentration.

Increasing concentrations of Triton® X were added to fluorescent cells and after 20 minutes supernatants were collected and transferred to a different plate and measured at the appropriate wavelength. As shown in FIG. 9, the relative fluorescence as a function of the log of concentration produces a sigmoidal curve correlating the amount of Triton® X to the percentage of cytotoxicity. Using standard curve fitting software (such as a KaleidaGraph® available from Synergy Software) the EC50 and other parameters commonly used to assess cytotoxicity can be calculated.

Example 6

Exemplary Screen of Small Molecules as Modulators of Angiogenesis

Figure 10:
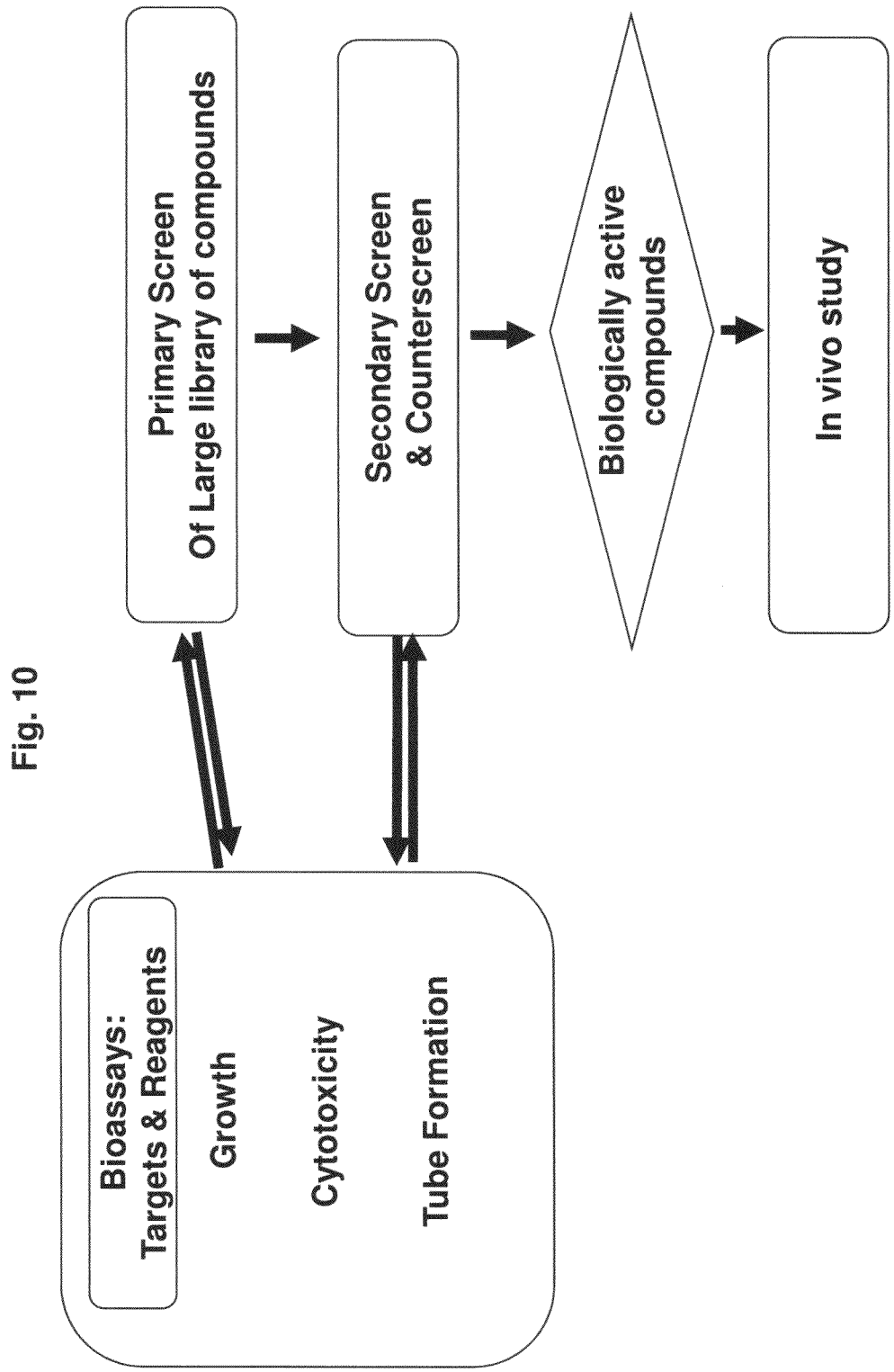
FIG. 10 is a flow chart showing an exemplary method for high throughput screening of test agents (such as small molecules) for antiangiogenic activity using fluorescent endothelial cells. In one example, a primary screen of a small molecule library is done using the disclosed growth and tube formation assays. This primary screen identifies bioactive compounds, some of which could be cytotoxic. A counter-screen using the disclosed cell viability assay is used identify those compounds with cytotoxic activity. Biologically active compounds which show no cytotoxicity are considered putative antiangiogenic candidates and can move forward to in vivo studies.

This example describes exemplary procedures for screening of test agents as modulators of angiogenesis. A flow-chart representation of an exemplary implementation of a screening procedure is shown in FIG. 10. As shown in FIG. 10 a primary screen of a library of small molecules is done using growth and tube formation assays (exemplified above in Examples 2 and 3). This primary screen identifies antiangiogenic compounds which in some cases are cytotoxic. A counterscreen using the disclosed cell viability assay (as exemplified in Example 5) is performed to determine those compounds that are cytotoxic. Antiangiogenic compounds which show little or no cytotoxicity are considered putative antiangiogenic candidates and move forward to in vivo studies.

Figure 12:
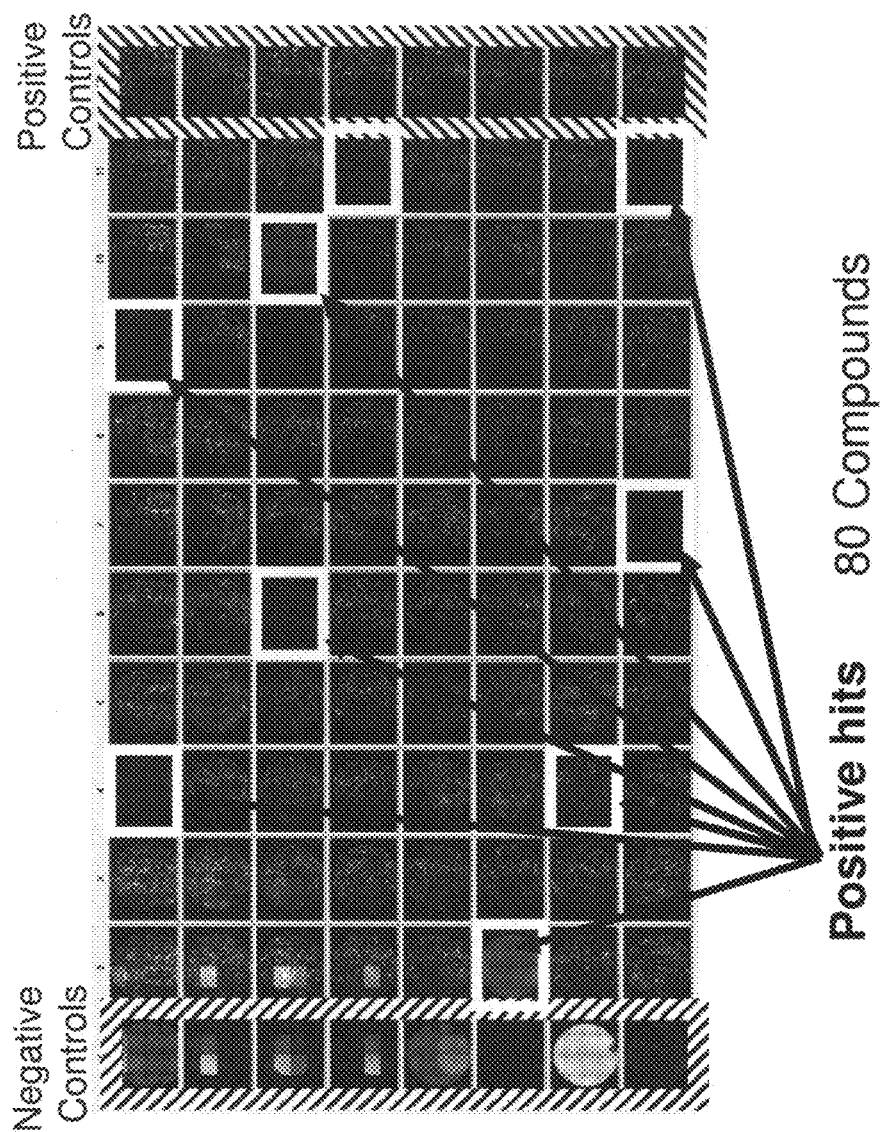
FIG. 12 shows a montage of micrographs representing an example of one of the growth assay plates included in an exemplary high throughput screen. Column 1 contains cell that have not been stimulated with growth factor (no growth) and column 12 shows growth of the endothelial cells upon exposure to a growth factor cocktail. Test wells show different levels of cell growth (quantification of the fluorescence in each well is done with a fluorimeter). Wells which contain growth inhibitors are shown in white boxes (hits are defined using the SASD: sum of the average squared inside-cluster distances, Gagarin et al, *J. Biomol. Screen* 11:1-12, 2006).

In some examples, the growth of a cell line of interest is determined in the presence of a test agent. In some example, the growth of a mixture of cell lines of interest is determined in the presence of a test agent. In some examples, this is done in a multiwell format, such as a 96 well plate or a 384 well plate. For example (as exemplified in FIG. 11), the assays are performed in 96 well format which contains negative controls (column 1), positive controls (column 12) and 80 wells containing the small molecules to be tested. A sample containing a mixture of the fluorescent cell lines disclosed herein is provided in the wells of the multiwell plate. Test agents are added to the plate either at a single concentration or at graded concentrations, for example from about 1 picomolar to about 100 millimolar. The growth of the cells in the presence of the test agent is determined, for example by determining the fluoresce signal attributable to the fluorescent cell line of interest in the well as compared to a control, for example a control well in which no test agent has been added. FIGS. 12A and 12B shows a montage of micrographs representing an example of one growth assay plate. As shown in FIG. 12, column 1 contains cells that have not been stimulated, such that the cells do not proliferate (the background autofluorescence of the cells is measured that way) and column 12 shows growth of the endothelial cells upon exposure to a growth factor cocktail. Test wells will show different levels of cell growth or growth inhibition, based on the fluorescence quantified from each well. Wells which contain growth inhibitors (hits are defined using the SASD: sum of the average squared inside-cluster distances, Gagarin et al. *J. Biomol. Screen* 11:1-12, 2006) are shown in white boxes. Agents that cause a measurable decrease in the growth of the fluorescent cell line of interest are potential inhibitors of angiogenesis. Potential inhibitors of angiogenesis can then be tested for there effect on migration, and tubule formation, and for cytotoxicity using the disclosed assays.

In some examples, the effectiveness of the small molecules to inhibit tubule formation is determined. Exemplary methods for determining the effect of an agent on tube formation is given in Example 4. In a some assays, 50 µl of low growth factor BME is laid down in each well of a multiwell plate (such as a 96 well plate) and the plate is incubated for 1 hour at 37° C. Test agents are added to the plate either at a single concentration or at graded concentrations, for example from about 1 picomolar to about 100 millimolar (in some examples the test agents are added directly to the BME prior to plating). A cell mixture containing about 15,000 fluorescent PAE cells is then added on top of the gelled BME. The ability of the test agent to block tubule formation is determined, for example by comparing the number of tubes or related structures formed in a sample contacted with a test agent relative to a control, such as a sample not contacted with a test agent. In some examples, this is done by eye, for example by visual inspection of the cells with a fluorescent microscope after 3.5-24 hours. In some examples, images are acquired with a fluorescent microscope after 3.5-24 hours and stored, for example digitally. In some examples, quantitative evaluation of the effectiveness of the small molecules to block tube formation is assessed using the AngioApplication™ software. AngioApplication™ can compute multiple parameters which including but are not restricted to: single tube length, single tube area, total tube length, total tube area, node area, total number of tubes, total number of nodes, single node branching points, total number of branching points, average node branching points average tube length, average tube area, average node area, etc. Test agents identified as capable of inhibiting tubule formation are identified as potential angiogenesis inhibitors.

Potential angiogenesis inhibitors can be screened for cytotoxicity using the disclosed cytotoxicity assays, such as exemplified by Example 5. Increasing concentrations of potential angiogenesis inhibitors (such as from about 1 picomolar to about 100 millimolar) are added to cell mixtures containing fluorescent cell lines with distinguishable emission spectra. This method permits the cytotoxicity of a potential angiogenesis inhibitor on multiple cell lines to be determined simultaneously. After about 20 minutes supernatants are collected and transferred to a different plate and the fluorescence of the supernatants is measured at the appropriate wavelength corresponding to the emission spectra of the distinguishable emission spectra of the fluorescent proteins. The measured emission spectra from each of the distinguishable emission spectra is then used to determine the cytotoxicity of the potential angiogenesis inhibitor on the fluorescent cell lines in the mixture, for example by determining the EC50 of the potential angiogenesis inhibitor on the individual cell lines in the mixture. Potential angiogenesis inhibitors which show no or little cytotoxicity are considered putative antiangiogenic candidates and can move forward to in vivo studies.

Example 7

Tumor Stimulated Angiogenesis in 2D Co-Cultures does not Correlate with Xenograft Angiogenesis The stably-transfected fluorescent endothelial cells described herein enable the detection of angiogenic cell activities such as migration and tubule formation. Examples 3 and 4 demonstrate the stimulation of angiogenic activities in endothelial cultures incubated with various angiogenic stimuli. This example illustrates that tubule formation is analogously induced by tumor cells in 2D co-cultures, but that the angiogenic potential of particular tumor cell types in the 2D co-cultures does not correlate with the angiogenic behavior of xenografts of the same cell types.

Methods

Unless specified, all methods are as described in the previous examples.

2D Cell Cultures.

Tumor cells were grown in a 96-well plate in the medium previously described such as RPMI1640, DMEM, or F-12K, in accordance with the cell lines used herein, +10% fetal calf serum, to approximately 70% confluence and gently washed three times in PBS. 50 μl gel matrix were added and solidified at 37° C. A 100 μl aliquot of endothelial basal medium-2 (EBM-2) without serum supplementation and containing BEC or LEC at between 150,000-300,000 cell/ml were then added on top of the solidified gel matrix. Cultures were incubated at 37° C. and resulting tube formation determined in 4-6 hours.

Xenografts.

$1 \times 10^6$ or $1 \times 10^7$ tumor cells were injected subcutaneously in the hind flank of a nude mouse. A palpable mass is felt under the skin in 1-2 weeks having a tumor volume of approximately 50-100 $mm^3$. Mice were randomized into groups of 10 mice/group having tumor volumes of 50-100 $mm^3$, and drug treatment was started at this time. Treatment was continued for an additional 2-3 weeks or until tumors reached a maximum volume of 2000 $mm^3$. For biopsy studies, tumors were excised at a volume <1000 $mm^3$, gross morphology photographs were taken and either sectioned in half for a second gross morphology picture showing internal structure of tumor mass or a core biopsy taken through the entire tumor nodule resulting in a traversing "sausage" tissue sample having peripheral, mid section and center anatomical regions that were ultimately sliced into cross-sections and placed into the 3D drug sensitivity assay (see Example 8).

Results

Figure 20:
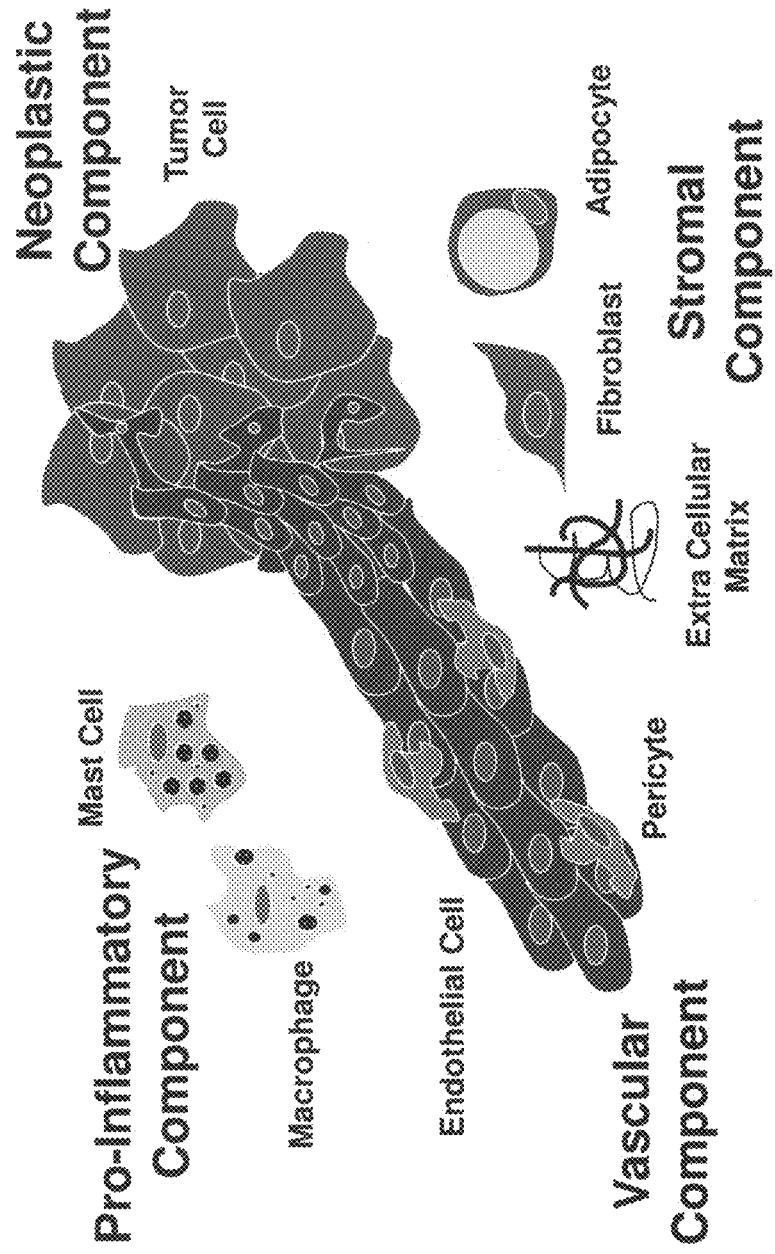
FIG. 20 is a drawing showing several interactive cellular components involved with tumor associated angiogenesis/lymphangiogenesis.

Induction of angiogenesis in the tumor microenvironment is a multi-stage process, involving multiple factors and cell types (FIG. 20). As shown in Examples 3 and 4, stably-transfected fluorescent endothelial cells can be used to model angiogenic activities in vitro in response to chemical stimuli provided in culture medium. Tubule formation was monitored in Example 3 in 2D cultures that were prepared with endothelial cells layered on top of solidified gel matrix (FIG. 21 top right).

Figure 21:
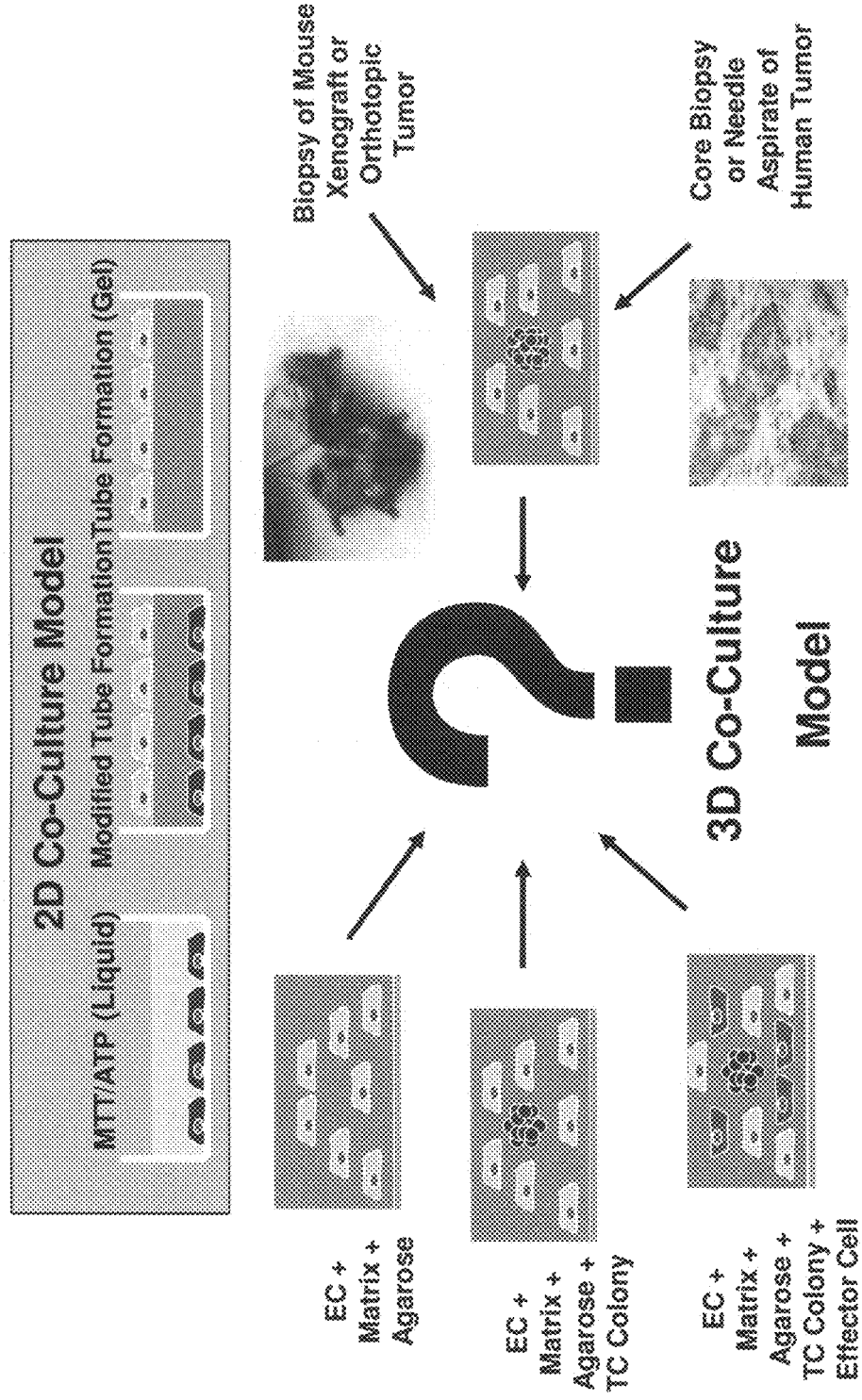
FIG. 21 shows 2D and 3D co-culture approaches to simulate the in vivo angiogenic interactions between tumor and endothelial cells.
Figure 22:
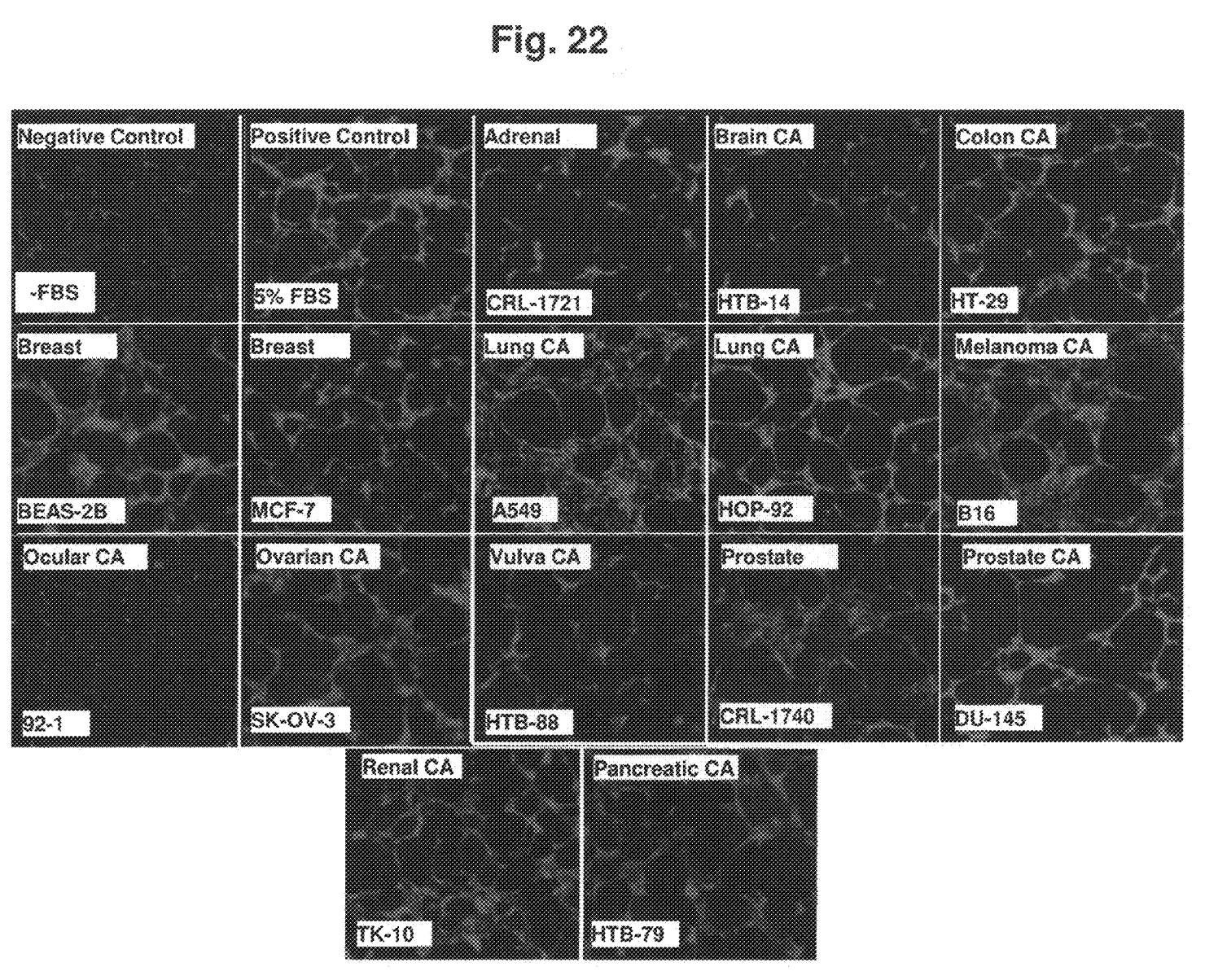

To determine the influence of tumor cells on endothelial tubule formation, tubule formation was monitored in modified 2D co-cultures of endothelial cells layered on top of gel matrix that was solidified on top of a monolayer of a tumor cell line (FIG. 21, top center). Using this modified 2D co-culture assay, tubule formation in fluorescent PAE cells was stimulated by several different tumor cell lines and observed after a six-hour incubation (FIG. 22). Of the cell lines tested, ocular melanoma 92-1 cells displayed the least tubule inductive potential, while lung carcinoma A549 induced robust tubule formation.

Figure 23:
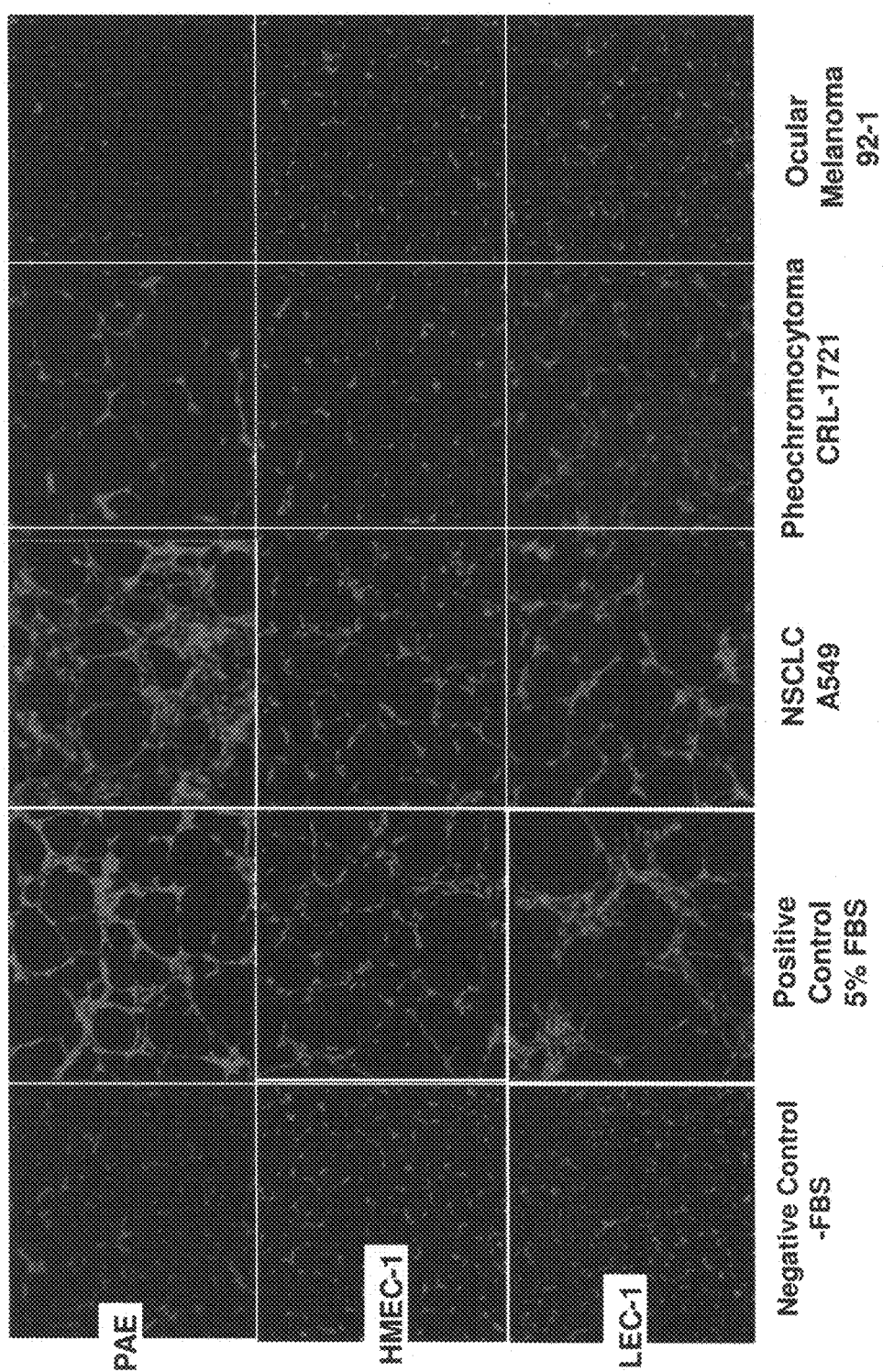
FIG. 23 is a series of photomicrographs of 2D co-cultures comparing the tube formation response of different endothelial cells (PAE, HMEC or LEC-1) vs. different tumor cells (A549, CRL-1721 or 92-1). Endothelial cells (at approximately 18,000/well) were plated on top of matrigel solidified on top of a monolayer of indicated tumor cell line.

The separate influences of three tumor cell lines (lung carcinoma A549, pheochromocytoma PC-12 (CRL-1721), and ocular melanoma 92-1) on tubule formation in three endothelial cell lines (PAE, HMEC-1, and LEC-1) was similarly tested. As shown in FIG. 23, A549 cells induced robust tubule formation in all endothelial cells tested. In contrast, 92-1 cells did not stimulate tubule formation in any of the cells tested.

One goal of the modified 2D co-culture assays was to develop a mimetic of the in vivo effects of a tumor on angiogenesis. To establish the correlation between the modified 2D co-culture results and in vivo tumor activity, tumor xenografts were produced in nude mice using lung carcinoma A549, pheochromocytoma PC-12, and ocular melanoma 92-1 cells.

Figure 24:
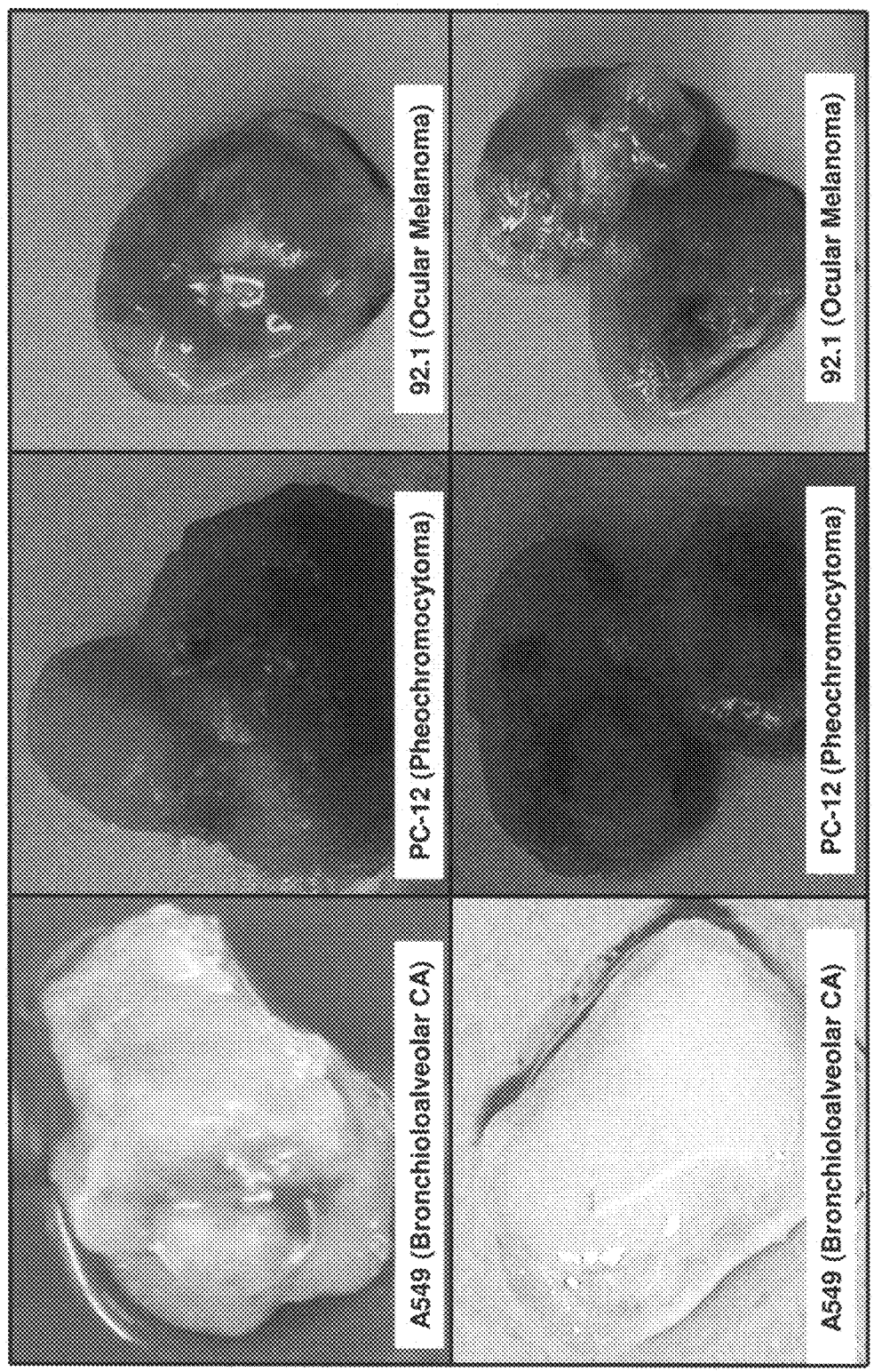
FIG. 24 is a series of photographs of human/rat xenograft tumors (A549 (left), PC-12 (middle), and 92-1 (right)) excised from nude mice. Top row shows whole tumors and peripheral vascularization. Bottom row shows tumors sectioned to display angiogenesis through tumor core.

Resultant tumors were excised and blood vessel formation observed in the periphery (FIG. 24, top panels) and interior (FIG. 24, bottom panels) of the tumors. PC-12 and 92-1 tumors had abundant vasculature both on the periphery as well as the interior of the tumors. In contrast, the A549 tumor displayed moderate vascularization on the periphery of the tumor, but little vasculature in the tumor interior.

These xenograft results strongly diverge from the induction of tubule formation observed in the modified 2D co-cultures. Thus, the modified 2D co-cultures cannot serve as a mimetic of in vivo tumor-induced angiogenesis.

Example 8

Recapitulation of In Vivo Tumor Activities in 3D Co-Cultures

As shown in Example 7, tumor cell-induced endothelial tubule formation in modified 2D co-cultures does not correlate with angiogenesis in a corresponding nude mouse xenograft model. This example describes a 3D co-culture assay system that accurately recapitulates the in vivo activity of tumor xenografts. Migration of tumor cells along endothelial tubules, or angiotropism, was also observed in the described 3D co-culture system. Thus, the 3D co-cultures provide a model to monitor both angiogenic and metastatic potential of a tumor.

Methods

Unless specified herein, methods were as described in the preceding examples.

Tumor Spheroids.

Tumor spheroid colonies were prepared according to a modified protocol based on Hamburger et al. (*Science*, 197: 461-463, 1977). 2% SEAPLAQUE® Agarose (FMC Bio-Products) was prepared in deionized water and autoclaved. The agarose was cooled in a 40° C. water bath. 10×RPMI 1640 medium (Sigma-Aldrich), FBS, Antibiotic-Antimycotic (a.k.a. Anti-Anti), and sterile deionized water (Invitrogen) were warmed in a 40° C. water bath. Appropriate volumes of the deionized water, 100× Antibiotic-Antimycotic, FBS, 10×RPMI1640 medium, and 2% agarose were mixed to make the final concentration of 1% agarose with 20% FBS, 2× Antibiotic-Antimycotic, and 1× RPMI1640. 1.5 ml of the mixture was added to each well of 6-well plate (Corning) and set aside to solidify for 20 minutes in the hood. In the meantime, tumor cells at approximately 70% confluence were harvested and counted. Tumor cells were suspended at 15,000 cells/ml in 0.2% of agarose, 2× Antibiotic-Antimycotic, 20% FBS, and 1×RPMI1640. 3 ml of the tumor cell suspension was added to the well with the first solidified layer in the 6-well plate. This plate was left in the hood for 10 minutes and then carefully transferred to an incubator with 100% humidity for 20-30 days. The well-formed colonies were harvested by adding 2 ml of 1×PBS to each well of a 6-well plate and pipetted up and down for sufficient number of times until the agarose was broken into tiny pieces. The colonies were washed three times in PBS to get rid of the agarose residue. The colonies were suspended in sterile PBS with 1% glucose, 0.3 mM EDTA, 0.5% BSA and 1× Antibiotic-Antimycotic. The bright fluorescent colonies were picked up using an Olympus inverted fluorescent microscopy (Olympus, Japan) for 3D co-culture.

Xenograft Biopsy.

Xenografts were prepared as in Example 7. Tumor xenografts were dissected when they reached about 1 cm in diameter and put into the sterile 15 ml or 50 ml tubes (Corning) with RPMI1640 medium supplemented with 10% FBS, 1% Glucose (Sigma), and 4× Antibiotic-Antimycotic (Invitrogen). The tumor xenografts were placed on wet ice and shipped to the lab within 2-3 hours. The Xenografts were rinsed 3 times in 70% ethanol and then 3 times in PBS. In the hood, the core biopsy was performed by biopsy punch (Miltex, Inc.) and was washed out into a 100 cm cell culture dish (Corning) by using a pipette to blow the top opening of the biopsy applicator. Using a disposable scalpel (Feather Safety Razor, Co. Japan), the core biopsy was dissected in three stages. 1 mm of both ends of the core biopsy was carefully cut off; they were transferred into a new 100 cm cell culture dish labeled P (peripheral section). Next, 1 mm of both ends of the remaining core biopsy were removed and discarded. 1 mm of both ends of the core biopsy were cut off and transferred into a new 100 cm cell culture dish labeled M (middle section). Lastly, 1 mm of both ends of the remaining biopsy tissue were removed and discarded. The rest of the core biopsy was transferred into a new 100 cm cell culture dish labeled C (center section). A drop of PBS was added to each section P, M, and C to keep them moist. Using the disposable scalpel, each section was cut into small pieces, approximately 10 pieces per 1 mm section, under the dissection microscope (LeicaMZ125, Leica, Germany). For the 3D co-cultures, each piece of the biopsy was transferred to the center of the well of the second layer of the gel matrix suspension comprising individual endothelial cells and/or other component cells in a prepared 96-well plate kept on wet ice. The plate was then placed in the incubator at 37° C. for 45 minutes to allow the gel matrix to solidify. The third layer comprising the liquid medium was then added to the wells for culturing.

3D Co-Cultures.

3D co-cultures were prepared as follows: 50 µl 1% SEAKEM™ LE agarose were added to individual wells of a 96-well plate and allowed to solidify at room temperature for 20 minutes. 30 µl GELTREX® gel matrix (Invitrogen) were combined with PAE, LEC or HMEC-1 cells at a cell density of 560,000 cells/ml and added to each well of the plate (atop the solidified agarose). Plates were maintained on wet ice (4° C.) to prevent solidification of the gel matrix/cell mixture (the second layer). A single tumor cell spheroid colony or single ringlet of xenograft core biopsy was added to the center of the well and the matrix gel was solidified at 37° C. On top of the tumor/endothelial cell gel layer, 80 µl EBM-2+1% FBS were added to a final concentration of EMB-2+0.5% FBS in relation to the total volume of the culture. Cultures were incubated at 37° C. for 5-20 days and endothelial vessel network formation was observed by confocal laser scanning fluorescence microscopy.

Results

Modified 2D co-cultures (Example 7) enabled observation of induction of endothelial tubule formation by a tumor cell line. However, angiogenesis in the modified 2D co-cultures did not correlate with in vivo tumor activity in nude mouse xenografts.

In order to more accurately reproduce the tumor microenvironment illustrated in FIG. 20, 3D co-cultures were developed (FIG. 21, bottom). In the 3D co-cultures, tumor and endothelial cells were mixed together in gel matrix (second layer) and layered on top of agarose (first layer) that had been previously solidified in the wells of a 96-cell culture plate. Culture media (third layer) was provided on top of the tumor/endothelial cell gel layer (second layer).

Employing the 3D co-culture assay, endothelial tubule formation was observed in the presence of tumor xenograft tissue (FIG. 25) and single tumor spheroid colonies (FIGS. 26-29). Tubule formation was not observed in co-cultures between endothelial cells and dispersed tumor cells, though endothelial cell migration was observed.

Figure 29:
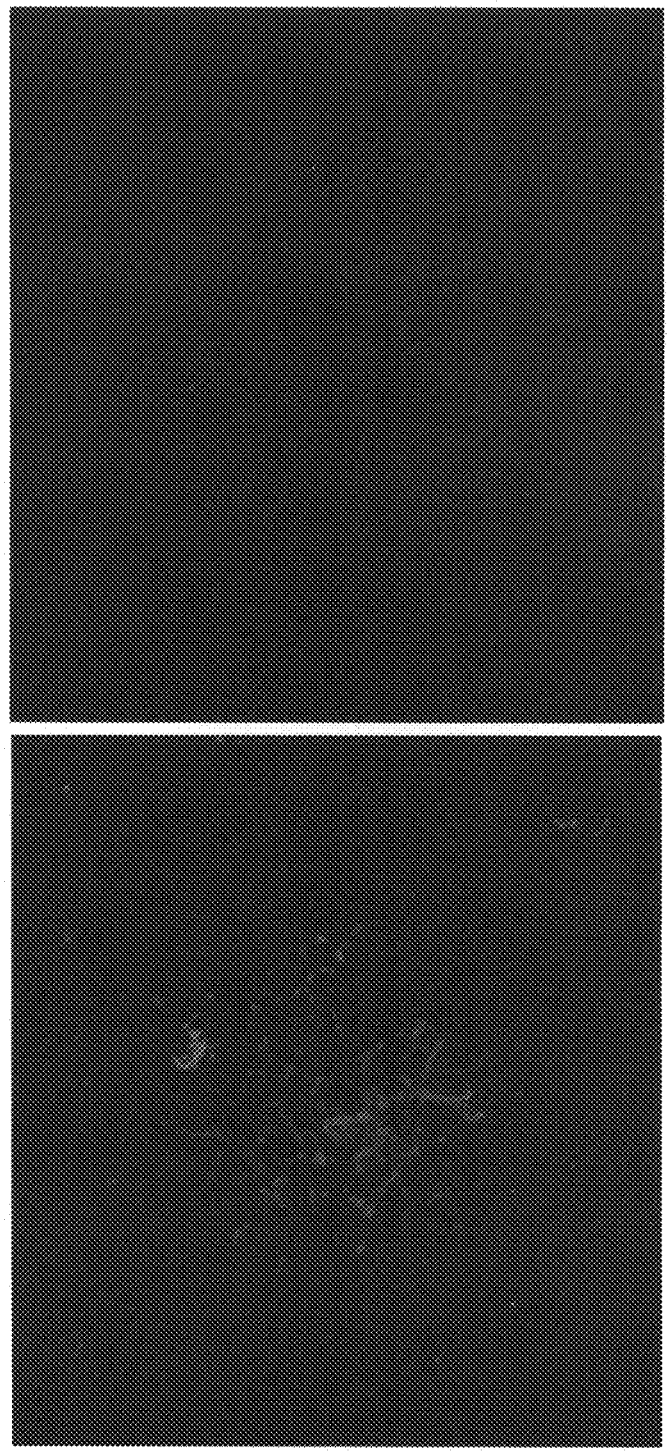
FIG. 29 shows confocal photomicrographs of twenty-day 3D co-cultures of HMEC-1 endothelial cells (red) and human tumor cells (blue). Co-cultures with ocular melanoma 92.1 (left) and lung cancer A549 (right) are shown.

In contrast to the 2D co-cultures, tubule formation in the 3D co-cultures recapitulated in vivo angiogenesis in the nude mice xenografts. Specifically, ocular melanoma 92-1, which produced a highly vascularized xenograft tumor, induced robust tubule formation after a nine-day incubation (FIG. 26) in the described 3D co-culture system. Moreover, lung carcinoma A549 cells, which produced a xenograft tumor that was only poorly and peripherally vascularized, induced moderate peripheral tubule formation after a twelve-day incubation (FIG. 28) in the described 3D co-culture system. Similar results were observed for both tumor cell lines after a twenty-day incubation (FIG. 29). Thus, the described 3D co-cultures provide an in vitro model for angiogenesis that directly correlate with in vivo tumor activity.

Figure 27:
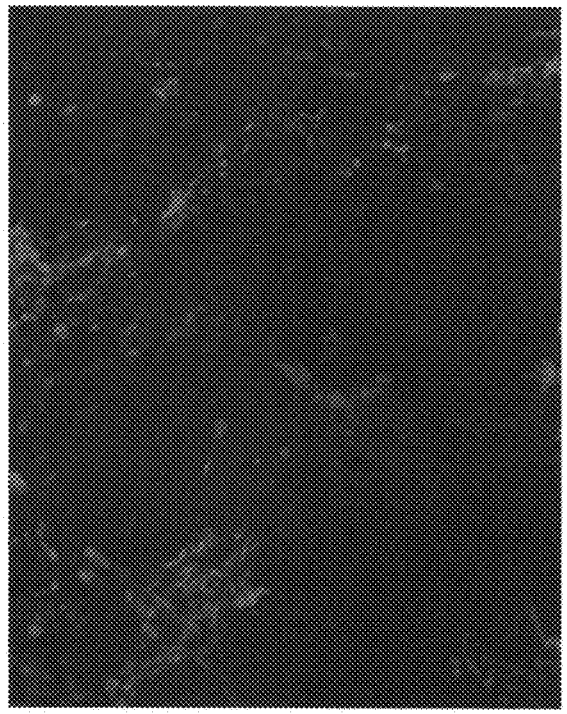
FIG. 27 is a confocal photomicrograph of a nine-day 3D co-culture of BEC-1 endothelial cells (red) and rat pheochromocytoma PC-12 (blue).
Figure 26:
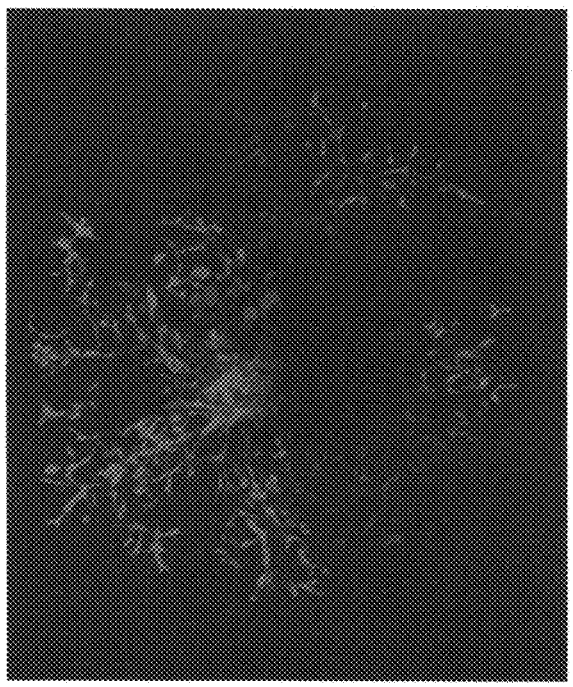
FIG. 26 is a confocal photomicrograph of a nine-day 3D co-culture of PAE endothelial cells (red) and 92-1 ocular melanoma (blue).
Figure 28:
FIG. 28 is a confocal photomicrograph showing perituмoral vascularization in a twelve-day 3D co-culture of PAE endothelial cells (red) and NSCLC A549 (blue).

Evaluation of highly metastatic human tumor cell lines such as pheochromocytoma or melanoma in the 3D in vitro co-culture model system also demonstrated migration of individual cancer cells along vascular highways (FIGS. 27 and 29). This cellular migration extended far beyond cellular branch projections from the main tumor spheroid seed colony. Vessel-mediated cancer cell migration is known as angiotropism, and has been reported to occur in pathological specimens of human glioma/glioblastoma and melanoma (Lugassy et al., *Am. J. Dermatopath.*, 24:473-478, 2002; and Lugassy and Barnhill, *Adv. Anat. Pathol.*, 14:195-201, 2007). Thus, in addition to providing an in vitro model for tumor-induced angiogenesis, the 3D co-cultures also provide a model for tumor metastasis.

Example 9

Methods of Testing Anti-Angiogenic Tumor Therapies Using 3D Co-Cultures

The 3D co-cultures described herein provide an in vitro model that correlates with in vivo tumor induction of angiogenesis. With the 3D co-cultures, it becomes possible to design individualized anti-angiogenic tumor therapies that are tailored to best inhibit induction of angiogenesis by a tumor in a subject. This example shows the testing of anti-angiogenesis treatments using the 3D co-culture assay of endothelial tubule formation.

Methods

Unless specified, all methods were as described in the previous examples.

3D Cell Cultures.

3D cultures were prepared as in Example 8, except EBM-2 medium was provided on top of the solidified tumor/endothelium/gel layer containing final concentrations of 0.5% FBS and 0.1% DMSO, plus angiogenesis inhibitor. Final drug concentrations were as follows: Avastin® at 100 µg/ml; Thalidomide at 100 µM; Sunitinib at 6 µg/ml; and Fumagilin at 1 µM.

Results

Tumor cell-induced endothelial cell tubule formation in 3D co-cultures correlated with angiogenesis in tumor xenografts. The 3D co-cultures can therefore be used to monitor the in vitro angiogenic potential of tumor tissue isolated from a subject. In particular, the efficacy of multiple angiogenesis inhibitors in vitro can be tested and monitored with a high degree of predictive correlation with the in vivo context.

Figure 30:
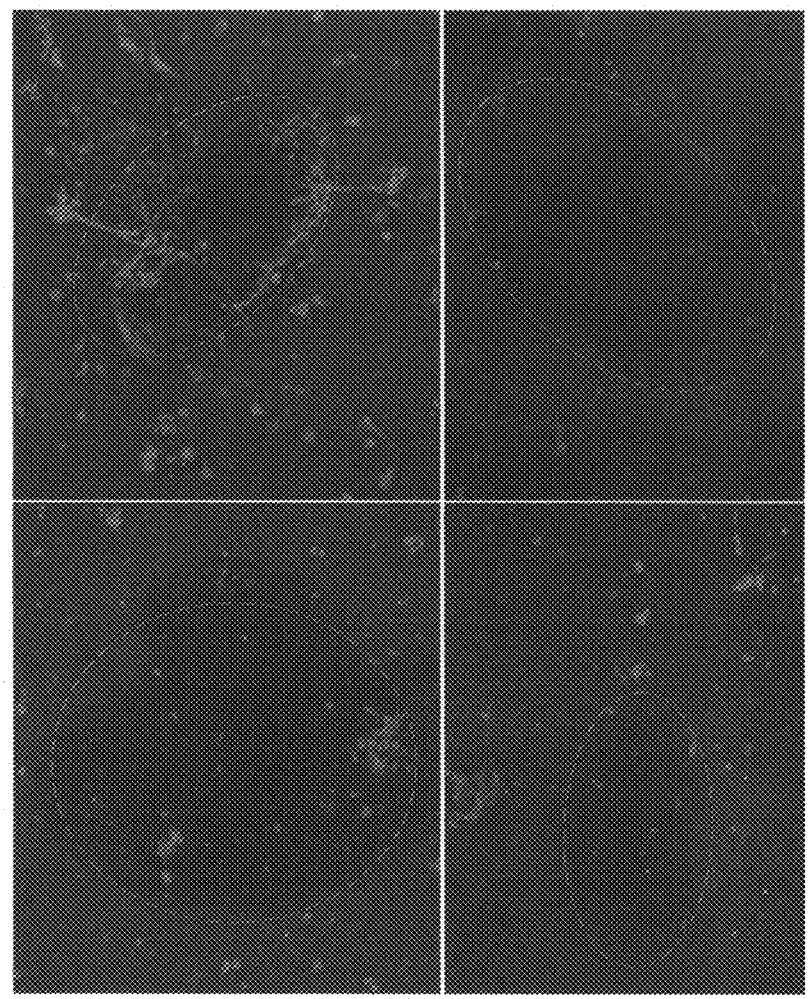
FIG. 30 shows confocal photomicrographs of six-day 3D co-cultures of PAE (red) and leiomyosarcoma HTB-88 core biopsy xenograft (blue dashed ellipses). Peripheral (top) or central (bottom) xenograft tissue was cultured with PAE. Co-cultures were incubated with (left) or without (right) Avastin®.

To examine the utility of the 3D co-cultures to test the effects of an angiogenesis inhibitor, 3D co-cultures were prepared combining stably transfected fluorescent PAE cells and biopsy tissue from peripheral or central tissue of a leiomyosarcoma HTB-88 xenograft. The prepared co-cultures were incubated for six days with the FDA-approved angiogenesis inhibitor Avastin®. As shown in FIG. 30, Avastin® treatment inhibited both PAE proliferation as well as tubule formation. Moreover, regional differences of biopsy material (periphery, midsection, core) in the tumor angiogenic potential were observed, with outer geographic tumor areas always demonstrating dramatically more vessel induction than inner tissue regions (FIG. 30, compare top and bottom panels).

Identifying the most efficacious therapy for a particular patient is a crucial goal for successful cancer treatment. To demonstrate the use of the 3D co-culture assay for tailoring anti-angiogenesis treatment to a particular tumor from a particular patient, the effect of several different angiogenesis inhibitors on tubule formation in 3D co-cultures was tested. Several FDA approved anti-angiogenic compounds were assessed in this capacity, including Avastin®, Thalidomide, and Sunitinib as well as the non-FDA approved drug Fumagillin. After a five-day incubation, Avastin® demonstrated the greatest inhibition of proliferation and tubule formation.

Together, these observations validate the use of 3D co-cultures to personalize anti-angiogenesis cancer therapy and monitor the efficacy of the chosen treatment. The existence of tumor heterogeneity was also observed.

Example 10

Testing Anti-Metastatic Tumor Therapies Using 3D Co-Cultures

Example 9 demonstrated that the 3D co-cultures described herein can be used to test the efficacy of a panel of anti-angiogenic tumor therapies for given subject. The tumor cell angiotropism observed in FIGS. 27 and 29 indicates that tumor metastasis can also be detected using the 3D co-cultures. This example provides a method for optimizing anti-metastatic therapy to inhibit metastasis in a subject.

3D co-cultures can be established as described herein. For example, co-cultures can be prepared in several wells of a 96-well culture plate. Tumor cells used in the co-culture can be a sample of a tumor biopsy from a subject or a spheroid colony derived from a tumor biopsy from a subject. As with the anti-angiogenic compounds tested in Example 9, one or more anti-metastatic compounds can be combined with culture medium and applied to some but not all of the established 3D co-cultures. The 3D co-cultures are incubated for any length of time sufficient to detect angiotropism, such as nine days, and angiotropism observed under a microscope. The relative efficacy of an anti-metastatic compound is determined by the comparative inhibition of angiotropism in relation, for instance, to the 3D co-culture that did not receive any anti-metastatic compound. Those compounds with the strongest inhibitory effect on angiotropic cell motility (for example, the distance moved from core tumor cell colony) are most efficacious.

Example 11

Personalized Anti-Angiogenic or Anti-Metastatic Cancer Therapy

This example provides representative methods of selecting and monitoring the efficacy of an anti-angiogenic or anti-metastatic cancer therapy for a specific subject.

Using the 3D co-cultures described herein, cancer therapy can be tailored to a specific subject and the effectiveness of the therapy monitored over time. A tumor biopsy or other cancer cell sample from a patient (the target patient or target subject) can be the source of cancerous tissue for incorporation into multiple 3D co-cultures. As described Examples 9 and 10, the 3D co-cultures can be used to select the most efficacious anti-angiogenic and/or anti-metastatic compound for the target patient, from among a panel of anti-angiogenic or anti-metastatic drugs. Additionally, the effects of combining the selected anti-angiogenic and anti-metastatic drugs can also be observed. The selected compound(s) can then be administered to the target patient as part of an anti-cancer therapy regimen.

The continued efficacy of the selected compound(s) can be monitored by obtaining a tumor biopsy from the subject after a given period of time, for example three months, and preparing 3D co-cultures to observe the effect of the administered treatment on angiogenesis and/or metastasis. If the development drug resistance is observed, a new personalized treatment can then identified using the foregoing methods.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

We claim:

1. A method for monitoring angiogenic or metastatic potential of tumor cells comprising:
    preparing a three-dimensional co-culture comprising:
        a first layer comprising a neutral polysaccharide polymer gel in contact with the bottom of a culture dish;
        a second layer on top of the first layer, comprising:
            a solidified gel matrix;
            endothelial cells dispersed in the solidified gel matrix; and
            tumor cells comprising either a single monoclonal tumor spheroid colony or a sample of a tumor biopsy, suspended in the solidified gel matrix, wherein the monoclonal tumor spheroid colony is produced using a method comprising:
                (i) preparing a culture in which monoclonal tumor spheroid colonies are grown, comprising:
                    a bottom layer comprising 1% agarose with 20% FBS, 2× Antibiotic-Antimycotic, and 1×RPMI1640; and
                    a top layer overlaying the bottom layer, wherein the top layer comprises isolated tumor cells suspended in 0.2% of agarose, 2× Antibiotic-Antimycotic, 20% FBS, and 1×RPMI1640;
                (ii) incubating the culture to grow monoclonal spheroid colonies;
                (iii) harvesting monoclonal tumor spheroid colonies from the culture; and
                (iv) resuspending the monoclonal tumor spheroids in phosphate buffered saline with 1% glucose, 0.3 mM EDTA, 0.5% BSA and 1× Antibiotic-Antimycotic; and
        a third layer on top of the second layer, comprising culture medium;
    incubating the three-dimensional co-culture; and
    detecting at least one of endothelial cell proliferation, endothelial cell tubule formation, or tumor cell angiotropism of the cells in the second layer that correlates in a tumor-specific manner with endothelial cell proliferation, endothelial cell vessel formation, or tumor cell angiotropism in vivo.

2. The method of claim 1, wherein the neutral polysaccharide polymer gel comprises agarose.

3. The method of claim 1, wherein the endothelial cells stably and constitutively express a fluorescent protein.

4. The method of claim 3, wherein the tumor cells stably and constitutively express a fluorescent protein with a different emission spectrum from the fluorescent protein expressed by the endothelial cells.

5. The method of claim 3, wherein the second layer further comprises at least one additional mammalian cell type dispersed in the solidified gel matrix, and wherein the at least one additional mammalian cell type stably and constitutively expresses a fluorescent protein with a different emission spectrum from the fluorescent protein expressed by the endothelial cells.

6. The method of claim 4, wherein the second layer further comprises at least one additional mammalian cell type dispersed in the solidified gel matrix, and wherein the at least one additional mammalian cell type stably and constitutively expresses a fluorescent protein with a different emission spectrum from either of the fluorescent proteins expressed by the endothelial cells or the tumor cells.

7. The method of claim 1, wherein the second layer further comprises at least one additional mammalian cell type dispersed in the solidified gel matrix.

8. The method of claim 7, wherein the at least one additional mammalian cell type is a cell selected from the group consisting of macrophage, mast cell, fibroblast, adipocyte, and pericyte.

9. The method of claim 1, wherein the first, second, or third layer further comprises at least one test agent.

10. The method of claim 9, wherein the test agent is a known or potential inhibitor of angiogenesis or metastasis.

11. The method of claim 1, wherein the tumor cells are obtained from a subject and the first, second, or third layer further comprises at least one test agent that has been administered to the subject as part of a cancer treatment.

12. A method of testing the efficacy of an anti-angiogenic or anti-metastatic cancer treatment for a subject, comprising monitoring angiogenic or metastatic potential of tumor cells by the method of claim 1, wherein the tumor cells are obtained from the subject and the first, second, or third layer comprises at least one test agent that is a candidate anti-cancer treatment.

13. A method of selecting a personalized anti-angiogenic or anti-metastatic treatment for cancer in a subject comprising:
    preparing multiple three-dimensional co-cultures, each co-culture comprising:
        a first layer comprising a neutral polysaccharide polymer gel in contact with the bottom of a culture dish;
        a second layer on top of the first layer, comprising:
            a solidified gel matrix;
            endothelial cells dispersed in the solidified gel matrix; and
            tumor cells comprising either a single monoclonal tumor spheroid colony or a sample of a tumor biopsy, suspended in the solidified gel matrix, wherein the monoclonal tumor spheroid colony is produced using a method comprising:
                (i) preparing a culture in which monoclonal tumor spheroid colonies are grown, comprising:
                    a bottom layer comprising 1% agarose with 20% FBS, 2× Antibiotic-Antimycotic, and 1×RPMI1640; and
                    a top layer overlaying the bottom layer, wherein the top layer comprises isolated tumor cells suspended in 0.2% of agarose, 2× Antibiotic-Antimycotic, 20% FBS, and 1×RPMI1640;

(ii) incubating the culture to grow monoclonal spheroid colonies;

(iii) harvesting monoclonal tumor spheroid colonies from the culture; and (iv) resuspending the monoclonal tumor spheroids in phosphate buffered saline with 1% glucose, 0.3 mM EDTA, 0.5% BSA and 1× Antibiotic-Antimycotic; and a third layer on top of the second layer, comprising culture medium, wherein all but one of the co-cultures further comprises at least one test agent comprising an anti-angiogenic or anti-metastatic compound in the first, second, or third layers;

incubating the three-dimensional co-cultures;

detecting at least one of endothelial cell proliferation, endothelial cell tubule formation, or tumor cell angiotropism of the cells in the second layer that correlates in a tumor-specific manner with endothelial cell proliferation, endothelial cell vessel formation, or tumor cell angiotropism in vivo; and selecting the at least one test agent causing a decrease in at least one of endothelial cell proliferation, endothelial cell tubule formation or tumor cell angiotropism in cells of the co-culture with the test agent in the medium, in comparison to endothelial cell proliferation, endothelial cell tubule formation or tumor cell angiotropism in the cells of the co-culture without the test agent in the medium.

14. The method of claim 13, wherein the neutral polysaccharide polymer gel comprises agarose.

15. The method of claim 13, wherein the endothelial cells stably and constitutively express a fluorescent protein.

16. The method of claim 15, wherein the tumor cells stably and constitutively express a fluorescent protein with a different emission spectrum from the fluorescent protein expressed by the endothelial cells.

17. The method of claim 15, wherein the second layer further comprises at least one additional mammalian cell type dispersed in the solidified gel matrix, and wherein the at least one additional mammalian cell type stably and constitutively expresses a fluorescent protein with a different emission spectrum from the fluorescent protein expressed by the endothelial cells.

18. The method of claim 16, wherein the second layer further comprises at least one additional mammalian cell type dispersed in the solidified gel matrix, and wherein the at least one additional mammalian cell type stably and constitutively expresses a fluorescent protein with a different emission spectrum from the either of the fluorescent proteins expressed by the endothelial cells or the tumor cells.

19. The method of claim 13, wherein the second layer further comprises at least one additional mammalian cell type dispersed in the solidified gel matrix.

20. The method of claim 19, wherein the at least one additional mammalian cell type is a cell type selected from the group consisting of macrophage, mast cell, fibroblast, adipocyte, and pericyte.

* * * * *